United States Patent
Arlen

(10) Patent No.: US 11,279,768 B1
(45) Date of Patent: Mar. 22, 2022

(54) ANTI-CANCER ANTIBODIES, COMBINATION THERAPIES, AND USES THEREOF

(71) Applicant: PRECISION BIOLOGICS, INC., Rockville, MD (US)

(72) Inventor: Philip M. Arlen, Great Neck, NY (US)

(73) Assignee: PRECISION BIOLOGICS, INC., Rockville, MD (US)

(*) Notice: Subject to any disclaimer, the term of this patent is extended or adjusted under 35 U.S.C. 154(b) by 0 days.

(21) Appl. No.: 15/090,008

(22) Filed: Apr. 4, 2016

Related U.S. Application Data

(60) Provisional application No. 62/142,770, filed on Apr. 3, 2015.

(51) Int. Cl.
| | |
|---|---|
| A61K 45/06 | (2006.01) |
| C07K 16/30 | (2006.01) |
| A61K 39/395 | (2006.01) |
| A61N 5/10 | (2006.01) |

(52) U.S. Cl.
CPC ........ *C07K 16/30* (2013.01); *A61K 39/39558* (2013.01); *A61K 45/06* (2013.01); *C07K 16/303* (2013.01); *C07K 16/3015* (2013.01); *C07K 16/3023* (2013.01); *C07K 16/3046* (2013.01); *C07K 16/3069* (2013.01); *A61N 2005/109* (2013.01); *A61N 2005/1021* (2013.01); *A61N 2005/1087* (2013.01); *A61N 2005/1089* (2013.01); *A61N 2005/1098* (2013.01); *C07K 2317/24* (2013.01); *C07K 2317/56* (2013.01); *C07K 2317/565* (2013.01); *C07K 2317/732* (2013.01)

(58) Field of Classification Search
CPC .............................. A61K 39/395; C07K 16/30
USPC ........................................................ 424/130.1
See application file for complete search history.

(56) References Cited

U.S. PATENT DOCUMENTS

| | | | |
|---|---|---|---|
| 4,275,149 | A | 6/1981 | Litman et al. |
| 4,366,241 | A | 12/1982 | Tom et al. |
| 4,376,110 | A | 3/1983 | David et al. |
| 4,517,288 | A | 5/1985 | Giegel et al. |
| 4,816,567 | A | 3/1989 | Cabilly et al. |

(Continued)

FOREIGN PATENT DOCUMENTS

| | | |
|---|---|---|
| EP | 0404097 | 9/1996 |
| WO | WO 1991/005264 | 4/1991 |

(Continued)

OTHER PUBLICATIONS

Harmsen and Haard (Appl Microbiol Biotechnol 2007, 77:13-22).*

(Continued)

*Primary Examiner* — Yan Xiao
(74) *Attorney, Agent, or Firm* — Robin L. Teskin; Baker, Donelson, Bearman, Caldwell & Berkowitz PC

(57) ABSTRACT

This invention relates to antibodies to anti-cancer antibodies and uses thereof, including combination therapies and compositions. Combinations targeting the extrinsic, intrinsic, or common pro-apoptotic pathways are provided. Exemplary anti-cancer antibodies are differentially expressed in cancers, such as antibodies targeting the bind the antigens NPC-1, 16C3, or 31.1. Exemplary anti-cancer antibodies target lung cancer, ovarian cancer, cervical cancer, uterine cancer, pancreas cancer, breast cancer, and colon cancer.

20 Claims, 5 Drawing Sheets

Specification includes a Sequence Listing.

(56) References Cited

U.S. PATENT DOCUMENTS

| | | | |
|---|---|---|---|
| 4,837,168 A | 6/1989 | de Jaeger et al. | |
| 4,933,294 A | 6/1990 | Waterfield et al. | |
| 5,401,638 A | 3/1995 | Carney et al. | |
| 5,500,362 A | 3/1996 | Robinson et al. | |
| 5,591,828 A | 1/1997 | Bosslet et al. | |
| 5,641,870 A | 6/1997 | Rinderknecht et al. | |
| 5,821,337 A | 10/1998 | Carter et al. | |
| 6,509,154 B1 | 1/2003 | Paillette | |
| 6,696,686 B1 | 2/2004 | Wainer et al. | |
| 7,314,622 B2 | 1/2008 | Arlen et al. | |
| 7,741,282 B2 | 6/2010 | Lin et al. | |
| 7,763,720 B2 | 7/2010 | Arlen et al. | |
| 7,829,678 B2 | 11/2010 | Bristol et al. | |
| 8,524,456 B2 * | 9/2013 | Bristol ................. | C07K 16/303 435/7.1 |
| 8,802,090 B2 * | 8/2014 | Bristol ................. | C07K 16/303 424/130.1 |
| 9,371,375 B2 * | 6/2016 | Bristol ................. | C07K 16/303 |
| 2008/0227965 A1 | 9/2008 | Arlen et al. | |
| 2009/0162931 A1 | 6/2009 | Bristol et al. | |
| 2010/0310559 A1 | 12/2010 | Arlen et al. | |
| 2011/0076761 A1 | 3/2011 | Bristol et al. | |
| 2011/0129416 A1 | 6/2011 | Bristol et al. | |
| 2011/0158902 A1 | 6/2011 | Arlen et al. | |
| 2011/0165599 A1 | 7/2011 | Arlen et al. | |
| 2012/0034227 A1 | 2/2012 | Arlen et al. | |
| 2014/0220113 A1 | 8/2014 | Kreutzer et al. | |
| 2014/0377274 A1 | 12/2014 | Maker | |

FOREIGN PATENT DOCUMENTS

| | | | |
|---|---|---|---|
| WO | WO 1993/011161 | | 6/1993 |
| WO | WO 1997/001633 | | 1/1997 |
| WO | WO 1997/025428 | | 7/1997 |
| WO | WO 1999/007409 | | 2/1999 |
| WO | WO 1999/032619 | | 7/1999 |
| WO | WO 2000/001846 | | 1/2000 |
| WO | WO 2000/044895 | | 8/2000 |
| WO | WO 2000/044914 | | 8/2000 |
| WO | WO 2001/000832 | | 1/2001 |
| WO | WO 2001/029058 | | 4/2001 |
| WO | WO 2001/036646 | | 5/2001 |
| WO | WO 03/070234 | * 8/2003 | ............. A61K 31/13 |
| WO | WO 2006/113546 | | 10/2006 |
| WO | WO 2009/062050 | | 5/2009 |
| WO | WO 2011/163401 | | 12/2011 |
| WO | WO 2012/040617 | | 3/2012 |

OTHER PUBLICATIONS

Weisenthal (Human Tumor Assay Journal, on-line at http://weisenthal.org/synergy1.htm, Mar. 14, 2012).*
Berenbaum (Clin. Exp Immunol. 28:1-18, 1977).*
Ackerman ME, Chalouni C, Schmidt MM, Raman VV, Ritter G, Old LJ, Mellman I, Wittrup KD. A33 antigen displays persistent surface expression. Cancer Immunology, Immunotherapy. Jul. 1, 2008;57(7):1017-27.
Ahnesjö A, Aspradakis MM. Dose calculations for external photon beams in radiotherapy. Physics in medicine and biology. Nov. 1999;44(11):R99.
Allshire R. RNAi and heterochromatin—a hushed-up affair. Science. Sep. 13, 2002;297(5588):1818-9.
Bass BL. RNA interference: The short answer. Nature. May 24, 2001;411(6836):428-9.
Blum HE. Colorectal cancer: future population screening for early colorectal cancer. European Journal of Cancer. Aug. 31, 1995;31(7):1369-72.
Blumenthal RD, Hansen HJ, Goldenberg DM. Inhibition of adhesion, invasion, and metastasis by antibodies targeting CEACAM6 (NCA-90) and CEACAM5 (Carcinoembryonic Antigen). Cancer research. Oct. 1, 2005;65(19):8809-17.
Blumenthal, et al. (2007) BMC Cancer 7(2): 1-15.

Buchsbaum DJ, Zhou T, Grizzle WE, Oliver PG, Hammond CJ, Zhang S, Carpenter M, LoBuglio AF. Antitumor efficacy of TRA-8 anti-DR5 monoclonal antibody alone or in combination with chemotherapy and/or radiation therapy in a human breast cancer model. Clinical Cancer Research. Sep. 1, 2003;9(10):3731-41.
Chothia C, Lesk AM. Canonical structures for the hypervariable regions of immunoglobulins. Journal of molecular biology. Aug. 20, 1987;196(4):901-17.
Clackson T, Hoogenboom HR. Making antibody fragments using phage display libraries. Nature. Aug. 15, 1991;352(6336):624-628.
Clynes R, Takechi Y, Moroi Y, Houghton A, Ravetch JV. Fc receptors are required in passive and active immunity to melanoma. Proceedings of the National Academy of Sciences. Jan. 20, 1998;95(2):652-6.
DiCesare, et al. (2013) Free Radic. Biol. Med. 61C:143-150.
Edelman GM, Cunningham BA, Gall WE, Gottlieb PD, Rutishauser U, Waxdal MJ. The covalent structure of an entire γG immunoglobulin molecule. Proceedings of the National Academy of Sciences. May 1, 1969;63(1):78-85.
Elbashir et al., 2001, Nature 411, 494-498.
Fenlon HM, Nunes DP, Schroy III PC, Barish MA, Clarke PD, Ferrucci JT, Waye JD, Lewis BS, Frankel A, Geller SA, Bruzzi JF. Screening for colorectal cancer. N Engl J Med. May 23, 2002;2002(346):1672-4.
Frier, et al (1986) PNAS 83: 9373-77.
Friesen C, Herr I, Krammer PH, Debatin KM. Involvement of the CD95 (APO-1/Fas) receptor/ligand system in drug-induced apoptosis in leukemia cells. Nature medicine. May 1, 1996;2(5):574-7.
Fulda et al., Oncogene (2006) 25, 4798-4811.
Fulda S, Los MJ, Friesen C, Debatin KM. Chemosensitivity of solid tumor cells in vitro is related to activation of the CD95 system. International journal of cancer. 1998;76(1):105-14.
Fulda S, Sieverts H, Friesen C, Herr I, Debatin KM. The CD95 (APO-1/Fas) system mediates drug-induced apoptosis in neuroblastoma cells. Cancer research. Sep. 1, 1997;57(17):3823-9.
GarinChesa PI, Sakamoto JU, Welt SY, Real F, Rettig W, Old L. Organ-specific expression of the colon cancer antigen A33, a cell surface target for antibody-based therapy. International journal of oncology. Sep. 1, 1996;9(3):465-71.
Gazzano-Santoro H, Ralph P, Ryskamp TC, Chen AB, Mukku VR. A non-radioactive complement-dependent cytotoxicity assay for anti-CD20 monoclonal antibody. Journal of immunological methods. Mar. 28, 1997;202(2):163-71.
Ghobrial IM, Witzig TE, Adjei AA. Targeting apoptosis pathways in cancer therapy. CA: a cancer journal for clinicians. May 1, 2005;55(3):178-94.
Gill DS, Damle NK. Biopharmaceutical drug discovery using novel protein scaffolds. Current opinion in biotechnology. Dec. 31, 2006;17(6):653-8.
Greenberg AS, Avila D, Hughes M, Hughes A. A new antigen receptor gene family that undergoes rearrangement and extensive somatic diversification in sharks. nature. Mar. 9, 1995;374(6518):168-173.
Haab BB, Porter A, Yue T, Li L, Scheiman J, Anderson MA, Barnes D, Schmidt CM, Feng Z, Simeone DM. Glycosylation variants of mucins and CEACAMs as candidate biomarkers for the diagnosis of pancreatic cystic neoplasms. Annals of surgery. May 2010;251(5):937.
Hall IM, Shankaranarayana GD, Noma KI, Ayoub N, Cohen A, Grewal SI. Establishment and maintenance of a heterochromatin domain. Science. Sep. 27, 2002;297(5590):2232-7.
Hamers-Casterman, et al. (1 93) Nature 363(6428): 446-8.
Hollinger et al., Proc. Natl. Acad. Sci. USA, 90:6444-6448 (1993).
Hollingsworth & Swanson (2004) Nature Reviews 4: 45-60.
Houghton JA, Harwood FG, Tillman DM. Thymineless death in colon carcinoma cells is mediated via fas signaling. Proceedings of the National Academy of Sciences. Jul. 22, 1997;94(15):8144-9.
Hutvagner and Zamore, 2002, Science 297, 2056-60.
Jones PT, Dear PH, Foote J, Neuberger MS, Winter G. Replacing the complementarity-determining regions in a human antibody with those from a mouse. Nature. May 29, 1986;321(6069):522-5.
Kashmiri SV, De Pascalis R, Gonzales NR, Schlom J. SDR grafting—a new approach to antibody humanization. Methods. May 31, 2005;36(1):25-34.

(56) References Cited

OTHER PUBLICATIONS

Knudson AG. Mutation and cancer: statistical study of retinoblastoma. Proceedings of the National Academy of Sciences. Apr. 1, 1971;68(4):820-3.

Jenuwein T. An RNA-guided pathway for the epigenome. Science. Sep. 27, 2002;297(5590):2215-8.

Kocer B, McKolanis J, Soran A. Humoral immune response to MUC5AC in patients with colorectal polyps and colorectal carcinoma. BMC gastroenterology. Jan. 12, 2006;6(1):4.

Kohler et al., Nature, 256:495 (1975).

Kolla V, Gonzales LW, Bailey NA, Wang P, Angampalli S, Godinez MH, Madesh M, Ballard PL. Carcinoembryonic cell adhesion molecule 6 in human lung: regulated expression of a multifunctional type II cell protein. American Journal of Physiology—Lung Cellular and Molecular Physiology. Jun. 1, 2009;296(6):L1019-30.

Kufe DW. Mucins in cancer: function, prognosis and therapy. Nature reviews. Cancer. Dec. 2009;9(12):874-885.

Laghi A, Iannaccone R, Carbone I, Catalano C, Di Giulio E, Schillaci A, Passariello R. Detection of colorectal lesions with virtual computed tomographic colonography. The American journal of surgery. Feb. 28, 2002;183(2):124-31.

Lau SK, Weiss LM, Chu PG. Differential expression of MUC1, MUC2, and MUC5AC in carcinomas of various sites: an immunohistochemical study. American journal of clinical pathology. Jul. 1, 2004;122(1):61-9.

Lund, et al. (2003) Cancer Gene Therapy 10: 365-376.

Marks JD, Hoogenboom HR, Bonnert TP, McCafferty J, Griffiths AD, Winter G. By-passing immunization: human antibodies from V-gene libraries displayed on phage. Journal of molecular biology. Dec. 5, 1991;222(3):581-97.

McManus MT, Petersen CP, Haines BB, Chen J, Sharp PA. Gene silencing using micro-RNA designed hairpins. Rna. Jun. 1, 2002;8(6):842-50.

Micheau O, Hammann A, Solary E, Dimanche-Boitrel MT. STAT-1-independent upregulation of FADD and procaspase-3 and -8 in cancer cells treated with cytotoxic drugs. Biochemical and biophysical research communications. Mar. 24, 1999;256(3):603-7.

Morrison SL, Johnson MJ, Herzenberg LA, Oi VT. Chimeric human antibody molecules: mouse antigen-binding domains with human constant region domains. Proceedings of the National Academy of Sciences. Nov. 1, 1984;81(21):6851-5.

Muller M, Strand S, Hug H, Heinemann EM, Walczak H, Hofmann WJ, Stremmel W, Krammer PH, Galle PR. Drug-induced apoptosis in hepatoma cells is mediated by the CD95 (APO-1/Fas) receptor/ligand system and involves activation of wild-type p53. Journal of Clinical Investigation. Feb. 1, 1997;99(3):403.

Nuttall SD, Krishnan UV, Hattarki M, De Gori R, Irving RA, Hudson PJ. Isolation of the new antigen receptor from wobbegong sharks, and use as a scaffold for the display of protein loop libraries. Molecular immunology. Aug. 31, 2001;38(4):313-26.

Otto K. Volumetric modulated arc therapy: IMRT in a single gantry arc. Medical physics. Jan. 1, 2008;35(1):310-7.

Plückthun A. Antibodies from *Escherichia coli*. InThe Pharmacology of Monoclonal Antibodies 1994 (pp. 269-315). Springer Berlin Heidelberg.

Presta LG. Antibody engineering. Current Opinion in Structural Biology. Aug. 1, 1992;2(4):593-6.

Ransohoff & Sandler (2002) N. Engl. J. Med. 346: 346 11.

Reinhart BJ, Bartel DP. Small RNAs correspond to centromere heterochromatic repeats. Science. Sep. 13, 2002;297(5588):1831.

Reinhart BJ, Weinstein EG, Rhoades MW, Bartel B, Bartel DP. MicroRNAs in plants. Genes & development Jul. 1, 2002;16(13):1616-26.

Riechmann L, Clark M, Waldmann H, Winter G. Reshaping human antibodies for therapy. Nature. Mar. 24, 1988;332(6162):323-7.

Shao H, Yoon TJ, Liong M, Weissleder R, Lee H. Magnetic nanoparticles for biomedical NMR-based diagnostics. Beilstein journal of nanotechnology. 2010;1:142-154.

Sias PE, Kotts CE, Vetterlein D, Shepard M, Wong WL. ELISA for quantitation of the extracellular domain of p185HER2 in biological fluids. Journal of immunological methods. Aug. 28, 1990;132(1):73-80.

Streltsov, et al. (2005) Protein Sci. 14(11): 2901-9.

Strickland LA, Ross J, Williams S, Ross S, Romero M, Spencer S, Erickson R, Sutcliffe J, Verbeke C, Polakis P, Van Bruggen N. Preclinical evaluation of carcinoembryonic cell adhesion molecule (CEACAM) 6 as potential therapy target for pancreatic adenocarcinoma. The Journal of pathology. Jul. 1, 2009;218(3):380-90.

Table 3 on p. 464 of Ravetch and Kinet, Annu Rev. Immunol. 9:457-92 (1991).

Turner, et al. (1987) J. Am. Chem. Soc. 109: 3783-85.

Volpe TA, Kidner C, Hall IM, Teng G, Grewal SI, Martienssen RA. Regulation of heterochromatic silencing and histone H3 lysine-9 methylation by RNAi. science. Sep. 13, 2002;297(5588):1833-7.

Wang Y, Engels IH, Knee DA, Nasoff M, Deveraux QL, Quon KC. Synthetic lethal targeting of MYC by activation of the DR5 death receptor pathway. Cancer cell. May 31, 2004;5(5):501-12.

Weinberg RA (1996) How cancer arises. Scientific America 275(3): 62-70.

Winawer SJ, Fletcher RH, Miller L, Godlee F, Stolar MH, Mulrow CD, Woolf SH, Glick SN, Ganiats TG, Bond JH, Rosen L. Colorectal cancer screening: clinical guidelines and rationale. Gastroenterology. Feb. 1, 1997;112(2):594-642.

Yan, D., Vicini, F., Wong, J., Martinez, A, Phys. Med. Biol. 42, 123-132, 1997.

Yu, C. X., Phys. Med. Biol. 40, 1435-1449, 1995.

Zapata G, Ridgway JB, Mordenti J, Osaka G, Wong WL, Bennett GL, Carter P. Engineering linear F (ab') 2 fragments for efficient production in *Escherichia coli* and enhanced antiproliferative activity. Protein Engineering, Design and Selection. Oct. 1, 1995;8(10):1057-62.

Zhang S, Zhang HS, Cordon-Cardo C, Ragupathi G, Livingston PO. Selection of tumor antigens as targets for immune attack using immunohistochemistry: protein antigens. Clinical cancer research. Nov. 1, 1998;4(11):2669-76.

\* cited by examiner

FIG. 1. NEO-101, NEO-201 and NEO-301 Antigen Expression in Human Cell Lines

| Cell line | Description | NEO-101 antigen | NEO-201 antigen | NEO-301 antigen |
|---|---|---|---|---|
| SW1116 | Colorectal adneocarcinoma cell line | negative | Positive | NA |
| SW480 | Colorectal adneocarcinoma cell line | negative | negative | NA |
| SW1463 | Colorectal adneocarcinoma cell line | negative | negative | NA |
| COLO205 | Colorectal adneocarcinoma cell line | Positive | negative | Positive |
| A549 | Lung carcinoma cell line | negative | negative | Negative |
| CALU-1 | Lung carcinoma cell line | negative | negative | NA |
| PANC-1 | Pancreatic carcinoma cell line | negative | negative | Positive |
| HT-29 | Colorectal adneocarcinoma cell line | Positive | Positive | Positive |
| LS174T | Colorectal adneocarcinoma cell line | Positive | Positive | Positive |
| CFPAC-1 | Pancreatic adneocarcinoma cell line | Positive | Positive | Negative |
| ASPC-1 | Pancreatic adneocarcinoma cell line | Positive | Positive | Positive |
| HCC4006 | Lung adneocarcinoma cell line | negative | Positive | NA |
| HCC827 | Lung adneocarcinoma cell line | negative | Positive | NA |
| H441 | Lung adneocarcinoma cell line | negative | Positive | Negative |
| SKLu-1 | Lung adneocarcinoma cell line | negative | negative | NA |
| H23 | Lung adneocarcinoma cell line | negative | negative | NA |
| H522 | Lung adneocarcinoma cell line | negative | negative | NA |
| HT-29 | Colorectal adenocarnoma cell line | Positive | Negative | Negative |
| HCT116 | Colorectal adenocarnoma cell line | Positive | Negative | Negative |
| Tov-21G | Ovarian cancer cell line | Negative | Negative | Negative |
| K562 | Myelogenous leukemia line | NA | Negative | Negative |
| SK-MES-1 | lung squamous carcinoma cell line | NA | Negative | Negative |
| MRC5 | Normal lung cell line | NA | Negative | NA |
| HTB-35 | Cervical squamous carcinoma cell line | NA | Negative | Negative |
| HTB-182 | lung squamous carcinoma cell line | NA | Positive | Negative |
| SW900 | lung squamous carcinoma cell line | NA | Positive | Negative |
| LnCap | prostate adenocarcinoma cell line | NA | Negative | Negative |

FIG. 1 (CONTINUED). NEO-101, NEO-201 and NEO-301 Antigen Expression in Human Cell Lines

| PC3 | prostate cancer cell line | NA | NA | Negative |
|---|---|---|---|---|
| MCF7 | breast cancer cell line | NA | NA | Negative |
| SW756 | Cervical squamous carcinoma cell line | NA | NA | Negative |

NA: not available.

FIG. 2. IHC Results from Cancer Tissue Microarrays

| | | NEO-101 (NPC-1C) | NEO-201 (h16C3) Positive Cases/Total Cases (% Reactivity) | NEO-301 (31.1) |
|---|---|---|---|---|
| Colon | Cancer | 105/172 (61%) | 139/163 (85%) | 60/90 (67%) |
| | Normal | 4/33 (12%) | 2/53 (4%) | 3/16 (19%) |
| Pancreas | Cancer | 30/98 (31%) | 54/63 (86%) | 36/63 (57%) |
| | Normal | 1/46 (2%) | 2/24 (8%) | 1/16 (6%) |
| Lung | Cancer | 3/53 (6%) | 46/75 (61%) | 72/129 (56%) |
| | Normal | 0/40 (0%) | 1/40 (3%) | 6/24 (25%) |
| Larynx | Cancer | 0/49 (0%) | n/a | n/a |
| | normal | 0/45 (0%) | n/a | n/a |
| Prostate | Cancer | 0/35 (0%) | 0/75 (0%) | 0/35 (0%) |
| | Normal | 0/30 (0%) | 0/39 (0%) | 0/35 (0%) |
| Esophagus | Cancer | 0/30 (0%) | n/a | 13/30 (43%) |
| | Normal | 0/30 (0%) | n/a | 6/30 (20%) |
| Uterus | Cancer | 36/88 (41%) | 45/88 (51%) | n/a |
| | Normal | 1/12 (8%) | 2/24 (8%) | n/a |
| Stomach | Cancer | 24/80 (30%) | n/a | n/a |
| | Normal | 1/16 (6%) | n/a | n/a |
| Skin | Cancer | n/a | 8/50 (16%) | n/a |
| | Normal | n/a | 0/8 (0%) | n/a |
| Breast | Cancer | n/a | 38/72 (53%) | 47/60 (78%) |
| | Normal | n/a | 0/12 (0%) | 5/45 (11%) |
| Ovary | Cancer | n/a | 16/129 (12%) | 9/86 (11%) |
| | normal | n/a | 2/24 (8%) | 1/16 (6%) | n/a: Not Available

FIG. 2 (continued). IHC Results from Cancer Tissue Microarrays

IHC Results from Paraffin Tissue Sections

|  |  | NEO-101(NPC-1C) | NEO-201(16C3) | NEO-301(31.1) |
|---|---|---|---|---|
|  |  | Positive Cases/Total Cases (% Reactivity) | | |
| Colon | Cancer | 86/99 (87%) | 88/94 (94%) | 49/94 (52%) |
|  | Normal | 4/33 (12%) | 3/27 (11%) | 1/4 (25%) |
| Pancreas | Cancer | 44/54 (82%) | 40/48 (83%) | 17/36 (47%) |
|  | Normal | 1/25 (4%) | 1/24 (4%) | 1/5 (20%) |
| Lung | Cancer | 4/6 (67%) | 9/10 (90%) | 1/5 (20%) |
|  | Normal | 0/3 (0%) | 0/3 (0%) | n/a |

FIG. 3. Summary of NEO-101, NEO-102 and NEO-201 IHC Results from normal colon and pancreatic paraffin tissues

|  | NEO-101 | NEO-102 | NEO-201 |
|---|---|---|---|
|  | Positive case#/total case# (%positivity) | | |
| Real normal colon | 2/19 (10%) | 2/19 (10%) | 2/19 (10%) |
| Normal ADJ to Colon Ca. | 3/14 (21%) | 3/14 (21%) | 1/14 (7%) |
| Real normal pancreatic | 0/17 (0%) | 0/17 (0%) | 0/17 (0%) |
| Normal ADJ to Pancreatic Ca | 0/5 (0%) | 0/5 (0%) | 0/5 (0%) |

SEQUENCE LISTING

```
<160> NUMBER OF SEQ ID NOS: 130

<210> SEQ ID NO 1
<211> LENGTH: 5030
<212> TYPE: PRT
<213> ORGANISM: Homo sapiens

<400> SEQUENCE: 1

Met Ser Val Gly Arg Arg Lys Leu Ala Leu Leu Trp Ala Leu Ala Leu
1               5                   10                  15

Ala Leu Ala Cys Thr Arg His Thr Gly His Ala Gln Asp Gly Ser Ser
            20                  25                  30

Glu Ser Ser Tyr Lys His His Pro Ala Leu Ser Pro Ile Ala Arg Gly
        35                  40                  45

Pro Ser Gly Val Pro Leu Arg Gly Ala Thr Val Phe Pro Ser Leu Arg
    50                  55                  60

Thr Ile Pro Val Val Arg Ala Ser Asn Pro Ala His Asn Gly Arg Val
65                  70                  75                  80

Cys Ser Thr Trp Gly Ser Phe His Tyr Lys Thr Phe Asp Gly Asp Val
                85                  90                  95

Phe Arg Phe Pro Gly Leu Cys Asn Tyr Val Phe Ser Glu His Cys Gly
                100                 105                 110

Ala Ala Tyr Glu Asp Phe Asn Ile Gln Leu Arg Arg Ser Gln Glu Ser
            115                 120                 125

Ala Ala Pro Thr Leu Ser Arg Val Leu Met Lys Val Asp Gly Val Val
        130                 135                 140

Ile Gln Leu Thr Lys Gly Ser Val Leu Val Asn Gly His Pro Val Leu
145                 150                 155                 160

Leu Pro Phe Ser Gln Ser Gly Val Leu Ile Gln Gln Ser Ser Ser Tyr
                165                 170                 175
```

-continued

Thr Lys Val Glu Ala Arg Leu Gly Leu Val Leu Met Trp Asn His Asp
        180                 185                 190

Asp Ser Leu Leu Leu Glu Leu Asp Thr Lys Tyr Ala Asn Lys Thr Cys
        195                 200                 205

Gly Leu Cys Gly Asp Phe Asn Gly Met Pro Val Val Ser Glu Leu Leu
        210                 215                 220

Ser His Asn Thr Lys Leu Thr Pro Met Glu Phe Gly Asn Leu Gln Lys
225                 230                 235                 240

Met Asp Asp Pro Thr Glu Gln Cys Gln Asp Pro Val Pro Glu Pro Pro
                245                 250                 255

Arg Asn Cys Ser Thr Gly Phe Gly Ile Cys Glu Glu Leu Leu His Gly
                260                 265                 270

Gln Leu Phe Ser Gly Cys Val Ala Leu Val Asp Val Gly Ser Tyr Leu
            275                 280                 285

Glu Ala Cys Arg Gln Asp Leu Cys Phe Cys Glu Asp Thr Asp Leu Leu
        290                 295                 300

Ser Cys Val Cys His Thr Leu Ala Glu Tyr Ser Arg Gln Cys Thr His
305                 310                 315                 320

Ala Gly Gly Leu Pro Gln Asp Trp Arg Gly Pro Asp Phe Cys Pro Gln
                325                 330                 335

Lys Cys Pro Asn Asn Met Gln Tyr His Glu Cys Arg Ser Pro Cys Ala
                340                 345                 350

Asp Thr Cys Ser Asn Gln Glu His Ser Arg Ala Cys Glu Asp His Cys
            355                 360                 365

Val Ala Gly Cys Phe Cys Pro Glu Gly Thr Val Leu Asp Asp Ile Gly
        370                 375                 380

Gln Thr Gly Cys Val Pro Val Ser Lys Cys Ala Cys Val Tyr Asn Gly
385                 390                 395                 400

Ala Ala Tyr Ala Pro Gly Ala Thr Tyr Ser Thr Asp Cys Thr Asn Cys
                405                 410                 415

Thr Cys Ser Gly Gly Arg Trp Ser Cys Gln Glu Val Pro Cys Pro Asp
                420                 425                 430

Thr Cys Ser Val Leu Gly Gly Ala His Phe Ser Thr Phe Asp Gly Lys
            435                 440                 445

Gln Tyr Thr Val His Gly Asp Cys Ser Tyr Val Leu Thr Lys Pro Cys
        450                 455                 460

Asp Ser Ser Ala Phe Thr Val Leu Ala Glu Leu Arg Arg Cys Gly Leu
465                 470                 475                 480

Thr Asp Ser Glu Thr Cys Leu Lys Ser Val Thr Leu Ser Leu Asp Gly
                485                 490                 495

Ala Gln Thr Val Val Ile Lys Ala Ser Gly Glu Val Phe Leu Asn
                500                 505                 510

Gln Ile Tyr Thr Gln Leu Pro Ile Ser Ala Ala Asn Val Thr Ile Phe
        515                 520                 525

Arg Pro Ser Thr Phe Phe Ile Ile Ala Gln Thr Ser Leu Gly Leu Gln
        530                 535                 540

Leu Asn Leu Gln Pro Val Pro Thr Met Gln Leu Phe Met Gln Leu Ala
545                 550                 555                 560

Pro Lys Leu Arg Gly Gln Thr Cys Gly Leu Cys Gly Asn Phe Asn Ser
                565                 570                 575

Ile Gln Ala Asp Asp Phe Arg Thr Leu Ser Gly Val Val Glu Ala Thr
                580                 585                 590

```
Ala Ala Ala Phe Phe Asn Thr Phe Lys Thr Gln Ala Cys Pro Asn
            595                 600                 605

Ile Arg Asn Ser Phe Glu Asp Pro Cys Ser Leu Ser Val Glu Asn Glu
610                 615                 620

Lys Tyr Ala Gln His Trp Cys Ser Gln Leu Thr Asp Ala Asp Gly Pro
625                 630                 635                 640

Phe Gly Arg Cys His Ala Ala Val Lys Pro Gly Thr Tyr Tyr Ser Asn
                645                 650                 655

Cys Val Phe Asp Thr Cys Asn Cys Glu Arg Ser Glu Asp Cys Leu Cys
            660                 665                 670

Ala Ala Leu Ser Ser Tyr Val His Ala Cys Ala Ala Lys Gly Val Gln
        675                 680                 685

Leu Gly Gly Trp Arg Asp Gly Val Cys Thr Lys Pro Met Thr Thr Cys
    690                 695                 700

Pro Lys Ser Met Thr Tyr His Tyr His Val Ser Thr Cys Gln Pro Thr
705                 710                 715                 720

Cys Arg Ser Leu Ser Glu Gly Asp Ile Thr Cys Ser Val Gly Phe Ile
                725                 730                 735

Pro Val Asp Gly Cys Ile Cys Pro Lys Gly Thr Phe Leu Asp Asp Thr
            740                 745                 750

Gly Lys Cys Val Gln Ala Ser Asn Cys Pro Cys Tyr His Arg Gly Ser
        755                 760                 765

Met Ile Pro Asn Gly Glu Ser Val His Asp Ser Gly Ala Ile Cys Thr
    770                 775                 780

Cys Thr His Gly Lys Leu Ser Cys Ile Gly Gly Gln Ala Pro Ala Pro
785                 790                 795                 800

Val Cys Ala Ala Pro Met Val Phe Phe Asp Cys Arg Asn Ala Thr Pro
                805                 810                 815

Gly Asp Thr Gly Ala Gly Cys Gln Lys Ser Cys His Thr Leu Asp Met
            820                 825                 830

Thr Cys Tyr Ser Pro Gln Cys Val Pro Gly Cys Val Cys Pro Asp Gly
        835                 840                 845

Leu Val Ala Asp Gly Glu Gly Gly Cys Ile Thr Ala Glu Asp Cys Pro
    850                 855                 860

Cys Val His Asn Glu Ala Ser Tyr Arg Ala Gly Gln Thr Ile Arg Val
865                 870                 875                 880

Gly Cys Asn Thr Cys Thr Cys Asp Ser Arg Met Trp Arg Cys Thr Asp
                885                 890                 895

Asp Pro Cys Leu Ala Thr Cys Ala Val Tyr Gly Asp Gly His Tyr Leu
            900                 905                 910

Thr Phe Asp Gly Gln Ser Tyr Ser Phe Asn Gly Asp Cys Glu Tyr Thr
        915                 920                 925

Leu Val Gln Asn His Cys Gly Gly Lys Asp Ser Thr Gln Asp Ser Phe
    930                 935                 940

Arg Val Val Thr Glu Asn Val Pro Cys Gly Thr Thr Gly Thr Thr Cys
945                 950                 955                 960

Ser Lys Ala Ile Lys Ile Phe Leu Gly Gly Phe Glu Leu Lys Leu Ser
                965                 970                 975

His Gly Lys Val Glu Val Ile Gly Thr Asp Glu Ser Gln Glu Val Pro
            980                 985                 990

Tyr Thr Ile Gln Gln Met Gly Ile Tyr Leu Val Val Asp Thr Asp Ile
        995                 1000                1005

Gly Leu Val Leu Leu Trp Asp Lys Lys Thr Ser Ile Phe Ile Asn
```

-continued

```
              1010                1015                1020
Leu Ser Pro Glu Phe Lys Gly Arg Val Cys Gly Leu Cys Gly Asn
    1025                1030                1035

Phe Asp Asp Ile Ala Val Asn Asp Phe Ala Thr Arg Ser Arg Ser
    1040                1045                1050

Val Val Gly Asp Val Leu Glu Phe Gly Asn Ser Trp Lys Leu Ser
    1055                1060                1065

Pro Ser Cys Pro Asp Ala Leu Ala Pro Lys Asp Pro Cys Thr Ala
    1070                1075                1080

Asn Pro Phe Arg Lys Ser Trp Ala Gln Lys Gln Cys Ser Ile Leu
    1085                1090                1095

His Gly Pro Thr Phe Ala Ala Cys His Ala His Val Glu Pro Ala
    1100                1105                1110

Arg Tyr Tyr Glu Ala Cys Val Asn Asp Ala Cys Ala Cys Asp Ser
    1115                1120                1125

Gly Gly Asp Cys Glu Cys Phe Cys Thr Ala Val Ala Ala Tyr Ala
    1130                1135                1140

Gln Ala Cys His Glu Val Gly Leu Cys Val Cys Leu Arg Thr Pro
    1145                1150                1155

Ser Ile Cys Pro Leu Phe Cys Asp Tyr Tyr Asn Pro Glu Gly Gln
    1160                1165                1170

Cys Glu Trp His Tyr Gln Pro Cys Gly Val Pro Cys Leu Arg Thr
    1175                1180                1185

Cys Arg Asn Pro Arg Gly Asp Cys Leu Arg Asp Val Arg Gly Leu
    1190                1195                1200

Glu Gly Cys Tyr Pro Lys Cys Pro Pro Glu Ala Pro Ile Phe Asp
    1205                1210                1215

Glu Asp Lys Met Gln Cys Val Ala Thr Cys Pro Thr Pro Pro Leu
    1220                1225                1230

Pro Pro Arg Cys His Val His Gly Lys Ser Tyr Arg Pro Gly Ala
    1235                1240                1245

Val Val Pro Ser Asp Lys Asn Cys Gln Ser Cys Leu Cys Thr Glu
    1250                1255                1260

Arg Gly Val Glu Cys Thr Tyr Lys Ala Glu Ala Cys Val Cys Thr
    1265                1270                1275

Tyr Asn Gly Gln Arg Phe His Pro Gly Asp Val Ile Tyr His Thr
    1280                1285                1290

Thr Asp Gly Thr Gly Gly Cys Ile Ser Ala Arg Cys Gly Ala Asn
    1295                1300                1305

Gly Thr Ile Glu Arg Arg Val Tyr Pro Cys Ser Pro Thr Thr Pro
    1310                1315                1320

Val Pro Pro Thr Thr Phe Ser Phe Ser Thr Pro Pro Leu Val Val
    1325                1330                1335

Ser Ser Thr His Thr Pro Ser Asn Gly Pro Ser Ser Ala His Thr
    1340                1345                1350

Gly Pro Pro Ser Ser Ala Trp Pro Thr Thr Ala Gly Thr Ser Pro
    1355                1360                1365

Arg Thr Arg Leu Pro Thr Ala Ser Ala Ser Leu Pro Pro Val Cys
    1370                1375                1380

Gly Glu Lys Cys Leu Trp Ser Pro Trp Met Asp Val Ser Arg Pro
    1385                1390                1395

Gly Arg Gly Thr Asp Ser Gly Asp Phe Asp Thr Leu Glu Asn Leu
    1400                1405                1410
```

```
Arg Ala His Gly Tyr Arg Val Cys Glu Ser Pro Arg Ser Val Glu
1415                 1420                1425

Cys Arg Ala Glu Asp Ala Pro Gly Val Pro Leu Arg Ala Leu Gly
1430                 1435                1440

Gln Arg Val Gln Cys Ser Pro Asp Val Gly Leu Thr Cys Arg Asn
1445                 1450                1455

Arg Glu Gln Ala Ser Gly Leu Cys Tyr Asn Tyr Gln Ile Arg Val
1460                 1465                1470

Gln Cys Cys Thr Pro Leu Pro Cys Ser Thr Ser Ser Pro Ala
1475                 1480                1485

Gln Thr Thr Pro Pro Thr Thr Ser Lys Thr Thr Glu Thr Arg Ala
1490                 1495                1500

Ser Gly Ser Ser Ala Pro Ser Ser Thr Pro Gly Thr Val Ser Leu
1505                 1510                1515

Ser Thr Ala Arg Thr Thr Pro Ala Pro Gly Thr Ala Thr Ser Val
1520                 1525                1530

Lys Lys Thr Phe Ser Thr Pro Ser Pro Pro Val Pro Ala Thr
1535                 1540                1545

Ser Thr Ser Ser Met Ser Thr Thr Ala Pro Gly Thr Ser Val Val
1550                 1555                1560

Ser Ser Lys Pro Thr Pro Thr Glu Pro Ser Thr Ser Cys Leu
1565                 1570                1575

Gln Glu Leu Cys Thr Trp Thr Glu Trp Ile Asp Gly Ser Tyr Pro
1580                 1585                1590

Ala Pro Gly Ile Asn Gly Gly Asp Phe Asp Thr Phe Gln Asn Leu
1595                 1600                1605

Arg Asp Glu Gly Tyr Thr Phe Cys Glu Ser Pro Arg Ser Val Gln
1610                 1615                1620

Cys Arg Ala Glu Ser Phe Pro Asn Thr Pro Leu Ala Asp Leu Gly
1625                 1630                1635

Gln Asp Val Ile Cys Ser His Thr Glu Gly Leu Ile Cys Leu Asn
1640                 1645                1650

Lys Asn Gln Leu Pro Pro Ile Cys Tyr Asn Tyr Glu Ile Arg Ile
1655                 1660                1665

Gln Cys Cys Glu Thr Val Asn Val Cys Arg Asp Ile Thr Arg Leu
1670                 1675                1680

Pro Lys Thr Val Ala Thr Thr Arg Pro Thr Pro His Pro Thr Gly
1685                 1690                1695

Ala Gln Thr Gln Thr Thr Phe Thr Thr His Met Pro Ser Ala Ser
1700                 1705                1710

Thr Glu Gln Pro Thr Ala Thr Ser Arg Gly Gly Pro Thr Ala Thr
1715                 1720                1725

Ser Val Thr Gln Gly Thr His Thr Thr Leu Val Thr Arg Asn Cys
1730                 1735                1740

His Pro Arg Cys Thr Trp Thr Lys Trp Phe Asp Val Asp Phe Pro
1745                 1750                1755

Ser Pro Gly Pro His Gly Gly Asp Lys Glu Thr Tyr Asn Asn Ile
1760                 1765                1770

Ile Arg Ser Gly Glu Lys Ile Cys Arg Arg Pro Glu Glu Ile Thr
1775                 1780                1785

Arg Val Gln Cys Arg Ala Lys Ser His Pro Glu Val Ser Ile Glu
1790                 1795                1800
```

```
His Leu Gly Gln Val Val Gln Cys Ser Arg Glu Glu Gly Leu Val
    1805                1810                1815

Cys Arg Asn Gln Asp Gln Gln Gly Pro Phe Lys Met Cys Leu Asn
    1820                1825                1830

Tyr Glu Val Arg Val Leu Cys Cys Glu Thr Pro Arg Gly Cys His
    1835                1840                1845

Met Thr Ser Thr Pro Gly Ser Thr Ser Ser Pro Ala Gln Thr
    1850                1855                1860

Thr Pro Ser Thr Thr Ser Lys Thr Thr Glu Ile Gln Ala Ser Gly
    1865                1870                1875

Ser Ser Ala Pro Ser Ser Thr Pro Gly Thr Val Ser Leu Ser Thr
    1880                1885                1890

Ala Arg Thr Thr Pro Ala Pro Gly Thr Ala Thr Ser Val Lys Lys
    1895                1900                1905

Thr Phe Ser Thr Pro Ser Pro Pro Val Pro Ala Thr Ser Thr
    1910                1915                1920

Ser Ser Met Ser Thr Thr Ala Pro Gly Thr Ser Val Val Ser Ser
    1925                1930                1935

Lys Pro Thr Pro Thr Glu Pro Ser Thr Ser Ser Cys Leu Gln Glu
    1940                1945                1950

Leu Cys Thr Trp Thr Glu Trp Ile Asp Gly Ser Tyr Pro Ala Pro
    1955                1960                1965

Gly Ile Asn Gly Gly Asp Phe Asp Thr Phe Gln Asn Leu Arg Asp
    1970                1975                1980

Glu Gly Tyr Thr Phe Cys Glu Ser Pro Arg Ser Val Gln Cys Arg
    1985                1990                1995

Ala Glu Ser Phe Pro Asn Thr Pro Leu Gly Arg Leu Gly Gln Asp
    2000                2005                2010

Val Ile Cys Ser His Thr Glu Gly Leu Ile Cys Leu Asn Lys Asn
    2015                2020                2025

Gln Leu Pro Pro Ile Cys Tyr Asn Tyr Glu Ile Arg Ile Gln Cys
    2030                2035                2040

Cys Glu Thr Val Asn Val Cys Arg Asp Ile Thr Arg Pro Pro Lys
    2045                2050                2055

Thr Val Ala Thr Thr Arg Pro Thr Pro His Pro Thr Gly Ala Gln
    2060                2065                2070

Thr Gln Thr Thr Phe Thr Thr His Met Pro Ser Ala Ser Thr Glu
    2075                2080                2085

Gln Pro Thr Ala Thr Ser Arg Gly Gly Pro Thr Ala Thr Ser Val
    2090                2095                2100

Thr Gln Gly Thr His Thr Thr Pro Val Thr Arg Asn Cys His Pro
    2105                2110                2115

Arg Cys Thr Trp Thr Thr Trp Phe Asp Val Asp Phe Pro Ser Pro
    2120                2125                2130

Gly Pro His Gly Gly Asp Lys Glu Thr Tyr Asn Asn Ile Ile Arg
    2135                2140                2145

Ser Gly Glu Lys Ile Cys Arg Arg Pro Glu Glu Ile Thr Arg Leu
    2150                2155                2160

Gln Cys Arg Ala Lys Ser His Pro Glu Val Ser Ile Glu His Leu
    2165                2170                2175

Gly Gln Val Val Gln Cys Ser Arg Glu Glu Gly Leu Val Cys Arg
    2180                2185                2190

Asn Gln Asp Gln Gln Gly Pro Phe Lys Met Cys Leu Asn Ile Glu
```

-continued

```
            2195                2200                2205
Val Arg Val Leu Cys Cys Glu Thr Pro Lys Gly Cys Pro Val Thr
    2210                2215                2220

Ser Thr Pro Val Thr Ala Pro Ser Thr Pro Ser Gly Arg Ala Ile
    2225                2230                2235

Ser Pro Thr Gln Ser Thr Ser Ser Trp Gln Lys Ser Arg Thr Thr
    2240                2245                2250

Thr Leu Val Thr Thr Ser Thr Thr Ser Thr Pro Gln Thr Ser Thr
    2255                2260                2265

Thr Tyr Ala His Thr Thr Ser Thr Thr Ser Ala Pro Thr Ala Arg
    2270                2275                2280

Thr Thr Ser Ala Pro Thr Thr Ser Thr Thr Ser Val Pro Thr Thr
    2285                2290                2295

Ser Thr Ile Ser Gly Pro Lys Thr Thr Pro Ser Pro Val Pro Thr
    2300                2305                2310

Thr Ser Thr Thr Ser Ala Ala Thr Thr Ser Thr Ile Ser Ala Pro
    2315                2320                2325

Thr Thr Ser Thr Thr Ser Val Pro Gly Thr Thr Pro Ser Pro Val
    2330                2335                2340

Leu Thr Thr Ser Thr Thr Ser Ala Pro Thr Thr Arg Thr Thr Ser
    2345                2350                2355

Ala Ser Pro Ala Gly Thr Thr Ser Gly Pro Gly Asn Thr Pro Ser
    2360                2365                2370

Pro Val Pro Thr Thr Ser Thr Ile Ser Ala Pro Thr Thr Ser Ile
    2375                2380                2385

Thr Ser Ala Pro Thr Thr Ser Thr Thr Ser Ala Pro Thr Ser Ser
    2390                2395                2400

Thr Thr Ser Gly Pro Gly Thr Thr Pro Ser Pro Val Pro Thr Thr
    2405                2410                2415

Ser Ile Thr Ser Ala Pro Thr Thr Ser Thr Thr Ser Ala Pro Thr
    2420                2425                2430

Thr Ser Thr Thr Ser Ala Pro Thr Thr Ser Thr Thr Ser Ala Pro
    2435                2440                2445

Thr Thr Ser Thr Thr Ser Ala Pro Thr Thr Ser Thr Thr Ser Thr
    2450                2455                2460

Pro Thr Ser Ser Thr Thr Ser Thr Pro Gln Thr Ser Thr Thr Ser
    2465                2470                2475

Ala Ser Thr Thr Ser Ile Ser Gly Pro Gly Thr Thr Pro Ser
    2480                2485                2490

Pro Val Pro Thr Thr Ser Thr Ser Ala Pro Thr Thr Ser Thr
    2495                2500                2505

Thr Ser Ala Ala Thr Thr Ser Thr Ile Ser Ala Pro Thr Thr Ser
    2510                2515                2520

Thr Thr Ser Ala Pro Thr Thr Ser Thr Thr Ser Ala Ser Thr Ala
    2525                2530                2535

Ser Lys Thr Ser Gly Leu Gly Thr Thr Pro Ser Pro Ile Pro Thr
    2540                2545                2550

Thr Ser Thr Thr Ser Pro Pro Thr Thr Ser Thr Thr Ser Ala Ser
    2555                2560                2565

Thr Ala Ser Lys Thr Ser Gly Pro Gly Thr Thr Pro Ser Pro Val
    2570                2575                2580

Pro Thr Thr Ser Thr Ile Phe Ala Pro Arg Thr Ser Thr Thr Ser
    2585                2590                2595
```

```
Ala Ser Thr Thr Ser Thr Thr Pro Gly Pro Gly Thr Thr Pro Ser
    2600                2605                2610

Pro Val Pro Thr Thr Ser Thr Ala Ser Val Ser Lys Thr Ser Thr
    2615                2620                2625

Ser His Val Ser Ile Ser Lys Thr Thr His Ser Gln Pro Val Thr
    2630                2635                2640

Arg Asp Cys His Leu Arg Cys Thr Trp Thr Lys Trp Phe Asp Val
    2645                2650                2655

Asp Phe Pro Ser Pro Gly Pro His Gly Gly Asp Lys Glu Thr Tyr
    2660                2665                2670

Asn Asn Ile Ile Arg Ser Gly Glu Lys Ile Cys Arg Arg Pro Glu
    2675                2680                2685

Glu Ile Thr Arg Leu Gln Cys Arg Ala Glu Ser His Pro Glu Val
    2690                2695                2700

Ser Ile Glu His Leu Gly Gln Val Val Gln Cys Ser Arg Glu Glu
    2705                2710                2715

Gly Leu Val Cys Arg Asn Gln Asp Gln Gly Pro Phe Lys Met
    2720                2725                2730

Cys Leu Asn Tyr Glu Val Arg Val Leu Cys Cys Glu Thr Pro Lys
    2735                2740                2745

Gly Cys Pro Val Thr Ser Thr Pro Val Thr Ala Pro Ser Thr Pro
    2750                2755                2760

Ser Gly Arg Ala Thr Ser Pro Thr Gln Ser Thr Ser Ser Trp Gln
    2765                2770                2775

Lys Ser Arg Thr Thr Thr Leu Val Thr Thr Ser Thr Thr Ser Thr
    2780                2785                2790

Pro Gln Thr Ser Thr Thr Ser Ala Pro Thr Thr Ser Thr Thr Ser
    2795                2800                2805

Ala Pro Thr Thr Ser Thr Thr Ser Ala Pro Thr Thr Ser Thr Thr
    2810                2815                2820

Ser Thr Pro Gln Thr Ser Ile Ser Ser Ala Pro Thr Ser Ser Thr
    2825                2830                2835

Thr Ser Ala Pro Thr Ser Ser Thr Ile Ser Ala Arg Thr Thr Ser
    2840                2845                2850

Ile Ile Ser Ala Pro Thr Ser Thr Thr Ser Ser Pro Thr Thr
    2855                2860                2865

Ser Thr Thr Ser Ala Thr Thr Thr Ser Thr Thr Ser Ala Pro Thr
    2870                2875                2880

Ser Ser Thr Thr Ser Thr Pro Gln Thr Ser Lys Thr Ser Ala Ala
    2885                2890                2895

Thr Ser Ser Thr Thr Ser Ser Gly Thr Thr Pro Ser Pro Val
    2900                2905                2910

Thr Thr Thr Ser Thr Ala Ser Val Ser Lys Thr Ser Thr Ser His
    2915                2920                2925

Val Ser Val Ser Lys Thr Thr His Ser Gln Pro Val Thr Arg Asp
    2930                2935                2940

Cys His Pro Arg Cys Thr Trp Thr Lys Trp Phe Asp Val Asp Phe
    2945                2950                2955

Pro Ser Pro Gly Pro His Gly Gly Asp Lys Glu Thr Tyr Asn Asn
    2960                2965                2970

Ile Ile Arg Ser Gly Glu Lys Ile Cys Arg Arg Pro Gln Glu Ile
    2975                2980                2985
```

```
Thr Arg Leu Gln Cys Arg Ala Lys Ser His Pro Glu Val Ser Ile
    2990                2995                3000

Glu His Leu Gly Gln Val Val Gln Cys Ser Arg Glu Glu Gly Leu
    3005                3010                3015

Val Cys Arg Asn Gln Asp Gln Gln Gly Pro Phe Lys Met Cys Leu
    3020                3025                3030

Asn Tyr Glu Val Arg Val Leu Cys Cys Glu Thr Pro Lys Gly Cys
    3035                3040                3045

Pro Val Thr Ser Thr Ser Val Thr Ala Pro Ser Pro Leu Val Gly
    3050                3055                3060

Glu Pro Pro Ala Gln Thr Gln Ser Thr Ser Ser Trp Gln Lys Ser
    3065                3070                3075

Arg Thr Thr Thr Leu Val Thr Ser Ser Ile Thr Ser Thr Thr Gln
    3080                3085                3090

Thr Ser Thr Thr Ser Ala Pro Thr Thr Ser Thr Thr Pro Ala Ser
    3095                3100                3105

Ile Pro Ser Thr Thr Ser Ala Pro Thr Thr Ser Thr Thr Ser Ala
    3110                3115                3120

Pro Thr Thr Ser Thr Thr Ser Ala Pro Thr Thr Ser Thr Thr Ser
    3125                3130                3135

Thr Pro Gln Thr Thr Thr Ser Ser Ala Pro Thr Ser Ser Thr Thr
    3140                3145                3150

Ser Ala Pro Thr Thr Ser Thr Ile Ser Ala Pro Thr Thr Ser Thr
    3155                3160                3165

Ile Ser Ala Pro Thr Thr Ser Thr Thr Ser Ala Pro Thr Ala Ser
    3170                3175                3180

Thr Thr Ser Ala Pro Thr Ser Thr Ser Ser Ala Pro Thr Thr Asn
    3185                3190                3195

Thr Thr Ser Ala Pro Thr Thr Ser Thr Thr Ser Ala Pro Ile Thr
    3200                3205                3210

Ser Thr Ile Ser Ala Pro Thr Thr Ser Thr Thr Ser Thr Pro Gln
    3215                3220                3225

Thr Ser Thr Ile Ser Ser Pro Thr Thr Ser Thr Thr Pro Thr Pro
    3230                3235                3240

Gln Thr Ser Thr Thr Ser Ser Pro Thr Thr Ser Thr Thr Ser Ala
    3245                3250                3255

Pro Thr Thr Ser Thr Thr Ser Ala Pro Thr Thr Ser Thr Thr Ser
    3260                3265                3270

Thr Pro Gln Thr Ser Ile Ser Ser Ala Pro Thr Ser Ser Thr Thr
    3275                3280                3285

Ser Ala Pro Thr Ala Ser Thr Ile Ser Ala Pro Thr Thr Ser Thr
    3290                3295                3300

Thr Ser Phe His Thr Thr Ser Thr Thr Ser Pro Pro Thr Ser Ser
    3305                3310                3315

Thr Ser Ser Thr Pro Gln Thr Ser Lys Thr Ser Ala Ala Thr Ser
    3320                3325                3330

Ser Thr Thr Ser Gly Ser Gly Thr Thr Pro Ser Pro Val Pro Thr
    3335                3340                3345

Thr Ser Thr Ala Ser Val Ser Lys Thr Ser Thr Ser His Val Ser
    3350                3355                3360

Val Ser Lys Thr Thr His Ser Gln Pro Val Thr Arg Asp Cys His
    3365                3370                3375

Pro Arg Cys Thr Trp Thr Lys Trp Phe Asp Val Asp Phe Pro Ser
```

```
                    3380              3385              3390
Pro  Gly  Pro  His  Gly  Gly  Asp  Lys  Glu  Thr  Tyr  Asn  Asn  Ile  Ile
          3395              3400              3405

Arg  Ser  Gly  Glu  Lys  Ile  Cys  Arg  Arg  Pro  Glu  Glu  Ile  Thr  Arg
          3410              3415              3420

Leu  Gln  Cys  Arg  Ala  Glu  Ser  His  Pro  Glu  Val  Ser  Ile  Glu  His
          3425              3430              3435

Leu  Gly  Gln  Val  Val  Gln  Cys  Ser  Arg  Glu  Glu  Gly  Leu  Val  Cys
          3440              3445              3450

Arg  Asn  Gln  Asp  Gln  Gln  Gly  Pro  Phe  Lys  Met  Cys  Leu  Asn  Tyr
          3455              3460              3465

Glu  Val  Arg  Val  Leu  Cys  Cys  Glu  Thr  Pro  Lys  Gly  Cys  Pro  Val
          3470              3475              3480

Thr  Ser  Thr  Pro  Val  Thr  Ala  Pro  Ser  Thr  Pro  Ser  Gly  Arg  Ala
          3485              3490              3495

Thr  Ser  Pro  Thr  Gln  Ser  Thr  Ser  Ser  Trp  Gln  Lys  Ser  Arg  Thr
          3500              3505              3510

Thr  Thr  Leu  Val  Thr  Thr  Ser  Thr  Thr  Ser  Thr  Pro  Gln  Thr  Ser
          3515              3520              3525

Thr  Thr  Ser  Ala  Pro  Thr  Thr  Ser  Thr  Ile  Pro  Ala  Ser  Thr  Pro
          3530              3535              3540

Ser  Thr  Thr  Ser  Ala  Pro  Thr  Thr  Ser  Thr  Thr  Ser  Ala  Pro  Thr
          3545              3550              3555

Thr  Ser  Thr  Thr  Ser  Ala  Pro  Thr  His  Arg  Thr  Thr  Ser  Gly  Pro
          3560              3565              3570

Thr  Thr  Ser  Thr  Thr  Leu  Ala  Pro  Thr  Thr  Ser  Thr  Thr  Ser  Ala
          3575              3580              3585

Pro  Thr  Thr  Ser  Thr  Asn  Ser  Ala  Pro  Thr  Thr  Ser  Thr  Ile  Ser
          3590              3595              3600

Ala  Ser  Thr  Thr  Ser  Thr  Ile  Ser  Ala  Pro  Thr  Thr  Ser  Thr  Ile
          3605              3610              3615

Ser  Ser  Pro  Thr  Ser  Ser  Thr  Ser  Thr  Pro  Gln  Thr  Ser  Lys
          3620              3625              3630

Thr  Ser  Ala  Ala  Thr  Ser  Ser  Thr  Thr  Ser  Gly  Ser  Gly  Thr  Thr
          3635              3640              3645

Pro  Ser  Pro  Val  Pro  Thr  Thr  Ser  Thr  Thr  Ser  Ala  Ser  Thr  Thr
          3650              3655              3660

Ser  Thr  Thr  Ser  Ala  Pro  Thr  Ser  Thr  Thr  Ser  Gly  Pro  Gly
          3665              3670              3675

Thr  Thr  Pro  Ser  Pro  Val  Pro  Ser  Thr  Ser  Ile  Thr  Ser  Ala  Ala
          3680              3685              3690

Thr  Thr  Ser  Thr  Thr  Ser  Ala  Pro  Thr  Thr  Arg  Thr  Thr  Ser  Ala
          3695              3700              3705

Pro  Thr  Ser  Ser  Met  Thr  Ser  Gly  Pro  Gly  Thr  Thr  Pro  Ser  Pro
          3710              3715              3720

Val  Pro  Thr  Thr  Ser  Thr  Thr  Ser  Ala  Pro  Thr  Thr  Ser  Thr  Thr
          3725              3730              3735

Ser  Gly  Pro  Gly  Thr  Thr  Pro  Ser  Pro  Val  Pro  Thr  Thr  Ser  Thr
          3740              3745              3750

Thr  Ser  Ala  Pro  Ile  Thr  Ser  Thr  Thr  Ser  Gly  Pro  Gly  Ser  Thr
          3755              3760              3765

Pro  Ser  Pro  Val  Pro  Thr  Thr  Ser  Thr  Thr  Ser  Ala  Pro  Thr  Thr
          3770              3775              3780
```

```
Ser Thr Thr Ser Ala Ser Thr Ala Ser Thr Ser Gly Pro Thr
    3785                3790            3795

Thr Ser Thr Thr Ser Ala Ser Thr Thr Ser Thr Ile Ser Pro Leu
    3800                3805            3810

Thr Thr Ser Thr Thr Ser Ala Pro Ile Thr Ser Met Pro Ser Gly
    3815                3820            3825

Pro Gly Thr Thr Pro Ser Pro Val Pro Thr Thr Ser Thr Thr Ser
    3830                3835            3840

Ala Pro Thr Thr Ser Thr Thr Ser Gly Pro Gly Thr Thr Pro Ser
    3845                3850            3855

Pro Val Pro Thr Thr Ser Thr Thr Ser Ala Pro Thr Thr Ser Thr
    3860                3865            3870

Thr Ser Ala Ser Thr Ala Ser Thr Thr Ser Gly Pro Gly Thr Thr
    3875                3880            3885

Pro Ser Pro Val Pro Thr Thr Ser Thr Thr Ser Ala Pro Thr Thr
    3890                3895            3900

Ser Thr Thr Ser Ala Ser Thr Ala Ser Thr Thr Ser Gly Pro Gly
    3905                3910            3915

Thr Ser Leu Ser Pro Val Pro Thr Thr Ser Thr Thr Ser Ala Pro
    3920                3925            3930

Thr Thr Ser Thr Thr Ser Gly Pro Gly Thr Thr Pro Ser Pro Val
    3935                3940            3945

Pro Thr Thr Ser Thr Thr Ser Ala Pro Thr Thr Ser Thr Thr Ser
    3950                3955            3960

Gly Pro Gly Thr Thr Pro Ser Pro Val Pro Thr Thr Ser Thr Thr
    3965                3970            3975

Pro Val Ser Lys Thr Ser Thr Ser His Leu Ser Val Ser Lys Thr
    3980                3985            3990

Thr His Ser Gln Pro Val Thr Ser Asp Cys His Pro Leu Cys Ala
    3995                4000            4005

Trp Thr Lys Trp Phe Asp Val Asp Phe Pro Ser Pro Gly Pro His
    4010                4015            4020

Gly Gly Asp Lys Glu Thr Tyr Asn Asn Ile Ile Arg Ser Gly Glu
    4025                4030            4035

Lys Ile Cys Arg Arg Pro Glu Glu Ile Thr Arg Leu Gln Cys Arg
    4040                4045            4050

Ala Glu Ser His Pro Glu Val Asn Ile Glu His Leu Gly Gln Val
    4055                4060            4065

Val Gln Cys Ser Arg Glu Glu Gly Leu Val Cys Arg Asn Gln Asp
    4070                4075            4080

Gln Gln Gly Pro Phe Lys Met Cys Leu Asn Tyr Glu Val Arg Val
    4085                4090            4095

Leu Cys Cys Glu Thr Pro Arg Gly Cys Pro Val Thr Ser Val Thr
    4100                4105            4110

Pro Tyr Gly Thr Ser Pro Thr Asn Ala Leu Tyr Pro Ser Leu Ser
    4115                4120            4125

Thr Ser Met Val Ser Ala Ser Val Ala Ser Thr Ser Val Ala Ser
    4130                4135            4140

Ser Ser Val Ala Ser Ser Ser Val Ala Tyr Ser Thr Gln Thr Cys
    4145                4150            4155

Phe Cys Asn Val Ala Asp Arg Leu Tyr Pro Ala Gly Ser Thr Ile
    4160                4165            4170
```

-continued

Tyr Arg His Arg Asp Leu Ala Gly His Cys Tyr Tyr Ala Leu Cys
4175                4180                4185

Ser Gln Asp Cys Gln Val Val Arg Gly Val Asp Ser Asp Cys Pro
4190                4195                4200

Ser Thr Thr Leu Pro Pro Ala Pro Ala Thr Ser Pro Ser Ile Ser
4205                4210                4215

Thr Ser Glu Pro Val Thr Glu Leu Gly Cys Pro Asn Ala Val Pro
4220                4225                4230

Pro Arg Lys Lys Gly Glu Thr Trp Ala Thr Pro Asn Cys Ser Glu
4235                4240                4245

Ala Thr Cys Glu Gly Asn Asn Val Ile Ser Leu Ser Pro Arg Thr
4250                4255                4260

Cys Pro Arg Val Glu Lys Pro Thr Cys Ala Asn Gly Tyr Pro Ala
4265                4270                4275

Val Lys Val Ala Asp Gln Asp Gly Cys Cys His His Tyr Gln Cys
4280                4285                4290

Gln Cys Val Cys Ser Gly Trp Gly Asp Pro His Tyr Ile Thr Phe
4295                4300                4305

Asp Gly Thr Tyr Tyr Thr Phe Leu Asp Asn Cys Thr Tyr Val Leu
4310                4315                4320

Val Gln Gln Ile Val Pro Val Tyr Gly His Phe Arg Val Leu Val
4325                4330                4335

Asp Asn Tyr Phe Cys Gly Ala Glu Asp Gly Leu Ser Cys Pro Arg
4340                4345                4350

Ser Ile Ile Leu Glu Tyr His Gln Asp Arg Val Val Leu Thr Arg
4355                4360                4365

Lys Pro Val His Gly Val Met Thr Asn Glu Ile Ile Phe Asn Asn
4370                4375                4380

Lys Val Val Ser Pro Gly Phe Arg Lys Asn Gly Ile Val Val Ser
4385                4390                4395

Arg Ile Gly Val Lys Met Tyr Ala Thr Ile Pro Glu Leu Gly Val
4400                4405                4410

Gln Val Met Phe Ser Gly Leu Ile Phe Ser Val Glu Val Pro Phe
4415                4420                4425

Ser Lys Phe Ala Asn Asn Thr Glu Gly Gln Cys Gly Thr Cys Thr
4430                4435                4440

Asn Asp Arg Lys Asp Glu Cys Arg Thr Pro Arg Gly Thr Val Val
4445                4450                4455

Ala Ser Cys Ser Glu Met Ser Gly Leu Trp Asn Val Ser Ile Pro
4460                4465                4470

Asp Gln Pro Ala Cys His Arg Pro His Pro Thr Pro Thr Thr Val
4475                4480                4485

Gly Pro Thr Thr Val Gly Ser Thr Thr Val Gly Pro Thr Thr Val
4490                4495                4500

Gly Ser Thr Thr Val Gly Pro Thr Thr Pro Ala Pro Cys Leu
4505                4510                4515

Pro Ser Pro Ile Cys His Leu Ile Leu Ser Lys Val Phe Glu Pro
4520                4525                4530

Cys His Thr Val Ile Pro Pro Leu Leu Phe Tyr Glu Gly Cys Val
4535                4540                4545

Phe Asp Arg Cys His Met Thr Asp Leu Asp Val Val Cys Ser Ser
4550                4555                4560

Leu Glu Leu Tyr Ala Ala Leu Cys Ala Ser His Asp Ile Cys Ile

```
            4565                4570                4575

Asp Trp Arg Gly Arg Thr Gly His Met Cys Pro Phe Thr Cys Pro
        4580                4585                4590

Ala Asp Lys Val Tyr Gln Pro Cys Gly Pro Ser Asn Pro Ser Tyr
        4595                4600                4605

Cys Tyr Gly Asn Asp Ser Ala Ser Leu Gly Ala Leu Arg Glu Ala
        4610                4615                4620

Gly Pro Ile Thr Glu Gly Cys Phe Cys Pro Glu Gly Met Thr Leu
        4625                4630                4635

Phe Ser Thr Ser Ala Gln Val Cys Val Pro Thr Gly Cys Pro Arg
        4640                4645                4650

Cys Leu Gly Pro His Gly Glu Pro Val Lys Val Gly His Thr Val
        4655                4660                4665

Gly Met Asp Cys Gln Glu Cys Thr Cys Glu Ala Ala Thr Trp Thr
        4670                4675                4680

Leu Thr Cys Arg Pro Lys Leu Cys Pro Leu Pro Pro Ala Cys Pro
        4685                4690                4695

Leu Pro Gly Phe Val Pro Val Pro Ala Ala Pro Gln Ala Gly Gln
        4700                4705                4710

Cys Cys Pro Gln Tyr Ser Cys Ala Cys Asn Thr Ser Arg Cys Pro
        4715                4720                4725

Ala Pro Val Gly Cys Pro Glu Gly Ala Arg Ala Ile Pro Thr Tyr
        4730                4735                4740

Gln Glu Gly Ala Cys Cys Pro Val Gln Asn Cys Ser Trp Thr Val
        4745                4750                4755

Cys Ser Ile Asn Gly Thr Leu Tyr Gln Pro Gly Ala Val Val Ser
        4760                4765                4770

Ser Ser Leu Cys Glu Thr Cys Arg Cys Glu Leu Pro Gly Gly Pro
        4775                4780                4785

Pro Ser Asp Ala Phe Val Val Ser Cys Glu Thr Gln Ile Cys Asn
        4790                4795                4800

Thr His Cys Pro Val Gly Phe Glu Tyr Gln Glu Gln Ser Gly Gln
        4805                4810                4815

Cys Cys Gly Thr Cys Val Gln Val Ala Cys Val Thr Asn Thr Ser
        4820                4825                4830

Lys Ser Pro Ala His Leu Phe Tyr Pro Gly Glu Thr Trp Ser Asp
        4835                4840                4845

Ala Gly Asn His Cys Val Thr His Gln Cys Glu Lys His Gln Asp
        4850                4855                4860

Gly Leu Val Val Val Thr Thr Lys Lys Ala Cys Pro Pro Leu Ser
        4865                4870                4875

Cys Ser Leu Asp Glu Ala Arg Met Ser Lys Asp Gly Cys Cys Arg
        4880                4885                4890

Phe Cys Pro Leu Pro Pro Pro Tyr Gln Asn Gln Ser Thr Cys
        4895                4900                4905

Ala Val Tyr His Arg Ser Leu Ile Ile Gln Gln Gln Gly Cys Ser
        4910                4915                4920

Ser Ser Glu Pro Val Arg Leu Ala Tyr Cys Arg Gly Asn Cys Gly
        4925                4930                4935

Asp Ser Ser Ser Met Tyr Ser Leu Glu Gly Asn Thr Val Glu His
        4940                4945                4950

Arg Cys Gln Cys Cys Gln Glu Leu Arg Thr Ser Leu Arg Asn Val
        4955                4960                4965
```

```
Thr Leu His Cys Thr Asp Gly Ser Ser Arg Ala Phe Ser Tyr Thr
    4970            4975                4980

Glu Val Glu Glu Cys Gly Cys Met Gly Arg Arg Cys Pro Ala Pro
    4985            4990                4995

Gly Asp Thr Gln His Ser Glu Ala Glu Pro Glu Pro Ser Gln
    5000            5005                5010

Glu Ala Glu Ser Gly Ser Trp Glu Arg Gly Val Pro Val Ser Pro
    5015            5020                5025

Met His
    5030

<210> SEQ ID NO 2
<211> LENGTH: 921
<212> TYPE: DNA
<213> ORGANISM: Artificial Sequence
<220> FEATURE:
<223> OTHER INFORMATION: N-terminal fragment of MUC5AC

<400> SEQUENCE: 2
accacccatt ctcaacctgt tactcgtgat tgtcatctgc gttgcacctg gactaaatgg      60
ttcgacgttg acttcccgtc cccaggtcca cacggtggtg acaaggaaac ctataacaac     120
atcattcgtt ccggtgagaa aatctgccgt cgtccggagg aaatcacccg tctgcagtgc     180
cgtgcagagt cccaccccga ggtatctatc gaacatctgg gccaggttgt gcagtgcagc     240
cgtgaagaag gtctggtttg ccgtaaccaa gatcagcagg gcccgttcaa aatgtgcctg     300
aactatgaag tccgtgtcct gtgctgcgaa accccaaaag gctgtccagt tacttctacc     360
ccggttaccg cgccgtccac tccaagcggc gcgcgaccga gcccgaccca gagcacctcc     420
tcttggcaga aatcccgcac cactaccctg gttactacct ctactacctc cactccacag     480
acttccacca cctccgcccc gactaccagc actaccagcg cccccgaccac tagcactacc     540 tccgctccga ccacctccac cacttctacc ccgcagacct ctatctcttc tgcgccgacc     600
agctctacca ccagcgctcc gactagctcc acgatttctg ctcgtactac ttctatcatt     660
tccgccccta cgacctctac cacttctagc cctaccacct ctaccacgtc cgcgaccacc     720
acctccacta cctctgcacc aacttcctct actacgagca cgccgcagac ttctaaaacc     780
tctgcggcaa cctcttctac caccagcagc tctggcacca ctccgagccc ggtgaccacc     840
actagcaccg cttctgtgtc caagaccagc acctctcacg tgtctgtttc taaaacgacc     900
cactcccagc cggttacccg c                                                921

<210> SEQ ID NO 3
<211> LENGTH: 306
<212> TYPE: PRT
<213> ORGANISM: Artificial Sequence
<220> FEATURE:
<223> OTHER INFORMATION: N-terminal fragment of MUC5AC

<400> SEQUENCE: 3

Thr Thr His Ser Gln Pro Val Thr Arg Asp Cys His Leu Arg Cys Thr
  1               5                  10                  15

Trp Thr Lys Trp Phe Asp Val Asp Phe Pro Ser Pro Gly Pro His Gly
                 20                  25                  30

Gly Asp Lys Glu Thr Tyr Asn Asn Ile Ile Arg Ser Gly Glu Lys Ile
             35                  40                  45

Cys Arg Arg Pro Glu Glu Ile Thr Arg Leu Gln Cys Arg Ala Glu Ser
         50                  55                  60
```

-continued

His Pro Glu Val Ser Ile Glu His Leu Gly Gln Val Val Gln Cys Ser
 65                  70                  75                  80

Arg Glu Glu Gly Leu Val Cys Arg Asn Gln Asp Gln Gln Gly Pro Phe
                 85                  90                  95

Lys Met Cys Leu Asn Tyr Glu Val Arg Val Leu Cys Cys Glu Thr Pro
            100                 105                 110

Lys Gly Cys Pro Val Thr Ser Thr Pro Val Thr Ala Pro Ser Thr Pro
        115                 120                 125

Ser Gly Arg Ala Thr Ser Pro Thr Gln Ser Thr Ser Ser Trp Gln Lys
    130                 135                 140

Ser Arg Thr Thr Thr Leu Val Thr Thr Ser Thr Thr Ser Thr Pro Gln
145                 150                 155                 160

Thr Ser Thr Thr Ser Ala Pro Thr Thr Ser Thr Thr Ser Ala Pro Thr
                165                 170                 175

Thr Ser Thr Thr Ser Ala Pro Thr Thr Ser Thr Thr Ser Thr Pro Gln
                180                 185                 190

Thr Ser Ile Ser Ser Ala Pro Thr Ser Ser Thr Thr Ser Ala Pro Thr
            195                 200                 205

Ser Ser Thr Ile Ser Ala Arg Thr Thr Ser Ile Ile Ser Ala Pro Thr
    210                 215                 220

Thr Ser Thr Thr Ser Ser Pro Thr Thr Ser Thr Thr Ser Ala Thr Thr
225                 230                 235                 240

Thr Ser Thr Thr Ser Ala Pro Thr Ser Ser Thr Thr Ser Thr Pro Gln
                245                 250                 255

Thr Ser Lys Thr Ser Ala Ala Thr Ser Ser Thr Thr Ser Ser Ser Gly
                260                 265                 270

Thr Thr Pro Ser Pro Val Thr Thr Thr Ser Thr Ala Ser Val Ser Lys
            275                 280                 285

Thr Thr Ser His Val Ser Val Ser Lys Thr Thr His Ser Gln Pro Val
            290                 295                 300

Thr Arg
305

<210> SEQ ID NO 4
<211> LENGTH: 384
<212> TYPE: DNA
<213> ORGANISM: Artificial Sequence
<220> FEATURE:
<223> OTHER INFORMATION: N-terminal fragment of MUC5AC

<400> SEQUENCE: 4
actactcatt ctcaacctgt aactcgtgat tgtcatctgc gctgtacttg gactaaatgg      60
tttgacgtgg acttcccgtc ccctggcccg cacggtggtg ataaagaaac ctacaataac     120
atcattcgct ctggtgagaa aatctgccgt cgtccggaag aaatcactcg tctgcaatgt     180
cgtgccgaat cccacccgga ggtgagcatc gaacacctgg gtcaggttgt tcagtgttct     240
cgtgaggaag gtctggtatg ccgtaaccaa gatcagcaag gcccattcaa aatgtgcctg     300
aactacgaag ttcgtgttct gtgttgcgag actccgaaag gttgcccggt tacgagcacg     360
cctgtcaccg caccgagcac gccg                                           384

<210> SEQ ID NO 5
<211> LENGTH: 128
<212> TYPE: PRT
<213> ORGANISM: Artificial Sequence
<220> FEATURE:

<223> OTHER INFORMATION: N-terminal fragment of MUC5AC

<400> SEQUENCE: 5

```
Thr Thr His Ser Gln Pro Val Thr Arg Asp Cys His Leu Arg Cys Thr
1               5                   10                  15

Trp Thr Lys Trp Phe Asp Val Asp Phe Pro Ser Pro Gly Pro His Gly
            20                  25                  30

Gly Asp Lys Glu Thr Tyr Asn Asn Ile Ile Arg Ser Gly Glu Lys Ile
        35                  40                  45

Cys Arg Arg Pro Glu Glu Ile Thr Arg Leu Gln Cys Arg Ala Glu Ser
    50                  55                  60

His Pro Glu Val Ser Ile Glu His Leu Gly Gln Val Val Gln Cys Ser
65                  70                  75                  80

Arg Glu Glu Gly Leu Val Cys Arg Asn Gln Asp Gln Gln Gly Pro Phe
                85                  90                  95

Lys Met Cys Leu Asn Tyr Glu Val Arg Val Leu Cys Cys Glu Thr Pro
            100                 105                 110

Lys Gly Cys Pro Val Thr Ser Thr Pro Val Thr Ala Pro Ser Thr Pro
        115                 120                 125
```

<210> SEQ ID NO 6
<211> LENGTH: 45
<212> TYPE: PRT
<213> ORGANISM: Artificial Sequence
<220> FEATURE:
<223> OTHER INFORMATION: MUC5AC termolysin fragment2

<400> SEQUENCE: 6

```
Leu Val Thr Thr Ser Thr Thr Ser Thr Pro Gln Thr Ser Thr Thr Ser
1               5                   10                  15

Ala Pro Thr Thr Ser Thr Thr Ser Ala Pro Thr Thr Ser Thr Thr Ser
            20                  25                  30

Ala Pro Thr Thr Ser Thr Thr Ser Thr Pro Gln Thr Ser
        35                  40                  45
```

<210> SEQ ID NO 7
<211> LENGTH: 46
<212> TYPE: PRT
<213> ORGANISM: Artificial Sequence
<220> FEATURE:
<223> OTHER INFORMATION: MUC5AC thermolysin fragment4

<400> SEQUENCE: 7

```
Ser Ser Pro Thr Thr Ser Thr Thr Pro Thr Pro Gln Thr Ser Thr Thr
1               5                   10                  15

Ser Ser Pro Thr Thr Ser Thr Thr Ser Ala Pro Thr Thr Ser Thr Thr
            20                  25                  30

Ser Ala Pro Thr Thr Ser Thr Thr Ser Thr Pro Gln Thr Ser
        35                  40                  45
```

<210> SEQ ID NO 8
<211> LENGTH: 59
<212> TYPE: PRT
<213> ORGANISM: Artificial Sequence
<220> FEATURE:
<223> OTHER INFORMATION: MUC5AC thermolysin fragment1

<400> SEQUENCE: 8

```
Ile Thr Ser Ala Pro Thr Thr Ser Thr Thr Ser Ala Pro Thr Thr Ser
1               5                   10                  15
```

```
Thr Thr Ser Ala Pro Thr Thr Ser Thr Thr Ser Ala Pro Thr Thr Ser
            20                  25                  30

Thr Thr Ser Ala Pro Thr Thr Ser Thr Thr Ser Thr Pro Thr Ser Ser
            35                  40                  45

Thr Thr Ser Thr Pro Gln Thr Ser Thr Thr Ser
            50                  55
```

<210> SEQ ID NO 9
<211> LENGTH: 54
<212> TYPE: PRT
<213> ORGANISM: Artificial Sequence
<220> FEATURE:
<223> OTHER INFORMATION: MUC5AC thermolysin fragment3

<400> SEQUENCE: 9

```
Ala Ser Ile Pro Ser Thr Thr Ser Ala Pro Thr Thr Ser Thr Thr Ser
1               5                   10                  15

Ala Pro Thr Thr Ser Thr Thr Ser Ala Pro Thr Thr Ser Thr Thr Ser
            20                  25                  30

Thr Pro Gln Thr Thr Thr Ser Ser Ala Pro Thr Ser Ser Thr Thr Ser
            35                  40                  45

Ala Pro Thr Thr Ser Thr
        50
```

<210> SEQ ID NO 10
<211> LENGTH: 45
<212> TYPE: PRT
<213> ORGANISM: Artificial Sequence
<220> FEATURE:
<223> OTHER INFORMATION: MUC5AC thermolysin fragment5

<400> SEQUENCE: 10

```
Met Thr Ser Gly Pro Gly Thr Thr Pro Ser Pro Val Pro Thr Thr Ser
1               5                   10                  15

Thr Thr Ser Ala Pro Thr Thr Ser Thr Thr Ser Gly Pro Gly Thr Thr
            20                  25                  30

Pro Ser Pro Val Pro Thr Thr Ser Thr Thr Ser Ala Pro
        35                  40                  45
```

<210> SEQ ID NO 11
<211> LENGTH: 54
<212> TYPE: PRT
<213> ORGANISM: Artificial Sequence
<220> FEATURE:
<223> OTHER INFORMATION: MUC5AC thermolysin fragment6

<400> SEQUENCE: 11

```
Ile Thr Ser Met Pro Ser Gly Pro Gly Thr Thr Pro Ser Pro Val Pro
1               5                   10                  15

Thr Thr Ser Thr Thr Ser Ala Pro Thr Thr Ser Thr Thr Ser Gly Pro
            20                  25                  30

Gly Thr Thr Pro Ser Pro Val Pro Thr Thr Ser Thr Thr Ser Ala Pro
            35                  40                  45

Thr Thr Ser Thr Thr Ser
        50
```

<210> SEQ ID NO 12
<211> LENGTH: 59
<212> TYPE: PRT
<213> ORGANISM: Artificial Sequence
<220> FEATURE:
<223> OTHER INFORMATION: MUC5AC thermolysin fragment7

<400> SEQUENCE: 12

Leu Ser Pro Val Pro Thr Thr Ser Thr Thr Ser Ala Pro Thr Thr Ser
1               5                   10                  15

Thr Thr Ser Gly Pro Gly Thr Thr Pro Ser Pro Val Pro Thr Thr Ser
            20                  25                  30

Thr Thr Ser Ala Pro Thr Thr Ser Thr Thr Ser Gly Pro Gly Thr Thr
        35                  40                  45

Pro Ser Pro Val Pro Thr Thr Ser Thr Thr Pro
    50                  55

<210> SEQ ID NO 13
<211> LENGTH: 85
<212> TYPE: PRT
<213> ORGANISM: Artificial Sequence
<220> FEATURE:
<223> OTHER INFORMATION: MUC5AC truncation construct (85)

<400> SEQUENCE: 13

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala
                85

<210> SEQ ID NO 14
<211> LENGTH: 136
<212> TYPE: PRT
<213> ORGANISM: Artificial Sequence
<220> FEATURE:
<223> OTHER INFORMATION: MUC5AC truncation construct (136)

<400> SEQUENCE: 14

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys
    130                 135

```
<210> SEQ ID NO 15
<211> LENGTH: 151
<212> TYPE: PRT
<213> ORGANISM: Artificial Sequence
<220> FEATURE:
<223> OTHER INFORMATION: MUC5AC truncation construct (151)

<400> SEQUENCE: 15

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
    130                 135                 140

Val Thr Ala Pro Ser Thr Pro
145                 150

<210> SEQ ID NO 16
<211> LENGTH: 187
<212> TYPE: PRT
<213> ORGANISM: Artificial Sequence
<220> FEATURE:
<223> OTHER INFORMATION: MUC5AC truncation construct (187)

<400> SEQUENCE: 16

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
    130                 135                 140

Val Thr Ala Pro Ser Thr Pro Ser Gly Arg Ala Thr Ser Pro Thr Gln
```

```
                145                 150                 155                 160
Ser Thr Ser Ser Trp Gln Lys Ser Arg Thr Thr Thr Leu Val Thr Thr
                    165                 170                 175
Ser Thr Thr Ser Thr Pro Gln Thr Ser Thr Thr
                180                 185

<210> SEQ ID NO 17
<211> LENGTH: 289
<212> TYPE: PRT
<213> ORGANISM: Artificial Sequence
<220> FEATURE:
<223> OTHER INFORMATION: MUC5AC truncation construct (289)

<400> SEQUENCE: 17

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
                20                  25                  30

Asp Cys His Leu Arg Cys Thr Trp Thr Lys Trp Phe Asp Val Asp Phe
            35                  40                  45

Pro Ser Pro Gly Pro His Gly Gly Asp Lys Glu Thr Tyr Asn Asn Ile
        50                  55                  60

Ile Arg Ser Gly Glu Lys Ile Cys Arg Arg Pro Glu Ile Thr Arg
65              70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
130                 135                 140

Val Thr Ala Pro Ser Thr Pro Ser Gly Arg Ala Thr Ser Pro Thr Gln
145                 150                 155                 160

Ser Thr Ser Ser Trp Gln Lys Ser Arg Thr Thr Thr Leu Val Thr Thr
                165                 170                 175

Ser Thr Thr Ser Thr Pro Gln Thr Ser Thr Thr Ser Ala Pro Thr Thr
                180                 185                 190

Ser Thr Thr Ser Ala Pro Thr Thr Ser Thr Thr Ser Ala Pro Thr Thr
            195                 200                 205

Ser Thr Thr Ser Thr Pro Gln Thr Ser Ile Ser Ser Ala Pro Thr Ser
        210                 215                 220

Ser Thr Thr Ser Ala Pro Thr Ser Ser Thr Ile Ser Ala Arg Thr Thr
225                 230                 235                 240

Ser Ile Ile Ser Ala Pro Thr Thr Ser Thr Thr Ser Ser Pro Thr Thr
                245                 250                 255

Ser Thr Thr Ser Ala Thr Thr Ser Thr Thr Ser Ala Pro Thr Ser
                260                 265                 270

Ser Thr Thr Ser Thr Pro Gln Thr Ser Lys Thr Ser Ala Ala Thr Ser
        275                 280                 285

Ser

<210> SEQ ID NO 18
<211> LENGTH: 338
<212> TYPE: PRT
<213> ORGANISM: Artificial Sequence
```

<220> FEATURE:
<223> OTHER INFORMATION: MUC5AC truncation construct (338)

<400> SEQUENCE: 18

```
Ala Thr Met Ser Val Gly Arg Arg Lys Leu Ala Leu Leu Trp Ala Leu
1               5                   10                  15

Ala Leu Ala Leu Ala Cys Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
                100                 105                 110

Gln Asp Gln Gln Gly Pro Phe Lys Met Cys Leu Asn Tyr Glu Val Arg
            115                 120                 125

Val Leu Cys Cys Glu Thr Pro Lys Gly Cys Pro Val Thr Ser Thr Pro
        130                 135                 140

Val Thr Ala Pro Ser Thr Pro Ser Gly Arg Ala Thr Ser Pro Thr Gln
145                 150                 155                 160

Ser Thr Ser Ser Trp Gln Lys Ser Arg Thr Thr Thr Leu Val Thr Thr
                165                 170                 175

Ser Thr Thr Ser Thr Pro Gln Thr Ser Thr Thr Ser Ala Pro Thr Thr
                180                 185                 190

Ser Thr Thr Ser Ala Pro Thr Thr Ser Thr Thr Ser Ala Pro Thr Thr
            195                 200                 205

Ser Thr Thr Ser Thr Pro Gln Thr Ser Ile Ser Ser Ala Pro Thr Ser
            210                 215                 220

Ser Thr Thr Ser Ala Pro Thr Ser Ser Thr Ile Ser Ala Arg Thr Thr
225                 230                 235                 240

Ser Ile Ile Ser Ala Pro Thr Thr Ser Thr Thr Ser Ser Pro Thr Thr
                245                 250                 255

Ser Thr Thr Ser Ala Thr Thr Ser Thr Thr Ser Ala Pro Thr Ser
            260                 265                 270

Ser Thr Thr Ser Thr Pro Gln Thr Ser Lys Thr Ser Ala Ala Thr Ser
            275                 280                 285

Ser Thr Thr Ser Ser Gly Thr Thr Pro Ser Pro Val Thr Thr Thr
            290                 295                 300

Ser Thr Ala Ser Val Ser Lys Thr Ser Thr Ser His Val Ser Val Ser
305                 310                 315                 320

Lys Thr Thr His Ser Gln Pro Val Thr Arg Cys Thr His His His
                325                 330                 335

His His
```

<210> SEQ ID NO 19
<211> LENGTH: 502
<212> TYPE: PRT
<213> ORGANISM: Homo sapiens

<400> SEQUENCE: 19

Met Glu Ser Pro Ser Ala Pro Pro His Arg Trp Cys Ile Pro Trp Gln

-continued

```
1               5                   10                  15
Arg Leu Leu Leu Thr Ala Ser Leu Leu Thr Phe Trp Asn Pro Pro Thr
                20                  25              30

Thr Ala Lys Leu Thr Ile Glu Ser Thr Pro Phe Asn Val Ala Glu Gly
        35                  40                  45

Lys Glu Val Leu Leu Val His Asn Leu Pro Gln His Leu Phe Gly
        50                  55              60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
                100                 105                 110

Ile Gln Asn Asp Thr Gly Phe Tyr Thr Leu His Val Ile Lys Ser Asp
                115                 120                 125

Leu Val Asn Glu Glu Ala Thr Gly Gln Phe Arg Val Tyr Pro Glu Leu
        130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                    165                 170                 175

Leu Trp Trp Val Asn Asn Gln Ser Leu Pro Val Ser Pro Arg Leu Gln
                180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
        210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
        260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
        290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
                340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
        370                 375                 380

Arg Asn Asp Val Gly Pro Tyr Glu Cys Gly Ile Gln Asn Ile Ser Pro
385                 390                 395                 400

Pro Asp Ser Ser Tyr Leu Ser Gly Ala Asn Leu Asn Leu Ser Cys His
                405                 410                 415

Ser Ala Ser Asn Pro Ser Pro Gln Tyr Ser Trp Arg Ile Asn Gly Ile
                420                 425                 430
```

Pro Gln Gln His Thr Gln Val Leu Phe Ile Ala Lys Ile Thr Pro Asn
    435                 440                 445

Asn Asn Gly Thr Tyr Ala Cys Phe Val Ser Asn Leu Ala Thr Gly Arg
    450                 455                 460

Asn Asn Ser Ile Val Lys Ser Ile Thr Val Ser Ala Ser Gly Thr Ser
465                 470                 475                 480

Pro Gly Leu Ser Ala Gly Ala Thr Val Gly Ile Met Ile Gly Val Leu
                485                 490                 495

Val Gly Val Ala Leu Ile
                500

<210> SEQ ID NO 20
<211> LENGTH: 3600
<212> TYPE: DNA
<213> ORGANISM: Homo sapiens

<400> SEQUENCE: 20
gaagagactc agggcagagg gaggaaggac agcagaccag acagtcacag cagccttgac      60
aaaacgttcc tggaactcaa gctcttctcc acagaggagg acagagcaga cagcagagac     120
catggagtct ccctcggccc ctccccacag atggtgcatc cctggcagag ggctcctgct     180
cacagcctca cttctaacct tctggaaccc gcccaccact gccaagctca ctattgaatc     240
cacgccgttc aatgtcgcag aggggaagga ggtgcttcta cttgtccaca atctgcccca     300
gcatcttttt ggctacagct ggtacaaagg tgaaagagtg gatggcaacc gtcaaattat     360
aggatatgta ataggaactc aacaagctac cccagggccc gcatacagtg gtcgagagat     420 aatataccc aatgcatccc tgctgatcca gaacatcatc cagaatgaca caggattcta     480
cacccctaca gtcataaagt cagatcttgt gaatgaagaa gcaactggcc agttccgggt     540
ataccccgag ctgcccaagc cctccatctc cagcaacaac tccaaacccg tggaggacaa     600
ggatgctgtg gccttcacct gtgaacctga gactcaggac gcaacctacc tgtggtgggt     660
aaacaatcag agcctcccgg tcagtcccag gctgcagctg tccaatggca caggaccct     720 cactctattc aatgtcacaa gaatgacac agcaagctac aaatgtgaaa cccagaaccc     780
agtgagtgcc aggcgcagtg attcagtcat cctgaatgtc ctctatggcc cggatgcccc     840
caccatttcc cctctaaaca catcttacag atcaggggaa aatctgaacc tctcctgcca     900
cgcagcctct aacccacctg cacagtactc ttggtttgtc aatgggactt tccagcaatc     960
cacccaagag ctctttatcc caacatcac tgtgaataat agtggatcct atacgtgcca    1020
agcccataac tcagacactg gcctcaatag gaccacagtc acgacgatca gtgtctatgc    1080
agagccaccc aaaccttca tcaccagcaa caactccaac cccgtggagg atgaggatgc    1140
tgtagcctta acctgtgaac ctgagattca gaacacaacc tacctgtggt gggtaaataa    1200
tcagagcctc ccggtcagtc ccaggctgca gctgtccaat gacaacagga ccctcactct    1260
actcagtgtc acaaggaatg atgtaggacc ctatgagtgt ggaatccaga acaaattaag    1320
tgttgaccac agcgacccag tcatcctgaa tgtcctctat ggcccagacg accccaccat    1380 tccccctca tacaccctatt accgtccagg ggtgaacctc agcctctcct gcatgcagc    1440 ctctaaccca cctgcacagt attcttggct gattgatggg aacatccagc aacacacaca    1500
agagctcttt atctccaaca tcactgagaa gaacagcgga ctctataccta gcaggccaa    1560 taactcagcc agtggccaca gcaggactac agtcaagaca atcacagtct ctgcggagct    1620
gcccaagccc tccatctcca gcaacaactc caaacccgtg gaggacaagg atgctgtggc    1680

```
cttcacctgt gaacctgagg ctcagaacac aacctacctg tggtgggtaa atggtcagag    1740
cctcccagtc agtcccaggc tgcagctgtc caatggcaac aggaccctca ctctattcaa    1800
tgtcacaaga aatgacgcaa gagcctatgt atgtggaatc cagaactcag tgagtgcaaa    1860
ccgcagtgac ccagtcaccc tggatgtcct ctatgggccg acaccccca tcatttcccc     1920 cccagactcg tcttaccttt cgggagcgaa cctcaacctc tcctgccact cggcctctaa    1980
cccatccccg cagtattctt ggcgtatcaa tgggataccg cagcaacaca cacaagttct    2040
ctttatcgcc aaaatcacgc caaataataa cgggacctat gcctgttttg tctctaactt    2100
ggctactggc cgcaataatt ccatagtcaa gagcatcaca gtctctgcat ctggaacttc    2160
tcctggtctc tcagctgggg ccactgtcgg catcatgatt ggagtgctgg ttggggttgc    2220
tctgatatag cagccctggt gtagtttctt catttcagga agactgacag ttgttttgct    2280
tcttccttaa agcatttgca acagctacag tctaaaattg cttctttacc aaggatattt    2340
acagaaaaga ctctgaccag agatcgagac catcctagcc aacatcgtga aaccccatct    2400
ctactaaaaa tacaaaaatg agctgggctt ggtggcgcgc acctgtagtc ccagttactc    2460
gggaggctga ggcaggagaa tcgcttgaac ccggggaggtg gagattgcag tgagcccaga    2520
tcgcaccact gcactccagt ctggcaacag agcaagactc catctcaaaa agaaaagaaa    2580
agaagactct gacctgtact cttgaataca agtttctgat accactgcac tgtctgagaa    2640
tttccaaaac tttaatgaac taactgacag cttcatgaaa ctgtccacca agatcaagca    2700
gagaaaataa ttaatttcat gggactaaat gaactaatga ggataatatt ttcataattt    2760
tttatttgaa attttgctga ttctttaaat gtcttgtttc ccagatttca ggaaactttt    2820 tttctttaa gctatccaca gcttacagca atttgataaa atatacttttt gtgaacaaaa    2880 attgagacat ttacattttc tccctatgtg gtcgctccag acttgggaaa ctattcatga    2940
atatttatat tgtatggtaa tatagttatt gcacaagttc aataaaaatc tgctctttgt    3000
atgacagaat acatttgaaa acattggtta tattaccaag actttgacta gaatgtcgta    3060
tttgaggata taaacccata ggtaataaac ccacaggtac tacaaacaaa gtctgaagtc    3120
agccttggtt tggcttccta gtgtcaatta aacttctaaa agtttaatct gagattcctt    3180
ataaaaactt ccagcaaagc aactttaaaa aagtctgtgt gggccgggcg cggtggctca    3240
cgcctgtaat cccagcactt tgatccgccg aggcgggcgg atcacgaggt caggagatcc    3300
agaccatcct ggctaacaca gtgaaacccc gtctctacta aaaatacaaa aaaagttagc    3360
cgggcgtggt ggtgggggcc tgtagtccca gctactcagg aggctgaggc aggagaacgg    3420
catgaacccg ggaggcaggg cttgcagtga gccaagatca tgccgctgca ctccagcctg    3480
ggagacaaag tgagactccg tcaaaaaaaa aaaaagtct atgtggtcag tcactactct    3540
tgctgcagtt atgaaaagaa tgaggccaag tctgatgaaa ataaacttat tttgaaaaca    3600
```

<210> SEQ ID NO 21
<211> LENGTH: 344
<212> TYPE: PRT
<213> ORGANISM: Homo sapiens

<400> SEQUENCE: 21

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

```
Thr Ala Lys Leu Thr Ile Glu Ser Thr Pro Phe Asn Val Ala Glu Gly
         35                  40                  45

Lys Glu Val Leu Leu Ala His Asn Leu Pro Gln Asn Arg Ile Gly
 50                  55                  60

Tyr Ser Trp Tyr Lys Gly Glu Arg Val Asp Gly Asn Ser Leu Ile Val
 65                  70                  75                  80

Gly Tyr Val Ile Gly Thr Gln Gln Ala Thr Pro Gly Pro Ala Tyr Ser
                 85                  90                  95

Gly Arg Glu Thr Ile Tyr Pro Asn Ala Ser Leu Leu Ile Gln Asn Val
             100                 105                 110

Thr Gln Asn Asp Thr Gly Phe Tyr Thr Leu Gln Val Ile Lys Ser Asp
         115                 120                 125

Leu Val Asn Glu Glu Ala Thr Gly Gln Phe His Val Tyr Pro Glu Leu
130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 22
<211> LENGTH: 2631
<212> TYPE: PRT
<213> ORGANISM: Homo sapiens

<400> SEQUENCE: 22

Gly Ala Cys Cys Cys Thr Gly Gly Gly Ala Ala Ala Thr Gly Cys Thr
 1               5                  10                  15

Thr Cys Thr Ala Thr Cys Cys Thr Gly Ala Gly Ala Gly Gly Ala
             20                  25                  30

Gly Gly Cys Thr Cys Ala Gly Cys Ala Cys Ala Gly Ala Ala Gly Gly
         35                  40                  45

Ala Gly Gly Ala Ala Gly Gly Ala Cys Ala Gly Cys Ala Gly Gly Gly
 50                  55                  60
```

```
Cys Cys Ala Ala Cys Ala Gly Thr Cys Ala Cys Ala Gly Cys Ala Gly
65 70 75 80

Cys Cys Cys Thr Gly Ala Cys Cys Ala Gly Ala Gly Cys Ala Thr Thr
85 90 95

Cys Cys Thr Gly Gly Ala Gly Cys Thr Cys Ala Ala Gly Cys Thr Cys
100 105 110

Cys Thr Cys Thr Ala Cys Ala Ala Ala Gly Ala Gly Gly Thr Gly Gly
115 120 125

Ala Cys Ala Gly Ala Gly Ala Ala Gly Ala Cys Ala Gly Cys Ala Gly
130 135 140

Ala Gly Ala Cys Cys Ala Thr Gly Gly Gly Ala Cys Cys Cys Cys Cys
145 150 155 160

Cys Thr Cys Ala Gly Cys Cys Cys Cys Thr Cys Cys Cys Thr Gly Cys
165 170 175

Ala Gly Ala Thr Thr Gly Cys Ala Thr Gly Thr Cys Cys Cys Cys Thr
180 185 190

Gly Gly Ala Ala Gly Gly Ala Gly Gly Thr Cys Cys Thr Gly Cys Thr
195 200 205

Cys Ala Cys Ala Gly Cys Cys Thr Cys Ala Cys Thr Thr Cys Thr Ala
210 215 220

Ala Cys Cys Thr Thr Cys Thr Gly Gly Ala Ala Cys Cys Cys Ala Cys
225 230 235 240

Cys Cys Ala Cys Cys Ala Cys Thr Gly Cys Cys Ala Ala Gly Cys Thr
245 250 255

Cys Ala Cys Thr Ala Thr Thr Gly Ala Ala Thr Cys Cys Ala Cys Gly
260 265 270

Cys Cys Gly Thr Thr Cys Ala Ala Thr Gly Thr Cys Gly Cys Ala Gly
275 280 285

Ala Gly Gly Gly Gly Ala Ala Gly Gly Ala Gly Gly Thr Thr Cys Thr
290 295 300

Thr Cys Thr Ala Cys Thr Cys Gly Cys Cys Cys Ala Cys Ala Ala Cys
305 310 315 320

Cys Thr Gly Cys Cys Cys Cys Ala Gly Ala Ala Thr Cys Gly Thr Ala
325 330 335

Thr Thr Gly Gly Thr Thr Ala Cys Ala Gly Cys Thr Gly Gly Thr Ala
340 345 350

Cys Ala Ala Ala Gly Gly Cys Gly Ala Ala Ala Gly Ala Gly Thr Gly
355 360 365

Gly Ala Thr Gly Gly Cys Ala Ala Cys Ala Gly Thr Cys Thr Ala Ala
370 375 380

Thr Thr Gly Thr Ala Gly Gly Ala Thr Ala Thr Gly Thr Ala Ala Thr
385 390 395 400

Ala Gly Gly Ala Ala Cys Thr Cys Ala Ala Cys Ala Ala Gly Cys Thr
405 410 415

Ala Cys Cys Cys Cys Ala Gly Gly Gly Cys Cys Cys Gly Cys Ala Thr
420 425 430

Ala Cys Ala Gly Thr Gly Gly Thr Cys Gly Ala Gly Ala Gly Ala Cys
435 440 445

Ala Ala Thr Ala Thr Ala Cys Cys Cys Cys Ala Ala Thr Gly Cys Ala
450 455 460

Thr Cys Cys Cys Thr Gly Cys Thr Gly Ala Thr Cys Cys Ala Gly Ala
465 470 475 480

```
Ala Cys Gly Thr Cys Ala Cys Cys Ala Gly Ala Thr Gly Ala
            485                 490                 495

Cys Ala Cys Ala Gly Gly Ala Thr Thr Cys Thr Ala Thr Ala Cys Cys
            500                 505                 510

Cys Thr Ala Cys Ala Ala Gly Thr Cys Ala Thr Ala Ala Ala Gly Thr
            515                 520                 525

Cys Ala Gly Ala Thr Cys Thr Thr Gly Thr Gly Ala Ala Thr Gly Ala
            530                 535                 540

Ala Gly Ala Ala Gly Cys Ala Ala Cys Gly Gly Ala Cys Ala Gly
545                 550                 555                 560

Thr Thr Cys Cys Ala Thr Gly Thr Ala Thr Ala Cys Cys Gly Gly
                565                 570                 575

Ala Gly Cys Thr Gly Cys Cys Ala Ala Gly Cys Cys Thr Cys
            580                 585                 590

Cys Ala Thr Cys Thr Cys Cys Ala Gly Cys Ala Ala Cys Ala Ala Cys
            595                 600                 605

Thr Cys Cys Ala Ala Cys Cys Cys Gly Thr Gly Gly Ala Gly Gly
            610                 615                 620

Ala Cys Ala Ala Gly Gly Ala Thr Gly Cys Thr Gly Thr Gly Gly Cys
625                 630                 635                 640

Cys Thr Thr Cys Ala Cys Cys Thr Gly Thr Gly Ala Ala Cys Cys Thr
                645                 650                 655

Gly Ala Gly Gly Thr Thr Cys Ala Gly Ala Ala Cys Ala Cys Ala Ala
                660                 665                 670

Cys Cys Thr Ala Cys Cys Thr Gly Thr Gly Gly Thr Gly Gly Gly Thr
            675                 680                 685

Ala Ala Ala Thr Gly Gly Thr Cys Ala Gly Ala Gly Cys Cys Thr Cys
690                 695                 700

Cys Cys Gly Gly Thr Cys Ala Gly Thr Cys Cys Ala Gly Gly Cys
705                 710                 715                 720

Thr Gly Cys Ala Gly Cys Thr Gly Thr Cys Cys Ala Ala Thr Gly Gly
            725                 730                 735

Cys Ala Ala Cys Ala Thr Gly Ala Cys Cys Cys Thr Cys Ala Cys Thr
            740                 745                 750

Cys Thr Ala Cys Thr Cys Ala Gly Cys Gly Thr Cys Ala Ala Ala Ala
            755                 760                 765

Gly Gly Ala Ala Cys Gly Ala Thr Gly Cys Ala Gly Gly Ala Thr Cys
            770                 775                 780

Cys Thr Ala Thr Gly Ala Ala Thr Gly Thr Gly Ala Ala Ala Thr Ala
785                 790                 795                 800

Cys Ala Gly Ala Ala Cys Cys Cys Ala Gly Cys Gly Ala Gly Thr Gly
            805                 810                 815

Cys Cys Ala Ala Cys Cys Gly Cys Ala Gly Thr Gly Ala Cys Cys Cys
            820                 825                 830

Ala Gly Thr Cys Ala Cys Cys Thr Gly Ala Ala Thr Gly Thr Cys
            835                 840                 845

Cys Thr Cys Thr Ala Thr Gly Gly Cys Cys Ala Gly Ala Thr Gly
            850                 855                 860

Gly Cys Cys Cys Cys Ala Cys Ala Thr Thr Cys Cys Cys
865                 870                 875                 880

Cys Thr Cys Ala Ala Gly Gly Cys Cys Ala Thr Thr Ala Cys
            885                 890                 895

Cys Gly Thr Cys Cys Ala Gly Gly Gly Gly Ala Ala Ala Ala Thr Cys
```

-continued

```
              900                 905                 910
Thr Gly Ala Ala Cys Cys Thr Cys Thr Cys Cys Thr Gly Cys Cys Ala
              915                 920                 925
Cys Gly Cys Ala Gly Cys Cys Thr Cys Thr Ala Cys Cys Cys Ala
              930                 935                 940
Cys Cys Thr Gly Cys Ala Cys Ala Gly Thr Ala Cys Thr Cys Thr Thr
945                 950                 955                 960
Gly Gly Thr Thr Thr Ala Thr Cys Ala Ala Thr Gly Gly Gly Ala Cys
              965                 970                 975
Gly Thr Thr Cys Cys Ala Gly Cys Ala Ala Thr Cys Cys Ala Cys Ala
              980                 985                 990
Cys Ala Ala Gly Ala Gly Cys Thr Cys Thr Thr Ala Thr Cys Cys
              995                 1000                1005
Cys Cys Ala Ala Cys Ala Thr Cys Ala Cys Thr Gly Thr Gly Ala
              1010                1015                1020
Ala Thr Ala Ala Thr Ala Gly Cys Gly Gly Ala Thr Cys Cys Thr
              1025                1030                1035
Ala Thr Ala Thr Gly Thr Gly Cys Cys Ala Ala Gly Cys Cys Cys
              1040                1045                1050
Ala Thr Ala Ala Cys Thr Cys Ala Gly Cys Cys Ala Cys Thr Gly
              1055                1060                1065
Gly Cys Cys Thr Cys Ala Ala Thr Ala Gly Gly Ala Cys Cys Ala
              1070                1075                1080
Cys Ala Gly Thr Cys Ala Cys Gly Ala Thr Gly Ala Thr Cys Ala
              1085                1090                1095
Cys Ala Gly Thr Cys Thr Cys Thr Gly Gly Ala Ala Gly Thr Gly
              1100                1105                1110
Cys Thr Cys Cys Thr Gly Thr Cys Cys Thr Cys Thr Cys Ala Gly
              1115                1120                1125
Cys Thr Gly Thr Gly Gly Cys Cys Ala Cys Cys Gly Thr Cys Gly
              1130                1135                1140
Gly Cys Ala Thr Cys Ala Cys Gly Ala Thr Thr Gly Gly Ala Gly
              1145                1150                1155
Thr Gly Cys Thr Gly Gly Cys Cys Ala Gly Gly Gly Thr Gly Gly
              1160                1165                1170
Cys Thr Cys Thr Gly Ala Thr Ala Thr Ala Gly Cys Ala Gly Cys
              1175                1180                1185
Cys Cys Thr Gly Gly Thr Gly Thr Ala Thr Thr Thr Thr Cys Gly
              1190                1195                1200
Ala Thr Ala Thr Thr Thr Cys Ala Gly Gly Ala Ala Gly Ala Cys
              1205                1210                1215
Thr Gly Gly Cys Ala Gly Ala Thr Thr Gly Gly Ala Cys Cys Ala
              1220                1225                1230
Gly Ala Cys Cys Cys Thr Gly Ala Ala Thr Thr Cys Thr Thr Cys
              1235                1240                1245
Thr Ala Gly Cys Thr Cys Cys Thr Cys Cys Ala Ala Thr Cys Cys
              1250                1255                1260
Cys Ala Thr Thr Thr Thr Ala Thr Cys Cys Ala Thr Gly Gly
              1265                1270                1275
Ala Ala Cys Cys Ala Cys Thr Ala Ala Ala Ala Cys Ala Ala
              1280                1285                1290
Gly Gly Thr Cys Thr Gly Cys Thr Cys Thr Gly Cys Thr Cys Cys
              1295                1300                1305
```

```
Thr Gly Ala Ala Gly Cys Cys Cys Thr Ala Thr Ala Thr Gly Cys
    1310            1315            1320

Thr Gly Gly Ala Gly Ala Thr Gly Gly Ala Cys Ala Ala Cys Thr
    1325            1330            1335

Cys Ala Ala Thr Gly Ala Ala Ala Ala Thr Thr Thr Ala Ala Ala
    1340            1345            1350

Gly Gly Gly Ala Ala Ala Ala Cys Cys Cys Thr Cys Ala Gly Gly
    1355            1360            1365

Cys Cys Thr Gly Ala Gly Gly Thr Gly Thr Gly Thr Gly Cys Cys
    1370            1375            1380

Ala Cys Thr Cys Ala Gly Ala Gly Ala Cys Thr Thr Cys Ala Cys
    1385            1390            1395

Cys Thr Ala Ala Cys Thr Ala Gly Ala Gly Ala Cys Ala Gly Gly
    1400            1405            1410

Cys Ala Ala Ala Cys Thr Gly Cys Ala Ala Ala Cys Cys Ala Thr
    1415            1420            1425

Gly Gly Thr Gly Ala Gly Ala Ala Ala Thr Thr Gly Ala Cys Gly
    1430            1435            1440

Ala Cys Thr Thr Cys Ala Cys Ala Cys Thr Ala Thr Gly Gly Ala
    1445            1450            1455

Cys Ala Gly Cys Thr Thr Thr Cys Cys Cys Ala Ala Gly Ala
    1460            1465            1470

Thr Gly Thr Cys Ala Ala Ala Cys Ala Ala Gly Ala Cys Thr
    1475            1480            1485

Cys Cys Thr Cys Ala Thr Cys Ala Thr Gly Ala Thr Ala Ala Gly
    1490            1495            1500

Gly Cys Thr Cys Thr Thr Ala Cys Cys Cys Cys Cys Thr Thr Thr
    1505            1510            1515

Thr Ala Ala Thr Thr Thr Gly Thr Cys Cys Thr Thr Gly Cys Thr
    1520            1525            1530

Thr Ala Thr Gly Cys Cys Thr Gly Cys Cys Thr Cys Thr Thr Thr
    1535            1540            1545

Cys Gly Cys Thr Thr Gly Gly Cys Ala Gly Gly Ala Thr Gly Ala
    1550            1555            1560

Thr Gly Cys Thr Gly Thr Cys Ala Thr Thr Ala Gly Thr Ala Thr
    1565            1570            1575

Thr Thr Cys Ala Cys Ala Ala Gly Ala Ala Gly Thr Ala Gly Cys
    1580            1585            1590

Thr Thr Cys Ala Gly Ala Gly Gly Gly Thr Ala Ala Cys Thr Thr
    1595            1600            1605

Ala Ala Cys Ala Gly Ala Gly Thr Ala Thr Cys Ala Gly Ala Thr
    1610            1615            1620

Cys Thr Ala Thr Cys Thr Thr Gly Thr Cys Ala Ala Thr Cys Cys
    1625            1630            1635

Cys Ala Ala Cys Gly Thr Thr Thr Thr Ala Cys Ala Thr Ala Ala
    1640            1645            1650

Ala Ala Thr Ala Ala Gly Ala Gly Ala Thr Cys Cys Thr Thr Thr
    1655            1660            1665

Ala Gly Thr Gly Cys Ala Cys Cys Cys Ala Gly Thr Gly Ala Cys
    1670            1675            1680

Thr Gly Ala Cys Ala Thr Thr Ala Gly Cys Ala Gly Cys Ala Thr
    1685            1690            1695
```

```
Cys Thr Thr Thr Ala Ala Cys Ala Cys Ala Gly Cys Cys Gly Thr
    1700            1705                1710
Gly Thr Gly Thr Thr Cys Ala Ala Ala Thr Gly Thr Ala Cys Ala
    1715            1720                1725
Gly Thr Gly Gly Thr Cys Cys Thr Thr Thr Thr Cys Ala Gly Ala
    1730            1735                1740
Gly Thr Thr Gly Gly Ala Cys Thr Thr Cys Thr Ala Gly Ala Cys
    1745            1750                1755
Thr Cys Ala Cys Cys Thr Gly Thr Thr Cys Thr Cys Ala Cys Thr
    1760            1765                1770
Cys Cys Cys Thr Gly Thr Thr Thr Thr Ala Ala Thr Thr Cys Ala
    1775            1780                1785
Ala Cys Cys Cys Ala Gly Cys Cys Ala Thr Gly Cys Ala Ala Thr
    1790            1795                1800
Gly Cys Cys Ala Ala Ala Thr Ala Ala Thr Ala Gly Ala Ala Thr
    1805            1810                1815
Thr Gly Cys Thr Cys Cys Thr Ala Cys Cys Ala Gly Cys Gly Thr
    1820            1825                1830
Gly Ala Ala Cys Ala Gly Gly Ala Gly Gly Ala Gly Thr Cys
    1835            1840                1845
Thr Gly Thr Gly Cys Ala Gly Thr Thr Thr Cys Thr Gly Ala Cys
    1850            1855                1860
Ala Cys Thr Thr Gly Thr Thr Gly Thr Thr Gly Ala Ala Cys Ala
    1865            1870                1875
Thr Gly Gly Cys Thr Ala Ala Ala Thr Ala Cys Ala Ala Thr Gly
    1880            1885                1890
Gly Gly Thr Ala Thr Cys Gly Cys Thr Gly Ala Gly Ala Cys Thr
    1895            1900                1905
Ala Ala Gly Thr Thr Gly Thr Ala Gly Ala Ala Ala Thr Thr Ala
    1910            1915                1920
Ala Cys Ala Ala Ala Thr Gly Thr Gly Cys Thr Gly Cys Thr Thr
    1925            1930                1935
Gly Gly Thr Thr Ala Ala Ala Ala Thr Gly Gly Cys Thr Ala Cys
    1940            1945                1950
Ala Cys Thr Cys Ala Thr Cys Thr Gly Ala Cys Thr Cys Ala Thr
    1955            1960                1965
Thr Cys Thr Thr Thr Ala Thr Thr Cys Thr Ala Thr Thr Thr Thr
    1970            1975                1980
Ala Gly Thr Thr Gly Gly Thr Thr Gly Thr Ala Thr Cys Thr
    1985            1990                1995
Thr Gly Cys Cys Thr Ala Ala Gly Gly Thr Gly Cys Gly Thr Ala
    2000            2005                2010
Gly Thr Cys Cys Ala Ala Cys Thr Cys Thr Thr Gly Gly Thr Ala
    2015            2020                2025
Thr Thr Ala Cys Cys Cys Thr Cys Cys Thr Ala Ala Thr Ala Gly
    2030            2035                2040
Thr Cys Ala Thr Ala Cys Thr Ala Gly Thr Ala Gly Thr Cys Ala
    2045            2050                2055
Thr Ala Cys Thr Cys Cys Cys Thr Gly Gly Thr Gly Thr Ala Gly
    2060            2065                2070
Thr Gly Thr Ala Thr Thr Cys Thr Cys Thr Ala Ala Ala Ala Gly
    2075            2080                2085
Cys Thr Thr Thr Ala Ala Ala Thr Gly Thr Cys Thr Gly Cys Ala
```

-continued

|  | 2090 |  | 2095 |  | 2100 |  |
|---|---|---|---|---|---|---|

Thr Gly Cys Ala Gly Cys Cys Ala Gly Cys Cys Ala Thr Cys Ala
2105             2110             2115

Ala Ala Thr Ala Gly Thr Gly Ala Ala Thr Gly Gly Thr Cys Thr
2120             2125             2130

Cys Thr Cys Thr Thr Thr Gly Gly Cys Thr Gly Gly Ala Ala Thr
2135             2140             2145

Thr Ala Cys Ala Ala Ala Cys Thr Cys Ala Gly Ala Gly Ala
2150             2155             2160

Ala Ala Thr Gly Thr Gly Thr Cys Ala Thr Cys Ala Gly Gly Ala
2165             2170             2175

Gly Ala Ala Cys Ala Thr Cys Ala Thr Ala Ala Cys Cys Cys Ala
2180             2185             2190

Thr Gly Ala Ala Gly Gly Ala Thr Ala Ala Ala Gly Cys Cys
2195             2200             2205

Cys Cys Ala Ala Ala Thr Gly Gly Thr Gly Gly Thr Ala Ala Cys
2210             2215             2220

Thr Gly Ala Thr Ala Ala Thr Ala Gly Cys Ala Cys Thr Ala Ala
2225             2230             2235

Thr Gly Cys Thr Thr Thr Ala Ala Gly Ala Thr Thr Thr Gly Gly
2240             2245             2250

Thr Cys Ala Cys Ala Cys Thr Cys Thr Cys Ala Cys Cys Thr Ala
2255             2260             2265

Gly Gly Thr Gly Ala Gly Cys Gly Cys Ala Thr Gly Ala Gly
2270             2275             2280

Cys Cys Ala Gly Thr Gly Gly Thr Gly Cys Thr Ala Ala Ala Thr
2285             2290             2295

Gly Cys Thr Ala Cys Ala Thr Ala Cys Thr Cys Cys Ala Ala Cys
2300             2305             2310

Thr Gly Ala Ala Ala Thr Gly Thr Thr Ala Ala Gly Gly Ala Ala
2315             2320             2325

Gly Ala Ala Gly Ala Thr Ala Gly Ala Thr Cys Cys Ala Ala Thr
2330             2335             2340

Thr Ala Ala Ala Ala Ala Ala Ala Thr Thr Ala Ala Ala Ala
2345             2350             2355

Cys Cys Ala Ala Thr Thr Thr Ala Ala Ala Ala Ala Ala Ala Ala
2360             2365             2370

Ala Ala Ala Gly Ala Ala Cys Ala Cys Ala Gly Gly Ala Gly Ala
2375             2380             2385

Thr Thr Cys Cys Ala Gly Thr Cys Thr Ala Cys Thr Gly Ala
2390             2395             2400

Gly Thr Thr Ala Gly Cys Ala Thr Ala Ala Thr Ala Cys Ala Gly
2405             2410             2415

Ala Ala Gly Thr Cys Cys Cys Cys Thr Cys Thr Ala Cys Thr Thr
2420             2425             2430

Thr Ala Ala Cys Thr Thr Thr Thr Ala Cys Ala Ala Ala Ala Ala
2435             2440             2445

Ala Gly Thr Ala Ala Cys Cys Thr Gly Ala Ala Cys Thr Ala Ala
2450             2455             2460

Thr Cys Thr Gly Ala Thr Gly Thr Thr Ala Ala Cys Cys Ala Ala
2465             2470             2475

Thr Gly Thr Ala Thr Thr Thr Ala Thr Thr Thr Cys Thr Gly Thr
2480             2485             2490

```
Gly Gly Thr Thr Cys Thr Gly Thr Thr Thr Cys Cys Thr Thr Gly
        2495                2500                2505

Thr Thr Cys Cys Ala Ala Thr Thr Thr Gly Ala Cys Ala Ala Ala
        2510                2515                2520

Ala Cys Cys Cys Ala Cys Thr Gly Thr Thr Cys Thr Thr Gly Thr
        2525                2530                2535

Ala Thr Thr Gly Thr Ala Thr Thr Gly Cys Cys Ala Gly Gly
        2540                2545                2550

Gly Gly Gly Ala Gly Cys Thr Ala Thr Cys Ala Cys Thr Gly Thr
        2555                2560                2565

Ala Cys Thr Thr Gly Thr Ala Gly Ala Gly Thr Gly Gly Thr Gly
        2570                2575                2580

Cys Thr Gly Cys Thr Thr Thr Ala Ala Thr Thr Cys Ala Thr Ala
        2585                2590                2595

Ala Ala Thr Cys Ala Cys Ala Ala Ala Thr Ala Ala Ala Ala Gly
        2600                2605                2610

Cys Cys Ala Ala Thr Thr Ala Gly Cys Thr Cys Thr Ala Thr Ala
        2615                2620                2625

Ala Cys Thr
        2630

<210> SEQ ID NO 23
<211> LENGTH: 129
<212> TYPE: PRT
<213> ORGANISM: Artificial Sequence
<220> FEATURE:
<223> OTHER INFORMATION: CEACAM6 truncation construct (residues 191-320)

<400> SEQUENCE: 23

Leu Gln Leu Ser Asn Gly Asn Met Thr Leu Thr Leu Leu Ser Val Lys
1               5                   10                  15

Arg Asn Asp Ala Gly Ser Tyr Glu Cys Glu Ile Gln Asn Pro Ala Ser
            20                  25                  30

Ala Asn Arg Ser Asp Pro Val Thr Leu Asn Val Leu Tyr Gly Pro Asp
        35                  40                  45

Gly Pro Thr Ile Ser Pro Ser Lys Ala Asn Tyr Arg Pro Gly Glu Asn
    50                  55                  60

Leu Asn Leu Ser Cys His Ala Ala Ser Asn Pro Pro Ala Gln Tyr Ser
65                  70                  75                  80

Trp Phe Ile Asn Gly Thr Phe Gln Gln Ser Thr Gln Glu Leu Phe Ile
                85                  90                  95

Pro Asn Ile Thr Val Asn Asn Ser Gly Ser Tyr Met Cys Gln Ala His
            100                 105                 110

Asn Ser Ala Thr Gly Leu Asn Arg Thr Thr Val Thr Met Ile Thr Val
        115                 120                 125

Ser

<210> SEQ ID NO 24
<211> LENGTH: 130
<212> TYPE: PRT
<213> ORGANISM: Artificial Sequence
<220> FEATURE:
<223> OTHER INFORMATION: CEACAM5 truncation construct (residues 191-321)

<400> SEQUENCE: 24

Leu Gln Leu Ser Asn Gly Asn Arg Thr Leu Thr Leu Phe Asn Val Thr
1               5                   10                  15
```

-continued

Arg Asn Asp Thr Ala Ser Tyr Lys Cys Glu Thr Gln Asn Pro Val Ser
            20                  25                  30

Ala Arg Arg Ser Asp Ser Val Ile Leu Asn Val Leu Tyr Gly Pro Asp
        35                  40                  45

Ala Pro Thr Ile Ser Pro Leu Asn Thr Ser Tyr Arg Ser Gly Glu Asn
    50                  55                  60

Leu Asn Leu Ser Cys His Ala Ala Ser Asn Pro Pro Ala Gln Tyr Ser
65                  70                  75                  80

Trp Phe Val Asn Gly Thr Phe Gln Gln Ser Thr Gln Glu Leu Phe Ile
                85                  90                  95

Pro Asn Ile Thr Val Asn Ser Gly Ser Tyr Thr Cys Gln Ala His
            100                 105                 110

Asn Ser Asp Thr Gly Leu Asn Arg Thr Thr Val Thr Thr Ile Thr Val
            115                 120                 125

Tyr Ala
    130

<210> SEQ ID NO 25
<211> LENGTH: 130
<212> TYPE: PRT
<213> ORGANISM: Artificial Sequence
<220> FEATURE:
<223> OTHER INFORMATION: CEACAM8 truncation construct (residues 191-321)

<400> SEQUENCE: 25

Leu Gln Leu Ser Asn Gly Asn Arg Thr Leu Thr Leu Leu Ser Val Thr
1               5                   10                  15

Arg Asn Asp Val Gly Pro Tyr Glu Cys Glu Ile Gln Asn Pro Ala Ser
            20                  25                  30

Ala Asn Phe Ser Asp Pro Val Thr Leu Asn Val Leu Tyr Gly Pro Asp
        35                  40                  45

Ala Pro Thr Ile Ser Pro Ser Asp Thr Tyr Tyr His Ala Gly Val Asn
    50                  55                  60

Leu Asn Leu Ser Cys His Ala Ala Ser Asn Pro Pro Ser Gln Tyr Ser
65                  70                  75                  80

Trp Ser Val Asn Gly Thr Phe Gln Gln Tyr Thr Gln Lys Leu Phe Ile
                85                  90                  95

Pro Asn Ile Thr Thr Lys Asn Ser Gly Ser Tyr Ala Cys His Thr Thr
            100                 105                 110

Asn Ser Ala Thr Gly Arg Asn Arg Thr Thr Val Arg Met Ile Thr Val
            115                 120                 125

Ser Asp
    130

<210> SEQ ID NO 26
<211> LENGTH: 130
<212> TYPE: PRT
<213> ORGANISM: Artificial Sequence
<220> FEATURE:
<223> OTHER INFORMATION: CEACAM1 truncation construct (residues 191-321)

<400> SEQUENCE: 26

Leu Gln Leu Ser Asn Gly Asn Arg Thr Leu Thr Leu Leu Ser Val Thr
1               5                   10                  15

Arg Asn Asp Thr Gly Pro Tyr Glu Cys Glu Ile Gln Asn Pro Val Ser
            20                  25                  30

Ala Asn Arg Ser Asp Pro Val Thr Leu Asn Val Thr Tyr Gly Pro Asp

```
                35                  40                  45
Thr Pro Thr Ile Ser Pro Ser Asp Thr Tyr Tyr Arg Pro Gly Ala Asn
            50                  55                  60

Leu Ser Leu Ser Cys Tyr Ala Ala Ser Asn Pro Pro Ala Gln Tyr Ser
 65                  70                  75                  80

Trp Leu Ile Asn Gly Thr Phe Gln Gln Ser Thr Gln Glu Leu Phe Ile
                85                  90                  95

Pro Asn Ile Thr Val Asn Asn Ser Gly Ser Tyr Thr Cys His Ala Asn
            100                 105                 110

Asn Ser Val Thr Gly Cys Asn Arg Thr Thr Val Lys Thr Ile Ile Val
            115                 120                 125

Thr Glu
    130

<210> SEQ ID NO 27
<211> LENGTH: 8
<212> TYPE: PRT
<213> ORGANISM: Artificial Sequence
<220> FEATURE:
<223> OTHER INFORMATION: MUC5AC tandem repeat

<400> SEQUENCE: 27

Thr Thr Ser Thr Thr Ser Ala Pro
 1               5

<210> SEQ ID NO 28
<211> LENGTH: 8
<212> TYPE: PRT
<213> ORGANISM: Artificial Sequence
<220> FEATURE:
<223> OTHER INFORMATION: MUC5AC tandem repeat consensus peptide

<400> SEQUENCE: 28

Gly Ser Thr Pro Ser Pro Val Pro
 1               5

<210> SEQ ID NO 29
<211> LENGTH: 8
<212> TYPE: PRT
<213> ORGANISM: Artificial Sequence
<220> FEATURE:
<223> OTHER INFORMATION: MUC5AC tandem repeat consensus peptide

<400> SEQUENCE: 29

Thr Ala Ser Thr Thr Ser Gly Pro
 1               5

<210> SEQ ID NO 30
<211> LENGTH: 16
<212> TYPE: PRT
<213> ORGANISM: Artificial Sequence
<220> FEATURE:
<223> OTHER INFORMATION: MUC5AC O-glycosylation motiff

<400> SEQUENCE: 30

Gly Thr Thr Pro Ser Pro Val Pro Thr Thr Ser Thr Thr Ser Ala Pro
 1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: MUC5AC O-glycosylation motiff
```

-continued

<400> SEQUENCE: 31

Gly Thr Thr Pro Ser Ala Val Pro Thr Thr Ser Thr Ser Val Pro
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: MUC5AC O-glycosylation motiff

<400> SEQUENCE: 32

Gly Thr Thr Pro Ser Pro Val Pro Thr Thr Ser Ile Thr Ser Val Pro
1               5                   10                  15

<210> SEQ ID NO 33
<211> LENGTH: 11
<212> TYPE: PRT
<213> ORGANISM: Artificial Sequence
<220> FEATURE:
<223> OTHER INFORMATION: MUC5AC tandem repeat

<400> SEQUENCE: 33

Thr Thr Ser Thr Thr Ser Ala Pro Thr Thr Ser
1               5                   10

<210> SEQ ID NO 34
<211> LENGTH: 307
<212> TYPE: PRT
<213> ORGANISM: Artificial Sequence
<220> FEATURE:
<223> OTHER INFORMATION: NPC-1 antigen (variant 1)

<400> SEQUENCE: 34

Thr Thr His Ser Gln Pro Val Thr Arg Asp Cys His Leu Arg Cys Thr
1               5                   10                  15

Trp Thr Lys Trp Phe Asp Val Asp Phe Pro Ser Pro Gly Pro His Gly
            20                  25                  30

Gly Asp Lys Glu Thr Tyr Asn Asn Ile Ile Arg Ser Gly Glu Lys Ile
        35                  40                  45

Cys Arg Arg Pro Glu Glu Ile Thr Arg Leu Gln Cys Arg Ala Glu Ser
    50                  55                  60

His Pro Glu Val Ser Ile Glu His Leu Gly Gln Val Val Gln Cys Ser
65                  70                  75                  80

Arg Glu Glu Gly Leu Val Cys Arg Asn Gln Asp Gln Gln Gly Pro Phe
                85                  90                  95

Lys Met Cys Leu Asn Tyr Glu Val Arg Val Leu Cys Cys Glu Thr Pro
            100                 105                 110

Lys Gly Cys Pro Val Thr Ser Thr Pro Val Thr Ala Pro Ser Thr Pro
        115                 120                 125

Ser Gly Arg Ala Thr Ser Pro Thr Gln Ser Thr Ser Trp Gln Lys
    130                 135                 140

Ser Arg Thr Thr Thr Leu Val Thr Thr Ser Thr Ser Thr Pro Gln
145                 150                 155                 160

Thr Ser Thr Thr Ser Ala Pro Thr Thr Ser Thr Thr Ser Ala Pro Thr
                165                 170                 175

Thr Ser Thr Thr Ser Ala Pro Thr Thr Ser Thr Thr Ser Thr Pro Gln
            180                 185                 190

Thr Ser Ile Ser Ser Ala Pro Thr Ser Ser Thr Thr Ser Ala Pro Thr

```
              195                 200                 205
Ser Ser Thr Ile Ser Ala Arg Thr Thr Ser Ile Ile Ser Ala Pro Thr
210                 215                 220

Thr Ser Thr Thr Ser Ser Pro Thr Thr Ser Thr Thr Ser Ala Thr Thr
225                 230                 235                 240

Thr Ser Thr Thr Ser Ala Pro Thr Ser Ser Thr Thr Ser Thr Pro Gln
                245                 250                 255

Thr Ser Lys Thr Ser Ala Ala Thr Ser Ser Thr Ser Ser Ser Ser Gly
            260                 265                 270

Thr Thr Pro Ser Pro Val Thr Thr Thr Ser Thr Ala Ser Val Ser Lys
            275                 280                 285

Thr Ser Thr Ser His Val Ser Val Ser Lys Thr Thr His Ser Gln Pro
            290                 295                 300

Val Thr Arg
305

<210> SEQ ID NO 35
<211> LENGTH: 281
<212> TYPE: PRT
<213> ORGANISM: Artificial Sequence
<220> FEATURE:
<223> OTHER INFORMATION: NPC-1 antigen (variant 2)

<400> SEQUENCE: 35

Gly Thr His Thr Thr Pro Val Thr Arg Asn Cys His Pro Arg Cys Thr
1               5                   10                  15

Trp Thr Lys Trp Phe Asp Val Asp Phe Pro Ser Pro Gly Pro His Gly
            20                  25                  30

Gly Asp Lys Glu Thr

```
                    245                 250                 255
Thr Ser Thr Thr Ser Ala Pro Thr Thr Ser Thr Thr Ser Gly Pro Gly
                260                 265                 270
Thr Thr Pro Ser Pro Val Pro Thr Thr
            275                 280

<210> SEQ ID NO 36
<211> LENGTH: 16
<212> TYPE: PRT
<213> ORGANISM: Artificial Sequence
<220> FEATURE:
<223> OTHER INFORMATION: MUC5AC NPC-1 epitope (1)

<400> SEQUENCE: 36

Thr Thr Ser Thr Thr Ser Ala Pro Thr Thr Ser Thr Thr Ser Ala Pro
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: MUC5AC NPC-1 epitope (2)

<400> SEQUENCE: 37

Gly Cys Pro Val Thr Ser Thr Pro Val Thr Ala Pro Ser Thr Pro
1               5                   10                  15

<210> SEQ ID NO 38
<211> LENGTH: 424
<212> TYPE: PRT
<213> ORGANISM: Homo sapiens

<400> SEQUENCE: 38

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
                20                  25                  30

Thr Ala Gln Leu Thr Thr Glu Ser Met Pro Phe Asn Val Ala Glu Gly
            35                  40                  45

Lys Glu Val Leu Leu Leu Val His Asn Leu Pro Gln Gln Leu Phe Gly
        50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
```

```
            195                 200                 205
Asp Thr Gly Pro Tyr Glu Cys Glu Ile Gln Asn Pro Val Ser Ala Asn
210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Asn Ala Leu Pro Gln Glu Asn Gly
370                 375                 380

Leu Ser Pro Gly Ala Ile Ala Gly Ile Val Ile Gly Val Val Ala Leu
385                 390                 395                 400

Val Ala Leu Ile Ala Val Ala Leu Ala Cys Phe Leu His Phe Gly Lys
                405                 410                 415

Thr Gly Ser Ser Gly Pro Leu Gln
            420

<210> SEQ ID NO 39
<211> LENGTH: 349
<212> TYPE: PRT
<213> ORGANISM: Homo sapiens

<400> SEQUENCE: 39

Met Gly Pro Ile Ser Ala Pro Ser Cys Arg Trp Arg Ile Pro Trp Gln
1               5                   10                  15

Gly Leu Leu Leu Thr Ala Ser Leu Phe Thr Phe Trp Asn Pro Pro Thr
                20                  25                  30

Thr Ala Gln Leu Thr Ile Glu Ala Val Pro Ser Asn Ala Ala Glu Gly
            35                  40                  45

Lys Glu Val Leu Leu Val His Asn Leu Pro Gln Asp Pro Arg Gly
50                  55                  60

Tyr Asn Trp Tyr Lys Gly Glu Thr Val Asp Ala Asn Arg Arg Ile Ile
65                  70                  75                  80

Gly Tyr Val Ile Ser Asn Gln Gln Ile Thr Pro Gly Pro Ala Tyr Ser
                85                  90                  95

Asn Arg Glu Thr Ile Tyr Pro Asn Ala Ser Leu Leu Met Arg Asn Val
            100                 105                 110

Thr Arg Asn Asp Thr Gly Ser Tyr Thr Leu Gln Val Ile Lys Leu Asn
        115                 120                 125

Leu Met Ser Glu Glu Val Thr Gly Gln Phe Ser Val His Pro Glu Thr
130                 135                 140
```

```
Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Val Gly Pro Tyr Glu Cys Glu Ile Gln Asn Pro Ala Ser Ala Asn
    210                 215                 220

Phe Ser Asp Pro Val Thr Leu Asn Val Leu Tyr Gly Pro Asp Ala Pro
225                 230                 235                 240

Thr Ile Ser Pro Ser Asp Thr Tyr Tyr His Ala Gly Val Asn Leu Asn
                245                 250                 255

Leu Ser Cys His Ala Ala Ser Asn Pro Pro Ser Gln Tyr Ser Trp Ser
            260                 265                 270

Val Asn Gly Thr Phe Gln Gln Tyr Thr Gln Lys Leu Phe Ile Pro Asn
        275                 280                 285

Ile Thr Thr Lys Asn Ser Gly Ser Tyr Ala Cys His Thr Asn Ser
290                 295                 300

Ala Thr Gly Arg Asn Arg Thr Thr Val Arg Met Ile Thr Val Ser Asp
305                 310                 315                 320

Ala Leu Val Gln Gly Ser Ser Pro Gly Leu Ser Ala Arg Ala Thr Val
                325                 330                 335

Ser Ile Met Ile Gly Val Leu Ala Arg Val Ala Leu Ile
            340                 345
```

<210> SEQ ID NO 40
<211> LENGTH: 92
<212> TYPE: PRT
<213> ORGANISM: Artificial Sequence
<220> FEATURE:
<223> OTHER INFORMATION: CEACAM5 16C3 epitope
<220> FEATURE:
<221> NAME/KEY: MISC_FEATURE
<222> LOCATION: (8)..(67)
<223> OTHER INFORMATION: Xaa can be any amino acid

<400> SEQUENCE: 40

```
Gly Pro Asp Ala Pro Thr Ile Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Gly Ser Tyr Thr Cys Gln Ala His Asn Ser Asp Thr Gly
65                  70                  75                  80

Leu Asn Arg Thr Thr Val Thr Ile Thr Val Tyr
            85                  90
```

<210> SEQ ID NO 41
<211> LENGTH: 7
<212> TYPE: PRT
<213> ORGANISM: Artificial Sequence
<220> FEATURE:
<223> OTHER INFORMATION: CEACAM 16C3 epitope N-terminal flanking peptide

```
<400> SEQUENCE: 41

Gly Pro Asp Ala Pro Thr Ile
1               5

<210> SEQ ID NO 42
<211> LENGTH: 25
<212> TYPE: PRT
<213> ORGANISM: Artificial Sequence
<220> FEATURE:
<223> OTHER INFORMATION: CEACAM5 16C3 C-terminal flanking peptide

<400> SEQUENCE: 42

Gly Ser Tyr Thr Cys Gln Ala His Asn Ser Asp Thr Gly Leu Asn Arg
1               5                   10                  15

Thr Thr Val Thr Thr Ile Thr Val Tyr
            20                  25

<210> SEQ ID NO 43
<211> LENGTH: 92
<212> TYPE: PRT
<213> ORGANISM: Artificial Sequence
<220> FEATURE:
<223> OTHER INFORMATION: CEACAM6 16C3 epitope
<220> FEATURE:
<221> NAME/KEY: MISC_FEATURE
<222> LOCATION: (8)..(67)
<223> OTHER INFORMATION: Xaa can be any amino acid

<400> SEQUENCE: 43

Gly Pro Asp Gly Pro Thr Ile Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Gly Ser Tyr Met Cys Gln Ala His Asn Ser Ala Thr Gly
65                  70                  75                  80

Leu Asn Arg Thr Thr Val Thr Met Ile Thr Val Ser
                85                  90

<210> SEQ ID NO 44
<211> LENGTH: 25
<212> TYPE: PRT
<213> ORGANISM: Artificial Sequence
<220> FEATURE:
<223> OTHER INFORMATION: CEACAM6 C-terminal flanking peptide

<400> SEQUENCE: 44

Gly Ser Tyr Met Cys Gln Ala His Asn Ser Ala Thr Gly Leu Asn Arg
1               5                   10                  15

Thr Thr Val Thr Met Ile Thr Val Ser
            20                  25

<210> SEQ ID NO 45
<211> LENGTH: 319
<212> TYPE: PRT
<213> ORGANISM: Homo sapiens

<400> SEQUENCE: 45

Met Val Gly Lys Met Trp Pro Val Leu Trp Thr Leu Cys Ala Val Arg
1               5                   10                  15
```

```
Val Thr Val Asp Ala Ile Ser Val Glu Thr Pro Gln Asp Val Leu Arg
        20                  25                  30

Ala Ser Gln Gly Lys Ser Val Thr Leu Pro Cys Thr Tyr His Thr Ser
            35                  40                  45

Thr Ser Ser Arg Glu Gly Leu Ile Gln Trp Asp Lys Leu Leu Leu Thr
 50                      55                  60

His Thr Glu Arg Val Val Ile Trp Pro Phe Ser Asn Lys Asn Tyr Ile
 65                  70                  75                  80

His Gly Glu Leu Tyr Lys Asn Arg Val Ser Ile Ser Asn Asn Ala Glu
                85                  90                  95

Gln Ser Asp Ala Ser Ile Thr Ile Asp Gln Leu Thr Met Ala Asp Asn
            100                 105                 110

Gly Thr Tyr Glu Cys Ser Val Ser Leu Met Ser Asp Leu Glu Gly Asn
            115                 120                 125

Thr Lys Ser Arg Val Arg Leu Leu Val Leu Val Pro Pro Ser Lys Pro
130                     135                 140

Glu Cys Gly Ile Glu Gly Glu Thr Ile Ile Gly Asn Asn Ile Gln Leu
145                 150                 155                 160

Thr Cys Gln Ser Lys Glu Gly Ser Pro Thr Pro Gln Tyr Ser Trp Lys
                165                 170                 175

Arg Tyr Asn Ile Leu Asn Gln Glu Gln Pro Leu Ala Gln Pro Ala Ser
            180                 185                 190

Gly Gln Pro Val Ser Leu Lys Asn Ile Ser Thr Asp Thr Ser Gly Tyr
            195                 200                 205

Tyr Ile Cys Thr Ser Ser Asn Glu Glu Gly Thr Gln Phe Cys Asn Ile
            210                 215                 220

Thr Val Ala Val Arg Ser Pro Ser Met Asn Val Ala Leu Tyr Val Gly
225                 230                 235                 240

Ile Ala Val Gly Val Val Ala Ala Leu Ile Ile Ile Gly Ile Ile Ile
                245                 250                 255

Tyr Cys Cys Cys Cys Arg Gly Lys Asp Asp Asn Thr Glu Asp Lys Glu
            260                 265                 270

Asp Ala Arg Pro Asn Arg Glu Ala Tyr Glu Glu Pro Pro Glu Gln Leu
            275                 280                 285

Arg Glu Leu Ser Arg Glu Arg Glu Glu Asp Tyr Arg Gln Glu
290                 295                 300

Glu Gln Arg Ser Thr Gly Arg Glu Ser Pro Asp His Leu Asp Gln
305                 310                 315

<210> SEQ ID NO 46
<211> LENGTH: 56
<212> TYPE: PRT
<213> ORGANISM: Artificial Sequence
<220> FEATURE:
<223> OTHER INFORMATION: A33 antigen mass spec fragment 1

<400> SEQUENCE: 46

Ala Ser Gln Gly Lys Ser Val Thr Leu Pro Cys Thr Tyr His Thr Ser
 1               5                  10                  15

Thr Ser Ser Arg Glu Gly Leu Ile Gln Trp Asp Lys Leu Leu Leu Thr
                20                  25                  30

His Thr Glu Arg Val Val Ile Trp Pro Phe Ser Asn Lys Asn Tyr Ile
            35                  40                  45

His Gly Glu Leu Tyr Lys Asn Arg
        50                  55
```

```
<210> SEQ ID NO 47
<211> LENGTH: 67
<212> TYPE: PRT
<213> ORGANISM: Artificial Sequence
<220> FEATURE:
<223> OTHER INFORMATION: A33 antigen mass spec fragment 2

<400> SEQUENCE: 47

Val Arg Leu Leu Val Leu Val Pro Pro Ser Lys Pro Glu Cys Gly Ile
1               5                   10                  15

Glu Gly Glu Thr Ile Ile Gly Asn Asn Ile Gln Leu Thr Cys Gln Ser
            20                  25                  30

Lys Glu Gly Ser Pro Thr Pro Gln Tyr Ser Trp Lys Arg Tyr Asn Ile
        35                  40                  45

Leu Asn Gln Glu Gln Pro Leu Ala Gln Pro Ala Ser Gly Gln Pro Val
    50                  55                  60

Ser Leu Lys
65

<210> SEQ ID NO 48
<211> LENGTH: 55
<212> TYPE: PRT
<213> ORGANISM: Artificial Sequence
<220> FEATURE:
<223> OTHER INFORMATION: A33 antigen mass spec fragment 3

<400> SEQUENCE: 48

Asp Asp Asn Thr Glu Asp Lys Glu Asp Ala Arg Pro Asn Arg Glu Ala
1               5                   10                  15

Tyr Glu Pro Pro Glu Gln Leu Arg Glu Leu Ser Arg Glu Arg Glu
            20                  25                  30

Glu Glu Asp Asp Tyr Arg Gln Glu Gln Arg Ser Thr Gly Arg Glu
        35                  40                  45

Ser Pro Asp His Leu Asp Gln
    50                  55

<210> SEQ ID NO 49
<211> LENGTH: 15
<212> TYPE: PRT
<213> ORGANISM: Artificial Sequence
<220> FEATURE:
<223> OTHER INFORMATION: Synthetic peptide

<400> SEQUENCE: 49

Phe Ser Asn Lys Asn Tyr Ile His Gly Glu Leu Tyr Lys Asn Arg
1               5                   10                  15

<210> SEQ ID NO 50
<211> LENGTH: 19
<212> TYPE: PRT
<213> ORGANISM: Artificial Sequence
<220> FEATURE:
<223> OTHER INFORMATION: 31.1 epitope

<400> SEQUENCE: 50

Ser Pro Thr Pro Gln Tyr Ser Trp Lys Arg Tyr Asn Ile Leu Asn Gln
1               5                   10                  15

Glu Gln Pro

<210> SEQ ID NO 51
<211> LENGTH: 965
```

```
<212> TYPE: DNA
<213> ORGANISM: Artificial Sequence
<220> FEATURE:
<223> OTHER INFORMATION: NPC-1 antibody light chain

<400> SEQUENCE: 51
atgagaatac cattaattag ctagggacca aaattcaaag acaaaatgga ttttcaggtg      60
cagattttca gcttcctgct aatcagtgcc tcagtcatac tgtccagagg acaagttgtt     120
ctcacccagt ctccagtaat catgtctgca tctccagggg agaaggtcac catgacctgc     180
agtgccagct caagtataag ttacatgtac tggtaccagc agaagccagg cacctccccc     240
aaaagatgga tttatgacac atccaaactg gcttctggag tccctgctcg cttcagtggc     300
agtgggtctg ggacctctta ttctctcaca atcagcaaca tggaggctgg agatgctgcc     360
acttattact gccatcagcg ggattcttac ccatggacgt tcggtggagg caccaacctg     420
gaaatcaaac gggctgatgc tgcaccaact gtatccatct cccaccatc cagtgagcag       480 ttaacatctg gaggtgcctc agtcgtgtgc ttcttgaaca acttctaccc caaagacatc     540
aatgtcaagt ggaagattga tggcagtgaa cgacaaaatg gcgtcctgaa cagttggact     600
gatcaggaca gcaaagacag cacctacagc atgagcagca ccctcacgtt gaccaaggac     660
gagtatgaac gacataacag ctatacctgt gaggccactc acaagacatc aacttcaccc     720
attgtcaaga gcttcaacag gaatgagtgt tagagacaaa ggtcctgaga cgccaccacc     780
agctccccag ctccatccta tcttcccttc taaggtcttg gaggcttccc cacaagcgac     840
ctaccactgt tgcggtgctc caaacctcct ccccacctcc ttctcctcct cctcccttc     900 cttggctttt atcatgctaa tatttgcaga aaatattcaa taaagtgagt ctttgcactt     960
gaaaa                                                                  965

<210> SEQ ID NO 52
<211> LENGTH: 235
<212> TYPE: PRT
<213> ORGANISM: Artificial Sequence
<220> FEATURE:
<223> OTHER INFORMATION: NPC-1 antibody light chain
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (110)..(118)
<223> OTHER INFORMATION: CDR3

<400> SEQUENCE: 52

Met Asp Phe Gln Val Gln Ile Phe Ser Phe Leu Leu Ile Ser Ala Ser
1               5                   10                  15

Val Ile Leu Ser Arg Gly Gln Val Val Leu Thr Gln Ser Pro Val Ile
            20                  25                  30

Met Ser Ala Ser Pro Gly Glu Lys Val Thr Met Thr Cys Ser Ala Ser
        35                  40                  45

Ser Ser Ile Ser Tyr Met Tyr Trp Tyr Gln Gln Lys Pro Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
```

```
                85                  90                  95
Ser Asn Met Glu Ala Gly Asp Ala Ala Thr Tyr Tyr Cys His Gln Arg
            100                 105                 110

Asp Ser Tyr Pro Trp Thr Phe Gly Gly Gly Thr Asn Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 53
<211> LENGTH: 10
<212> TYPE: PRT
<213> ORGANISM: Artificial Sequence
<220> FEATURE:
<223> OTHER INFORMATION: NPC-1 light chain CDR1

<400> SEQUENCE: 53

```
Ser Ala Ser Ser Ser Ile Ser Tyr Met Tyr
1               5                   10
```

<210> SEQ ID NO 54
<211> LENGTH: 7
<212> TYPE: PRT
<213> ORGANISM: Artificial Sequence
<220> FEATURE:
<223> OTHER INFORMATION: NPC-1 light chain CDR2

<400> SEQUENCE: 54

```
Asp Thr Ser Lys Leu Ala Ser
1               5
```

<210> SEQ ID NO 55
<211> LENGTH: 9
<212> TYPE: PRT
<213> ORGANISM: Artificial Sequence
<220> FEATURE:
<223> OTHER INFORMATION: NPC-1 antibody light chain CDR3

<400> SEQUENCE: 55

```
His Gln Arg Asp Ser Tyr Pro Trp Thr
1               5
```

<210> SEQ ID NO 56
<211> LENGTH: 1520
<212> TYPE: DNA
<213> ORGANISM: Artificial Sequence
<220> FEATURE:
<223> OTHER INFORMATION: NPC-1 antibody heavy chain

<400> SEQUENCE: 56

```
ttttccatcc tcttctcata gagcctccat cagaccatgg ctgtcctggc actgctcctc      60
```

```
tgcctggtga cattcccaag ctgtgtcctg tcccaggtgc agctgaagga gtcaggacct    120
gacctggtgg cgccctcaca gagcctgtcc atcacatgca ctgtctcagg attctcatta    180
agcaaatttg gtgtaaactg ggttcgccag cctccaggaa agggtctgga gtggctggga    240
gtaatatggg gtgacgggag cacaagttat aattcaggtc tcatatcaag actgagcatc    300
agcaaggaga actccaagag ccaggttttc ttaaaactga acagtctgca agctgatgac    360
acagccacat actactgtgt caaaccgggg ggtgactact ggggtcacgg aacctcagtc    420
accgtctcct cagccaaaac gacaccccca tctgtctatc cactggcccc tggatctgct    480
gcccaaacta actccatggt gaccctggga tgcctggtca agggctattt ccctgagcca    540
gtgacagtga cctggaactc tggatccctg tccagcggtg tgcacacctt cccagctgtc    600
ctgcagtctg acctctacac tctgagcagc tcagtgactg tcccctccag cacctggccc    660
agcgagaccg tcacctgcaa cgttgcccac ccggccagca gcaccaaggt ggacaagaaa    720
attgtgccca gggattgtgg ttgtaagcct tgcatatgta cagtcccaga agtatcatct    780
gtcttcatct tccccccaaa gcccaaggat gtgctcacca ttactctgac tcctaaggtc    840
acgtgtgttg tggtagacat cagcaaggat gatcccgagg tccagttcag ctggtttgta    900
gatgtggagg tgcacacagc tcagacgcaa ccccgggagg agcagttcaa cagcactttc    960
cgctcagtca gtgaacttcc catcatgcac caggactggc tcaatggcaa ggagttcaaa   1020
tgcagggtca acagtgcagc tttccctgcc cccatcgaga aaaccatctc caaaaccaaa   1080
ggcagaccga aggctccaca ggtgtacacc attccacctc caaggagca  gatggccaag   1140 gataaagtca gtctgacctg catgataaca gacttcttcc ctgaagacat tactgtggag   1200
tggcagtgga tgggcagcc  agcggagaac tacaagaaca ctcagcccat catggacaca   1260
gatggctctt acttcgtcta cagcaagctc aatgtgcaga gagcaactg  ggaggcagga   1320 aatactttca cctgctctgt gttacatgag ggcctgcaca accaccatac tgagaagagc   1380
ctctcccact ctcctggtaa atgatcccag tgtccttgga gccctctggt cctacaggac   1440
tctgacacct acctccaccc ctccctgtat aaataaagca cccagcactg ccttgggacc   1500
ctgcaaaaaa aaaaaaaaa                                              1520
```

<210> SEQ ID NO 57
<211> LENGTH: 456
<212> TYPE: PRT
<213> ORGANISM: Artificial Sequence
<220> FEATURE:
<223> OTHER INFORMATION: NPC-1 antibody heavy chain
<220> FEATURE:
<221> NAME/KEY: MISC_FEATURE
<222> LOCATION: (49)..(54)
<223> OTHER INFORMATION: CDR1
<220> FEATURE:
<221> NAME/KEY: MISC_FEATURE
<222> LOCATION: (69)..(84)
<223> OTHER INFORMATION: CDR2
<220> FEATURE:
<221> NAME/KEY: MISC_FEATURE
<222> LOCATION: (114)..(121)
<223> OTHER INFORMATION: CDR3

<400> SEQUENCE: 57

Met Ala Val Leu Ala Leu Leu Leu Cys Leu Val Thr Phe Pro Ser Cys
1               5                   10                  15

Val Leu Ser Gln Val Gln Leu Lys Glu Ser Gly Pro Asp Leu Val Ala
            20                  25                  30

```
Pro Ser Gln Ser Leu Ser Ile Thr Cys Thr Val Ser Gly Phe Ser Leu
            35                  40                  45

Ser Lys Phe Gly Val Asn Trp Val Arg Gln Pro Pro Gly Lys Gly Leu
 50                  55                  60

Glu Trp Leu Gly Val Ile Trp Gly Asp Gly Ser Thr Ser Tyr Asn Ser
 65                  70                  75                  80

Gly Leu Ile Ser Arg Leu Ser Ile Ser Lys Glu Asn Ser Lys Ser Gln
                 85                  90                  95

Val Phe Leu Lys Leu Asn Ser Leu Gln Ala Asp Asp Thr Ala Thr Tyr
                100                 105                 110

Tyr Cys Val Lys Pro Gly Gly Asp Tyr Trp Gly His Gly Thr Ser Val
            115                 120                 125

Thr Val Ser Ser Ala Lys Thr Thr Pro Pro Ser Val Tyr Pro Leu Ala
130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Thr Trp Pro
            195                 200                 205

Ser Glu Thr Val Thr Cys Asn Val Ala His Pro Ala Ser Ser Thr Lys
210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Lys Asp Val Leu Thr Ile Thr Leu Thr Pro Lys Val Thr Cys Val Val
            260                 265                 270

Val Asp Ile Ser Lys Asp Asp Pro Glu Val Gln Phe Ser Trp Phe Val
            275                 280                 285

Asp Asp Val Glu Val His Thr Ala Gln Thr Gln Pro Arg Glu Glu Gln
290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
            340                 345                 350

Lys Ala Pro Gln Val Tyr Thr Ile Pro Pro Lys Glu Gln Met Ala
            355                 360                 365

Lys Asp Lys Val Ser Leu Thr Cys Met Ile Thr Asp Phe Phe Pro Glu
370                 375                 380

Asp Ile Thr Val Glu Trp Gln Trp Asn Gly Gln Pro Ala Glu Asn Tyr
385                 390                 395                 400

Lys Asn Thr Gln Pro Ile Met Asp Thr Asp Gly Ser Tyr Phe Val Tyr
                405                 410                 415

Ser Lys Leu Asn Val Gln Lys Ser Asn Trp Glu Ala Gly Asn Thr Phe
            420                 425                 430

Thr Cys Ser Val Leu His Glu Gly Leu His Asn His His Thr Glu Lys
            435                 440                 445

Ser Leu Ser His Ser Pro Gly Lys
```

<210> SEQ ID NO 58
<211> LENGTH: 6
<212> TYPE: PRT
<213> ORGANISM: Artificial Sequence
<220> FEATURE:
<223> OTHER INFORMATION: NPC-1 antibody heavy chain CDR1

<400> SEQUENCE: 58

Ser Lys Phe Gly Val Asn
1               5

<210> SEQ ID NO 59
<211> LENGTH: 16
<212> TYPE: PRT
<213> ORGANISM: Artificial Sequence
<220> FEATURE:
<223> OTHER INFORMATION: NPC-1 heavy chain CDR2

<400> SEQUENCE: 59

Val Ile Trp Gly Asp Gly Ser Thr Ser Tyr Asn Ser Gly Leu Ile Ser
1               5                   10                  15

<210> SEQ ID NO 60
<211> LENGTH: 8
<212> TYPE: PRT
<213> ORGANISM: Artificial Sequence
<220> FEATURE:
<223> OTHER INFORMATION: NPC-1 antibody heavy chain CDR3

<400> SEQUENCE: 60

Cys Val Lys Pro Gly Gly Asp Tyr
1               5

<210> SEQ ID NO 61
<211> LENGTH: 737
<212> TYPE: DNA
<213> ORGANISM: Artificial Sequence
<220> FEATURE:
<223> OTHER INFORMATION: NPC-1 Chi-antibody light chain

<400> SEQUENCE: 61
gcatagatct gccaccatgg actttcaggt ccagatattt agctttctat tgattagcgc      60
ctctgtcatt ctgagtaggg ggcaggtggt gctcacccag tctccagtga tcatgtcagc     120
ctcaccagga gaaaaagtga ctatgacctg ctcagcatcc tccagcatca gttacatgta     180
ctggtaccag cagaagccag gcacctcgcc caagcgttgg atctacgata cttccaagct     240
ggcaagtggg gtacccgcac gcttcagtgg aagtggctcc ggaacctcgt acagtttgac     300
catttcaaat atggaagctg ggacgcagc tacatattat tgccaccaga gagactccta     360
cccgtggacc ttcggaggcg gtactaattt agagatcaag aggaccgtag ccgctccttc     420
cgtgttcatc tttccccctt ccgacgaaca actgaaaagc ggtacagcct ccgtggtttg     480
tctgctgaac aacttctacc cccgggaggc taaagttcag tggaaggttg acaatgctct     540
gcagtcaggc aactctcaag agagcgtcac ggagcaagat agcaaagatt ctacatattc     600
tctctcttct acacttacac ttagcaaggc cgattatgag aagcacaagg tgtatgcctg     660
cgaggtgact catcagggtc tttcttctcc tgtcactaaa agcttcaacc gaggcgaatg     720
ttgatgaaga tcttacg                                                    737

<210> SEQ ID NO 62

```
<211> LENGTH: 235
<212> TYPE: PRT
<213> ORGANISM: Artificial Sequence
<220> FEATURE:
<223> OTHER INFORMATION: NPC-1 chi-antibody light chain with signal
      peptide
<220> FEATURE:
<221> NAME/KEY: SIGNAL
<222> LOCATION: (1)..(22)
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (110)..(118)
<223> OTHER INFORMATION: CDR3

<400> SEQUENCE: 62

Met Asp Phe Gln Val Gln Ile Phe Ser Phe Leu Leu Ile Ser Ala Ser
1               5                   10                  15

Val Ile Leu Ser Arg Gly Gln Val Val Leu Thr Gln Ser Pro Val Ile
            20                  25                  30

Met Ser Ala Ser Pro Gly Glu Lys Val Thr Met Thr Cys Ser Ala Ser
        35                  40                  45

Ser Ser Ile Ser Tyr Met Tyr Trp Tyr Gln Gln Lys Pro Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Asn Met Glu Ala Gly Asp Ala Ala Thr Tyr Tyr Cys His Gln Arg
            100                 105                 110

Asp Ser Tyr Pro Trp Thr Phe Gly Gly Gly Thr Asn Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 63
<211> LENGTH: 10
<212> TYPE: PRT
<213> ORGANISM: Artificial Sequence
<220> FEATURE:
<223> OTHER INFORMATION: NPC-1 chi-antibody light chain CDR1

<400> SEQUENCE: 63
```

Ser Ala Ser Ser Ser Ile Ser Tyr Met Tyr
1               5                   10

<210> SEQ ID NO 64
<211> LENGTH: 7
<212> TYPE: PRT
<213> ORGANISM: Artificial Sequence
<220> FEATURE:
<223> OTHER INFORMATION: NPC-1 chi-antibody light chain CDR2

<400> SEQUENCE: 64

Asp Thr Ser Lys Leu Ala Ser
1               5

<210> SEQ ID NO 65
<211> LENGTH: 9
<212> TYPE: PRT
<213> ORGANISM: Artificial Sequence
<220> FEATURE:
<223> OTHER INFORMATION: NPC-1 chi-antibody light chain CDR3

<400> SEQUENCE: 65

His Gln Arg Asp Ser Tyr Pro Trp Thr
1               5

<210> SEQ ID NO 66
<211> LENGTH: 1418
<212> TYPE: DNA
<213> ORGANISM: Artificial Sequence
<220> FEATURE:
<223> OTHER INFORMATION: NPC-1 chi-antibody heavy chain

<400> SEQUENCE: 66

| | | | | |
|---|---|---|---|---|
| gagcggtacc | gccaccatgg | cagtgctggc | ccttcttcta | tgtctggtga | ccttcccatc | 60 |
| ctgcgtcctg | agccaggtac | aactgaagga | gtcgggccca | gacctagtgg | ctccgtcaca | 120 |
| atcactctcc | attacgtgca | ctgtctccgg | cttctctttg | tctaaattcg | gcgtgaattg | 180 |
| ggtgcgacag | ccccccggga | aggggcttga | gtggttagga | gttatctggg | gtgacggctc | 240 |
| aaccagctac | aactcaggac | taatctcacg | cttgtcaatt | caaggagaa | ttcaaagtc | 300 |
| tcaggtgttc | cttaagctca | actcgctgca | agccgacgat | accgcaacct | attactgcgt | 360 |
| caaacctggc | ggggactact | ggggccatgg | cacctccgtc | acagtgagtt | ccgcatccac | 420 |
| aaagggtccc | agtgtttttc | ctttggcgcc | ctctagcaaa | tcgacatctg | gcggcacagc | 480 |
| cgcacttggg | tgcttggtta | aagactactt | ccccgaaccg | gtgacagtat | cttggaactc | 540 |
| tggcgctctt | accagcggag | ttcatacctt | ccctgccgta | ttacagtcta | gcgggcccta | 600 |
| ctccctctcc | tctgtcgtga | cagtcccaag | ctcttctctg | gaactcaaa | cctacatctg | 660 |
| caatgtgaac | cataaaccta | gcaacacgaa | agtggacaaa | aaggtcgaac | ccaagagttg | 720 |
| cgacaagaca | cacacctgcc | ctccttgtcc | tgctccagag | ctcctcggcg | gacctagcgt | 780 |
| tttcttgttc | cctccgaaac | caaggacac | cttgatgatt | tctcggaccc | ccgaggtgac | 840 |
| atgtgtagta | gttgatgtct | cccacgagga | ccctgaggtc | aagtttaatt | ggtatgtgga | 900 |
| cggtgtggag | gtccacaacg | ccaaaacaaa | accacgggag | gaacagtaca | attccacata | 960 |
| tagggtggtg | agcgtcctta | ccgtcctgca | tcaggattgg | ttaaatggta | aggagtataa | 1020 |
| gtgtaaggtg | tctaacaagg | ctctgcctgc | tcccatcgaa | aaaactataa | gtaaggccaa | 1080 |
| aggacagccc | agggaacctc | aggtgtatac | tcttccaccc | agtagagatg | agctgactaa | 1140 |
| aaaccaggtg | tccctgactt | gtctggtgaa | gggattttac | ccatccgata | tcgccgtgga | 1200 |

-continued

```
atgggagtcc aacggacagc cagaaaacaa ttataaaact atgccaccag tgctggatag    1260
tgatggtagt ttttttctgt acagtaagct gactgttgat aagagtagat ggcagcaggg    1320
taatgttttt agttgtagcg ttatgcacga agctctgcac aatcactata ctcagaagag    1380
cctgagcctg agccccggta agtgatgagg taccgagc                            1418
```

```
<210> SEQ ID NO 67
<211> LENGTH: 462
<212> TYPE: PRT
<213> ORGANISM: Artificial Sequence
<220> FEATURE:
<223> OTHER INFORMATION: NPC-1 chi-antibody heavy chain
<220> FEATURE:
<221> NAME/KEY: SIGNAL
<222> LOCATION: (1)..(19)

<400> SEQUENCE: 67
```

Met Ala Val Leu Ala Leu Leu Leu Cys Leu Val Thr Phe Pro Ser Cys
1               5                   10                  15

Val Leu Ser Gln Val Gln Leu Lys Glu Ser Gly Pro Asp Leu Val Ala
            20                  25                  30

Pro Ser Gln Ser Leu Ser Ile Thr Cys Thr Val Ser Gly Phe Ser Leu
        35                  40                  45

Ser Lys Phe Gly Val Asn Trp Val Arg Gln Pro Pro Gly Lys Gly Leu
    50                  55                  60

Glu Trp Leu Gly Val Ile Trp Gly Asp Gly Ser Thr Ser Tyr Asn Ser
65                  70                  75                  80

Gly Leu Ile Ser Arg Leu Ser Ile Ser Lys Glu Asn Ser Lys Ser Gln
                85                  90                  95

Val Phe Leu Lys Leu Asn Ser Leu Gln Ala Asp Asp Thr Ala Thr Tyr
            100                 105                 110

Tyr Cys Val Lys Pro Gly Gly Asp Tyr Trp Gly His Gly Thr Ser Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Pro Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val

```
                    305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Met Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
                450                 455                 460

<210> SEQ ID NO 68
<211> LENGTH: 10
<212> TYPE: PRT
<213> ORGANISM: Artificial Sequence
<220> FEATURE:
<223> OTHER INFORMATION: NPC-1 chi-antibody heavy chain CDR1

<400> SEQUENCE: 68

Gly Phe Ser Leu Ser Lys Phe Gly Val Asn
1               5                   10

<210> SEQ ID NO 69
<211> LENGTH: 16
<212> TYPE: PRT
<213> ORGANISM: Artificial Sequence
<220> FEATURE:
<223> OTHER INFORMATION: NPC-1 chi-antibody heavy chain CDR2

<400> SEQUENCE: 69

Val Ile Trp Gly Asp Gly Ser Thr Ser Tyr Asn Ser Gly Leu Ile Ser
1               5                   10                  15

<210> SEQ ID NO 70
<211> LENGTH: 5
<212> TYPE: PRT
<213> ORGANISM: Artificial Sequence
<220> FEATURE:
<223> OTHER INFORMATION: NPC-1 chi-antibody heavy chain CDR3

<400> SEQUENCE: 70

Pro Gly Gly Asp Tyr
1               5

<210> SEQ ID NO 71
<211> LENGTH: 735
<212> TYPE: DNA
<213> ORGANISM: Artificial Sequence
<220> FEATURE:
<223> OTHER INFORMATION: Humanized NEO 103 light chain

<400> SEQUENCE: 71
aagcttgcca ccatgaagta cctgctgccc accgctgctg ctggcttgct gctgctggca      60
```

```
gctcagcctg ccatggccga gatcgtgctg acccagtctc ctggcaccct gtctctgagc    120
cctggcgaga gagctaccct gtcctgctcc gcctcctcca gcatctccta catgtactgg    180
tatcagcaga agcccggcca ggcccctcgg ctgctgatct acgatacctc caagctggcc    240
tccggcatcc ccgacagatt ctccggctct ggctctggca ccgacttcac cctgaccatc    300
tcccggctgg aacccgagga cttcgccgtg tactactgcc accagcggga ctcctacccc    360
tggacctttg gccagggcac caagctggaa atcaagcgga ccgtggccgc tcccctccgtg   420 ttcatcttcc caccttccga cgagcagctg aagtccggca ccgcttctgt cgtgtgcctg    480
ctgaacaact ctaccccccg cgaggccaag gtgcagtgga aggtggacaa cgccctgcag    540
tccggcaact cccaggaatc cgtgaccgag caggactcca aggacagcac ctactccctg    600
tcctctaccc tgaccctgtc caaggccgac tacgagaagc acaaggtgta cgcctgcgaa    660
gtgacccacc agggcctgtc tagccccgtg accaagtctt tcaaccgggg cgagtgctga    720
tgaggatcct gatga                                                     735
```

<210> SEQ ID NO 72
<211> LENGTH: 239
<212> TYPE: PRT
<213> ORGANISM: Artificial Sequence
<220> FEATURE:
<223> OTHER INFORMATION: Humanized NEO 103 light chain

<400> SEQUENCE: 72

```
Lys Leu Ala Thr Met Lys Tyr Leu Leu Pro Thr Ala Ala Ala Gly Leu
1               5                   10                  15

Leu Leu Leu Ala Ala Gln Pro Ala Met Ala Glu Ile Val Leu Thr Gln
                20                  25                  30

Ser Pro Gly Thr Leu Ser Leu Ser Pro Gly Glu Arg Ala Thr Leu Ser
            35                  40                  45

Cys Ser Ala Ser Ser Ser Ile Ser Tyr Met Tyr Trp Tyr Gln Gln Lys
    50                  55                  60

Pro Gly Gln Ala Pro Arg Leu Leu Ile Tyr Asp Thr Ser Lys Leu Ala
65                  70                  75                  80

Ser Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys His Gln Arg Asp Ser Tyr Pro Trp Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 73
<211> LENGTH: 1437
<212> TYPE: DNA
<213> ORGANISM: Artificial Sequence
<220> FEATURE:
<223> OTHER INFORMATION: Humanized NEO 103 heavy chain

<400> SEQUENCE: 73
aagcttgcca ccatggacct gctgtgcaag aacatgaagc acctgtggtt ctttctgctg      60
ctggtggccg ctcccagatg ggtgctgtct caggtgcagc tggtggaatc tggccctggc     120
ctggtgcagc cttccagatc cctgtctctg acctgctcct ccagcggctt cagcctgtcc     180
aagttcggcg tgaactgggt gcgacagcct ctggcaaggg cctggaatg ggtgggagtg      240 atctggggcg acggctccac ctcctacaac tccggcctga tctccagagt gaccatctcc     300
cgggacaccc tccaagaacca gctgttcctg aagatggact ccctgaccgc cgaggacacc    360
gccgtgtact actgtgctag acctggcggc gactactggg gccagggcac aacagtgacc     420
gtgtcctccg cttccaccaa gggccccctct gtgtttcctc tggcccctcc cagcaagtcc    480
acctctggtg gaactgccgc tctgggctgc ctcgtgaagg actacttccc cgagcccgtg    540
acagtgtcct ggaactctgg cgctctgacc tccggcgtgc acacctttcc agctgtgctg    600
cagtccagcg gcctgtactc cctgtcctcc gtcgtgaccg tgccttccag ctctctgggc    660
acccagacct acatctgcaa cgtgaaccac aagccctcca ataccaaggt ggacaagaag    720
gtggaaccca gtcctgcga caagacccac acctgtcccc cttgtcctgc ccctgaactg     780
ctgggcggac cttccgtgtt cctgttcccc ccaaagccca aggacaccct gatgatctcc    840
cggacccccg aagtgacctg cgtggtggtg gatgtgtccc acgaggaccc tgaagtgaag   900
ttcaattggt acgtggacgg cgtggaagtg cacaacgcca agaccaagcc tagagaggaa   960
cagtacaact ccacctaccg ggtggtgtcc gtgctgaccg tgctgcatca ggactggctg   1020
aacggcaaag agtacaagtg caaggtgtcc aacaaggccc tgcctgcccc catcgaaaag   1080
accatcagca aggctaaggg ccagccccgc gagccccagg tgtacacact gcctccatcc   1140
cgggaagaga tgaccaagaa tcaggtgtcc ctgacctgtc tcgtgaaagg cttctacccc   1200
tccgatatcg ccgtggaatg ggagtccaac ggccagcccg agaacaacta caagaccacc   1260
ccccctgtgc tggactccga cggctcattc ttcctgtaca gcaagctgac agtggacaag   1320
tcccggtggc agcagggcaa cgtgttctcc tgctccgtga tgcacgaggc cctgcacaac   1380
cactacaccc agaagtccct gtccctgagc cccggcaagt gatgatgagg atcctga     1437

<210> SEQ ID NO 74
<211> LENGTH: 473
<212> TYPE: PRT
<213> ORGANISM: Artificial Sequence
<220> FEATURE:
<223> OTHER INFORMATION: Humanized NEO 103 heavy chain

<400> SEQUENCE: 74

Lys Leu Ala Thr Met Asp Leu Leu Cys Lys Asn Met Lys His Leu Trp
1               5                   10                  15

Phe Phe Leu Leu Leu Val Ala Ala Pro Arg Trp Val Leu Ser Gln Val
            20                  25                  30

Gln Leu Val Glu Ser Gly Pro Gly Leu Val Gln Pro Ser Arg Ser Leu
        35                  40                  45

Ser Leu Thr Cys Ser Ser Ser Gly Phe Ser Leu Ser Lys Phe Gly Val
```

```
                50                  55                  60
Asn Trp Val Arg Gln Pro Pro Gly Lys Gly Leu Glu Trp Val Gly Val
 65                  70                  75                  80

Ile Trp Gly Asp Gly Ser Thr Ser Tyr Asn Ser Gly Leu Ile Ser Arg
                     85                  90                  95

Val Thr Ile Ser Arg Asp Thr Ser Lys Asn Gln Leu Phe Leu Lys Met
                    100                 105                 110

Asp Ser Leu Thr Ala Glu Asp Thr Ala Val Tyr Tyr Cys Ala Arg Pro
                    115                 120                 125

Gly Gly Asp Tyr Trp Gly Gln Gly Thr Thr Val Thr Val Ser Ser Ala
                    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                    165                 170                 175

Pro Glu Pro Val Thr Val Ser Trp Asn Ser Gly Ala Leu Thr Ser Gly
                    180                 185                 190

Val His Thr Phe Pro Ala Val Leu Gln Ser Ser Gly Leu Tyr Ser Leu
                    195                 200                 205

Ser Ser Val Val Thr Val Pro Ser Ser Ser Leu Gly Thr Gln Thr Tyr
                    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                    245                 250                 255

Ala Pro Glu Leu Leu Gly Gly Pro Ser Val Phe Leu Phe Pro Pro Lys
                    260                 265                 270

Pro Lys Asp Thr Leu Met Ile Ser Arg Thr Pro Glu Val Thr Cys Val
                    275                 280                 285

Val Val Asp Val Ser His Glu Asp Pro Glu Val Lys Phe Asn Trp Tyr
                    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                    325                 330                 335

Gln Asp Trp Leu Asn Gly Lys Glu Tyr Lys Cys Lys Val Ser Asn Lys
                    340                 345                 350

Ala Leu Pro Ala Pro Ile Glu Lys Thr Ile Ser Lys Ala Lys Gly Gln
                    355                 360                 365

Pro Arg Glu Pro Gln Val Tyr Thr Leu Pro Pro Ser Arg Glu Glu Met
                    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                    405                 410                 415

Tyr Lys Thr Thr Pro Pro Val Leu Asp Ser Asp Gly Ser Phe Phe Leu
                    420                 425                 430

Tyr Ser Lys Leu Thr Val Asp Lys Ser Arg Trp Gln Gln Gly Asn Val
                    435                 440                 445

Phe Ser Cys Ser Val Met His Glu Ala Leu His Asn His Tyr Thr Gln
                    450                 455                 460

Lys Ser Leu Ser Leu Ser Pro Gly Lys
465                 470
```

<210> SEQ ID NO 75
<211> LENGTH: 963
<212> TYPE: DNA
<213> ORGANISM: Artificial Sequence
<220> FEATURE:
<223> OTHER INFORMATION: 16C3 antibody light chain

<400> SEQUENCE: 75

```
gcggggcagc ctcacacaga acacacacag atatgggtgt acccactcag ctcctgttgc    60
tgtggcttac agtcgtagtt gtcagatgtg acatccagat gactcagtct ccagcttcac   120
tgtctgcatc tgtgggagaa actgtcacca tcacatgtgg agcaagtgag aatatttacg   180
gtgctttaaa ttggtatcag cggaaacagg gaaaatctcc tcagctcctg atttatggcg   240
caagtaattt ggcagatggc atgtcatcga ggttcagtgg cagtggatct ggtagacagt   300
attctctcaa gatcagtagc ctgcatcctg acgatgttgc aacgtattac tgtcaaaatg   360
tattaagtag tccgtacacg ttcggagggg ggaccaagct ggaaataaaa cgggctgatg   420
ctgcaccaac tgtatccatc ttcccaccat ccagtgagca gttaacatct ggaggtgcct   480
cagtcgtgtg cttcttgaac aacttctacc ccaaagacat caatgtcaag tggaagattg   540
atggcagtga acgacaaaat ggcgtcctga cagttggac tgatcaggac agcaaagaca   600
gcacctacag catgagcagc accctcacgt tgaccaagga cgagtatgaa cgacataaca   660
gctatacctg tgaggccact cacaagacac aacttcacc cattgtcaag agcttcaaca   720
ggaatgagtg ttagagacaa aggtcctgag acgccaccac cagctcccca gctccatcct   780
atcttccctt ctaaggtctt ggaggcttcc ccacaagcga ctaccactgt tgcggtgctc   840
caaacctcct ccccacctcc ttctcctcct cctcccttc cttggctttt atcatgctaa   900
tatttgcaga aatattcaa taaagtgatc tttgcacaaa aaaaaaaaa aaaaaaaaaa   960
aaa                                                               963
```

<210> SEQ ID NO 76
<211> LENGTH: 107
<212> TYPE: PRT
<213> ORGANISM: Artificial Sequence
<220> FEATURE:
<223> OTHER INFORMATION: 16C3 antibody light chain
<220> FEATURE:
<221> NAME/KEY: MISC_FEATURE
<222> LOCATION: (22)..(32)
<223> OTHER INFORMATION: CDR1
<220> FEATURE:
<221> NAME/KEY: MISC_FEATURE
<222> LOCATION: (48)..(54)
<223> OTHER INFORMATION: CDR2
<220> FEATURE:
<221> NAME/KEY: MISC_FEATURE
<222> LOCATION: (86)..(95)
<223> OTHER INFORMATION: CDR3

<400> SEQUENCE: 76

```
Leu Met Thr Gln Ser Pro Ala Ser Leu Ser Ala Ser Val Gly Glu Thr
  1               5                  10                  15

Val Thr Ile Thr Cys Gly Ala Ser Glu Asn Ile Tyr Gly Ala Leu Asn
             20                  25                  30

Trp Tyr Gln Arg Lys Gln Gly Lys Ser Pro Gln Leu Leu Ile Tyr Gly
         35                  40                  45

Ala Ser Asn Leu Ala Asp Gly Met Ser Ser Arg Phe Ser Gly Ser Gly
     50                  55                  60
```

```
Ser Gly Arg Gln Tyr Ser Leu Lys Ile Ser Ser Leu His Pro Asp Asp
 65                  70                  75                  80

Val Ala Thr Tyr Tyr Cys Gln Asn Val Leu Ser Ser Pro Tyr Thr Phe
                 85                  90                  95

Gly Gly Gly Thr Lys Leu Glu Ile Lys Lys Gly
            100                 105
```

<210> SEQ ID NO 77
<211> LENGTH: 11
<212> TYPE: PRT
<213> ORGANISM: Artificial Sequence
<220> FEATURE:
<223> OTHER INFORMATION: 16C3 light chain CDR1

<400> SEQUENCE: 77

```
Gly Ala Ser Glu Asn Ile Tyr Gly Ala Leu Asn
1               5                   10
```

<210> SEQ ID NO 78
<211> LENGTH: 7
<212> TYPE: PRT
<213> ORGANISM: Artificial Sequence
<220> FEATURE:
<223> OTHER INFORMATION: 16C3 antibody light chain CDR2

<400> SEQUENCE: 78

```
Gly Ala Ser Asn Leu Ala Asp
1               5
```

<210> SEQ ID NO 79
<211> LENGTH: 10
<212> TYPE: PRT
<213> ORGANISM: Artificial Sequence
<220> FEATURE:
<223> OTHER INFORMATION: 16C3 antibody light chain CDR3

<400> SEQUENCE: 79

```
Cys Gln Asn Val Leu Ser Ser Pro Tyr Thr
1               5                   10
```

<210> SEQ ID NO 80
<211> LENGTH: 1575
<212> TYPE: DNA
<213> ORGANISM: Artificial Sequence
<220> FEATURE:
<223> OTHER INFORMATION: 16C3 antibody heavy chain

<400> SEQUENCE: 80

| | | | | | |
|---|---|---|---|---|---|
| acgcgggaca | cagtagtctc | tacagtcaca | ggagtacaca | ggacattgcc | atgggttgga | 60 |
| gctgtatcat | cttctttctg | gtagcaacag | ctacaggtgt | gcactcccag | gtccagctgc | 120 |
| agcagtctgg | gcctgaggtg | gtgaggcctg | ggtctcagt | gaagatttcc | tgcaagggtt | 180 |
| ccggctacac | attcactgat | tatgctatgc | actgggtgaa | gcagagtcat | gcaaagagtc | 240 |
| tcgagtggat | tggacttatt | agtacttaca | gtggtgatac | aaagtacaac | cagaatttaa | 300 |
| gggcaaggcc | acaatgactg | tagacaaatc | ctccaacaca | gcctatatgg | aacttgccag | 360 |
| attgacatct | gaggattctg | ccatctatta | ctgtgcaaga | ggggattatt | ccggtagtag | 420 |
| gtactggttt | gcttactggg | gccaagggac | tctggtcact | gtctctgcag | ccaaaacgac | 480 |
| acccccatct | gtctatccac | tggcccctgg | atctgctgcc | caaactaact | ccatggtgac | 540 |
| cctgggatgc | ctggtcaagg | gctatttccc | tgagccagtg | acagtgacct | ggaactctgg | 600 |
| atccctgtcc | agcggtgtgc | acaccttccc | agctgttcct | gcagtctgac | ctctacactc | 660 |

```
tgagcagctc agtgactgtc cctccagca cctggcccag cgagaccgtc acctgcaacg    720
ttgcccaccc ggccagcagc accaaggtgg acaagaaaat tgtgcccagg gattgtggtt    780
gtaagccttg catatgtaca gtcccagaag tatcatctgt cttcatcttc cccccaaagc    840
ccaaggatgt gctcaccatt actctgactc taaggtcac gtgtgttgtg gtagacatca     900
gcaaggatga tcccgaggtc cagttcagct ggtttgtaga tgatgtggag gtgcacacag    960
ctcagacgca accccgggag gagcagttca acagcacttt ccgctcagtc agtgaacttc   1020
ccatcatgca ccaggactgg ctcaatggca aggagttcaa atgcagggtc aacagtgcag   1080
ctttccctgc ccccatcgag aaaaccatct ccaaaaccaa aggcagaccg aaggctccac   1140
aggtgtacac cattccacct cccaaggagc agatggccaa ggataaagtc agtctgacct   1200
gcatgataac agacttcttc cctgaagaca ttactgtgga gtggcagtgg aatgggcagc   1260
cagcggagaa ctacaagaac actcagccca tcatggacac agatggctct tacttcgtct   1320
acagcaagct caatgtgcag aagagcaact gggaggcagg aaatactttc acctgctctg   1380
tgttacatga gggcctgcac aaccaccata ctgagaagag cctctcccac tctcctggta   1440
aatgatccca gtgtccttgg agccctctgg ccctacagga ctttgacacc tacctccacc   1500
cctccctgta taaataaagc acccagcact gcctcgggac cctgcataaa aaaaaaaaa   1560 aaaaaaaaaa aaaaa                                                   1575
```

<210> SEQ ID NO 81
<211> LENGTH: 116
<212> TYPE: PRT
<213> ORGANISM: Artificial Sequence
<220> FEATURE:
<223> OTHER INFORMATION: 16C3 antibody heavy chain
<220> FEATURE:
<221> NAME/KEY: MISC_FEATURE
<222> LOCATION: (23)..(32)
<223> OTHER INFORMATION: CDR1
<220> FEATURE:
<221> NAME/KEY: MISC_FEATURE
<222> LOCATION: (47)..(63)
<223> OTHER INFORMATION: CDR2
<220> FEATURE:
<221> NAME/KEY: MISC_FEATURE
<222> LOCATION: (96)..(107)
<223> OTHER INFORMATION: CDR3

<400> SEQUENCE: 81

```
Leu Glu Glu Ser Gly Pro Glu Val Val Arg Pro Gly Val Ser Val Lys
1               5                   10                  15

Ile Ser Cys Lys Gly Ser Gly Tyr Thr Phe Thr Asp Tyr Ala Met His
            20                  25                  30

Trp Val Lys Gln Ser His Ala Lys Ser Leu Glu Trp Ile Gly Leu Ile
        35                  40                  45

Ser Thr Tyr Ser Gly Asp Thr Lys Tyr Asn Gln Asn Phe Lys Gly Lys
    50                  55                  60

Ala Thr Met Thr Val Asp Lys Ser Ser Asn Thr Ala Tyr Met Glu Leu
65                  70                  75                  80

Ala Arg Leu Thr Ser Glu Asp Ser Ala Ile Tyr Tyr Cys Ala Arg Gly
                85                  90                  95

Asp Tyr Ser Gly Ser Arg Tyr Trp Phe Ala Tyr Trp Gly Gln Gly Thr
            100                 105                 110

Thr Val Thr Arg
        115
```

<210> SEQ ID NO 82
<211> LENGTH: 10
<212> TYPE: PRT
<213> ORGANISM: Artificial Sequence
<220> FEATURE:
<223> OTHER INFORMATION: 16C3 antibody heavy chain CDR1

<400> SEQUENCE: 82

Gly Tyr Thr Phe Thr Asp Tyr Ala Met His
1               5                   10

<210> SEQ ID NO 83
<211> LENGTH: 17
<212> TYPE: PRT
<213> ORGANISM: Artificial Sequence
<220> FEATURE:
<223> OTHER INFORMATION: 16C3 antibody heavy chain CDR2

<400> SEQUENCE: 83

Leu Ile Ser Thr Tyr Ser Gly Asp Thr Lys Tyr Asn Gln Asn Phe Lys
1               5                   10                  15

Gly

<210> SEQ ID NO 84
<211> LENGTH: 12
<212> TYPE: PRT
<213> ORGANISM: Artificial Sequence
<220> FEATURE:
<223> OTHER INFORMATION: 16C3 antibody heavy chain CDR3

<400> SEQUENCE: 84

Gly Asp Tyr Ser Gly Ser Arg Tyr Trp Phe Ala Tyr
1               5                   10

<210> SEQ ID NO 85
<211> LENGTH: 107
<212> TYPE: PRT
<213> ORGANISM: Artificial Sequence
<220> FEATURE:
<223> OTHER INFORMATION: 16C3 antibody light chain (ven16C3)

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: 16C3 antibody light chain (cdr16C3)

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 87
<211> LENGTH: 107
<212> TYPE: PRT
<213> ORGANISM: Artificial Sequence
<220> FEATURE:
<223> OTHER INFORMATION: 16C3 antibody light chain (abb16C3)

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: 16C3 antibody light chain (sdr16C3)

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Arg Gln Tyr Thr Phe Thr Ile Ser Ser Leu Gln Pro
65                  70                  75                  80

```
Glu Asp Ile Ala Thr Tyr Tyr Cys Gln Gln Val Leu Ser Ser Pro Tyr
                85                  90                  95

Thr Phe Gly Gly Gly Thr Lys Leu Glu Ile Lys
            100                 105
```

<210> SEQ ID NO 89
<211> LENGTH: 107
<212> TYPE: PRT
<213> ORGANISM: Artificial Sequence
<220> FEATURE:
<223> OTHER INFORMATION: 16C3 antibody light chain (fra16C3)

<400> SEQUENCE: 89

```
Asp Ile Gln Met Thr Gln Ser Pro Ser Ser Leu Ser Ala Ser Val Gly
1               5                   10                  15

Asp Arg Val Thr Ile Thr Cys Cys Ala Ser Glu Asn Ile Tyr Gly Ala
            20                  25                  30

Leu Asn Trp Tyr Gln Arg Lys Pro Gly Lys Ser Pro Asn Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105
```

<210> SEQ ID NO 90
<211> LENGTH: 121
<212> TYPE: PRT
<213> ORGANISM: Artificial Sequence
<220> FEATURE:
<223> OTHER INFORMATION: 16C3 antibody heavy chain (ven16C3)

<400> SEQUENCE: 90

```
Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120
```

<210> SEQ ID NO 91
<211> LENGTH: 121
<212> TYPE: PRT
<213> ORGANISM: Artificial Sequence
<220> FEATURE:
<223> OTHER INFORMATION: 16C3 antibody heavy chain (cdr16C3)

<400> SEQUENCE: 91

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Thr Ser Ile Ser Thr Ala Tyr
65                  70                  75                  80

Met Glu Leu Ser Arg Leu Arg Ser Asp Asp Thr Ala Ile Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 92
<211> LENGTH: 121
<212> TYPE: PRT
<213> ORGANISM: Artificial Sequence
<220> FEATURE:
<223> OTHER INFORMATION: 16C3 antibody heavy chain (abb16C3)

<400> SEQUENCE: 92

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Ser Gln Lys Phe
    50                  55                  60

Gln Gly Arg Val Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 93
<211> LENGTH: 121
<212> TYPE: PRT
<213> ORGANISM: Artificial Sequence
<220> FEATURE:
<223> OTHER INFORMATION: 16C3 antibody heavy chain (sdr16C3)

<400> SEQUENCE: 93

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

```
Gly Leu Ile Ser Thr Tyr Ser Gly Asp Thr Lys Tyr Asn Gln Lys Phe
        50                  55                  60

Gln Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
                100                 105                 110

Gln Gly Thr Leu Val Thr Val Ser Ser
        115                 120

<210> SEQ ID NO 94
<211> LENGTH: 121
<212> TYPE: PRT
<213> ORGANISM: Artificial Sequence
<220> FEATURE:
<223> OTHER INFORMATION: 16C3 antibody heavy chain (fra16C3)

<400> SEQUENCE: 94

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
                20                  25                  30

Ala Met His Trp Val Lys Gln Ser His Ala Lys Ser Leu Glu Trp Ile
            35                  40                  45

Gly Leu Ile Ser Thr Tyr Ser Gly Asp Thr Lys Tyr Asn Gln Asn Phe
        50                  55                  60

Lys Gly Lys Ala Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
                100                 105                 110

Gln Gly Thr Leu Val Thr Val Ser Ser
        115                 120

<210> SEQ ID NO 95
<211> LENGTH: 702
<212> TYPE: DNA
<213> ORGANISM: Artificial Sequence
<220> FEATURE:
<223> OTHER INFORMATION: h16C3-Abb* light chain

<400> SEQUENCE: 95
atgggcgtgc ccacccagct gctgctgctg tggctgaccg tggtggtggt gcggtgcgac    60
atccagatga cccagtcccc tagctctctg agcgcctccg tgggcgacag ggtgaccatc   120
acctgccaag cctctgagaa catctacggc gccctgaact ggtaccagag gaagcccggc   180
aagagcccca agctgctgat ctacggcgcc tctaacctgg ccaccggcat gcctagccgg   240
ttctccggct ccggcagcgg caccgactac accttcacca tctcctccct gcaacccgag   300
gacatcgcca cctactactg ccagcaggtg ctgtcctccc cctacacctt cggcggcggc   360
accaaactgg agatcaagcg gaccgtggcc gcccccagcg tgttcatctt cccccccctct   420 gacgagcagc tgaagtccgg caccgcctct gtggtgtgcc tgctgaacaa cttctacccc   480
agggaggcca aggtccagtg gaaggtggac aacgccctgc agtccggcaa cagccaggag   540
tctgtgaccg agcaggactc caaggactcc acctacagcc tgtctagcac cctgaccctg   600
```

```
tccaaggccg actacgagaa gcacaaggtg tacgcctgcg aggtgaccca ccagggcctg    660
tccagccctg tgaccaagtc cttcaacagg ggcgagtgct ga                       702
```

```
<210> SEQ ID NO 96
<211> LENGTH: 233
<212> TYPE: PRT
<213> ORGANISM: Artificial Sequence
<220> FEATURE:
<223> OTHER INFORMATION: h16C3-Abb* light chain
<220> FEATURE:
<221> NAME/KEY: MISC_FEATURE
<222> LOCATION: (43)..(53)
<223> OTHER INFORMATION: CDR1
<220> FEATURE:
<221> NAME/KEY: MISC_FEATURE
<222> LOCATION: (69)..(75)
<223> OTHER INFORMATION: CDR2
<220> FEATURE:
<221> NAME/KEY: MISC_FEATURE
<222> LOCATION: (108)..(116)
<223> OTHER INFORMATION: CDR3

<400> SEQUENCE: 96
```

```
Met Gly Val Pro Thr Gln Leu Leu Leu Trp Leu Thr Val Val
1               5                   10                  15

Val Arg Cys Asp Ile Gln Met Thr Gln Ser Pro Ser Ser Leu Ser Ala
            20                  25                  30

Ser Val Gly Asp Arg Val Thr Ile Thr Cys Gln Ala Ser Glu Asn Ile
        35                  40                  45

Tyr Gly Ala Leu Asn Trp Tyr Gln Arg Lys Pro Gly Lys Ser Pro Lys
    50                  55                  60

Leu Leu Ile Tyr Gly Ala Ser Asn Leu Ala Thr Gly Met Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln Gln Val Leu Ser
            100                 105                 110

Ser Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

```
<210> SEQ ID NO 97
<211> LENGTH: 11
<212> TYPE: PRT
<213> ORGANISM: Artificial Sequence
<220> FEATURE:
<223> OTHER INFORMATION: h16C3-Abb* light chain CDR1
```

<400> SEQUENCE: 97

Gln Ala Ser Glu Asn Ile Tyr Gly Ala Leu Asn
1               5                   10

<210> SEQ ID NO 98
<211> LENGTH: 7
<212> TYPE: PRT
<213> ORGANISM: Artificial Sequence
<220> FEATURE:
<223> OTHER INFORMATION: h16C3-Abb* light chain CDR2

<400> SEQUENCE: 98

Gly Ala Ser Asn Leu Ala Thr
1               5

<210> SEQ ID NO 99
<211> LENGTH: 9
<212> TYPE: PRT
<213> ORGANISM: Artificial Sequence
<220> FEATURE:
<223> OTHER INFORMATION: h16C3-Abb* light chain CDR3

<400> SEQUENCE: 99

Gln Gln Val Leu Ser Ser Pro Tyr Thr
1               5

<210> SEQ ID NO 100
<211> LENGTH: 1413
<212> TYPE: DNA
<213> ORGANISM: Artificial Sequence
<220> FEATURE:
<223> OTHER INFORMATION: h16C3-Abb* heavy chain

<400> SEQUENCE: 100

| | | | | | |
|---|---|---|---|---|---|
| atgggctggt | cctgcatcat | cttcttcctg | gtggccaccg | ccaccggcgt gcacagccag | 60 |
| gtgcagcttg | tgcagagcgg | cgccgaggtg | aagaagcccg | cgccagcgt gaaggtgtcc | 120 |
| tgcaaggcct | ccggctacac | cttcaccgac | tacgccatgc | actgggtgcg gcaggcccc | 180 |
| ggccagcggc | tggagtggat | gggcctgatc | agcacctact | ctggcgacac caagtacaac | 240 |
| cagaacttcc | agggccgggt | gaccatgacc | gtggacaaga | gcgccagcac cgcctacatg | 300 |
| gagctgtcct | ccctgaggtc | tgaggacacc | gccgtgtact | actgcgcccg ggcgactac | 360 |
| agcggcagcc | ggtactggtt | cgcctactgg | ggccagggca | cctggtgac cgtgtccagc | 420 |
| gcctctacca | agggcccag | cgtgtttccc | ctggccctt | cctccaaaag caccagcggc | 480 |
| ggtaccgccg | ccctgggctg | cctggtgaag | gactacttcc | ccgagcccgt gaccgtgagc | 540 |
| tggaactccg | gcgccctgac | cagcggcgtg | cacaccttcc | ctgccgtgct gcaaagctcc | 600 |
| ggcctgtact | ccctgagctc | tgtggtgacc | gtgccctcca | gctccctggg cacccagacc | 660 |
| tacatctgca | acgtgaacca | caagcccagc | aacaccaagg | tggacaagaa ggtggagcct | 720 |
| aagtcttgcg | acaagaccca | cacctgcccc | ccttgccctg | ccctgagct gctgggcggc | 780 |
| cccagcgtgt | tcctgttccc | tcccaagccc | aaggacaccc | tgatgatctc ccggacccct | 840 |
| gaggtgacct | gcgtggtggt | ggatgtgagc | cacgaggatc | ctgaagtgaa gttcaattgg | 900 |
| tatgtggatg | gcgtggaggt | gcacaacgcc | aagaccaagc | ccgggagga gcagtacaac | 960 |
| agcacctaca | gggtggtgtc | cgtgctgacc | gtgctgcacc | aggactggct gaacggcaag | 1020 |
| gagtacaagt | gcaaggtgtc | caacaaggcc | ctgcccgccc | ccatcgagaa gaccatctcc | 1080 |
| aaggccaagg | gccagccccg | ggagcccag | gtgtacaccc | tgcctccag ccgggacgag | 1140 |

```
ctgaccaaga accaggtgtc cctgacctgc ctggtgaagg gcttctaccc ctctgacatc    1200
gccgtggagt gggagagcaa cggccagccc gagaacaact acaagaccac ccccccgtg     1260 ctggactccg acggctcctt cttcctgtac tctaagctga ccgtggacaa gtcccgctgg    1320
cagcagggca acgtgttcag ctgctccgtg atgcacgagg ccctgcacaa ccactacacc    1380
cagaagagcc tgagcctgtc tcccggcaag tga                                 1413
```

<210> SEQ ID NO 101
<211> LENGTH: 470
<212> TYPE: PRT
<213> ORGANISM: Artificial Sequence
<220> FEATURE:
<223> OTHER INFORMATION: h16C3-Abb* heavy chain
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (70)..(85)
<223> OTHER INFORMATION: CDR2
<220> FEATURE:
<221> NAME/KEY: MISC_FEATURE
<222> LOCATION: (118)..(129)
<223> OTHER INFORMATION: CDR3

<400> SEQUENCE: 101

```
Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Met His Trp Val Arg Gln Ala Pro Gly Gln Arg Leu
    50                  55                  60

Glu Trp Met Gly Leu Ile Ser Thr Tyr Ser Gly Asp Thr Lys Tyr Asn
65                  70                  75                  80

Gln Asn Phe Gln Gly Arg Val Thr Met Thr Val Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Asp Tyr Ser Gly Ser Arg Tyr Trp Phe Ala
        115                 120                 125

Tyr Trp Gly Gln Gly Thr Leu Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
```

245                 250                 255
Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 102
<211> LENGTH: 10
<212> TYPE: PRT
<213> ORGANISM: Artificial Sequence
<220> FEATURE:
<223> OTHER INFORMATION: h16C3-Abb* heavy chain CDR1

<400> SEQUENCE: 102

Gly Tyr Thr Phe Thr Asp Tyr Ala Met His
1               5                   10

<210> SEQ ID NO 103
<211> LENGTH: 16
<212> TYPE: PRT
<213> ORGANISM: Artificial Sequence
<220> FEATURE:
<223> OTHER INFORMATION: h16C3-Abb* heavy chain CDR2

<400> SEQUENCE: 103

Ile Ser Thr Tyr Ser Gly Asp Thr Lys Tyr Asn Gln Asn Phe Gln Gly
1               5                   10                  15

<210> SEQ ID NO 104
<211> LENGTH: 12
<212> TYPE: PRT
<213> ORGANISM: Artificial Sequence
<220> FEATURE:
<223> OTHER INFORMATION: h16C3-Abb* heavy chain CDR3

<400> SEQUENCE: 104

Gly Asp Tyr Ser Gly Ser Arg Tyr Trp Phe Ala Tyr
1               5                   10

<210> SEQ ID NO 105
<211> LENGTH: 236
<212> TYPE: PRT
<213> ORGANISM: Artificial Sequence
<220> FEATURE:
<223> OTHER INFORMATION: humanized 31.1 antibody light chain

<400> SEQUENCE: 105

Met Lys Tyr Leu Leu Pro Thr Ala Ala Ala Gly Leu Leu Leu Leu Ala
1               5                   10                  15

Ala Gln Pro Ala Met Ala Glu Ile Val Met Thr Gln Ser Pro Leu Ser
            20                  25                  30

Leu Pro Val Ser Pro Gly Glu Pro Ala Ser Ile Ser Cys Lys Ala Ser
        35                  40                  45

Gln Ser Val Ser Asn Asp Val Ala Trp Tyr Leu Gln Lys Pro Gly Gln
    50                  55                  60

Ser Pro Lys Leu Leu Ile Tyr Tyr Ala Ser Asn Arg Tyr Thr Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Leu Gly Val Tyr Tyr Cys Gln Gln
            100                 105                 110

Asp Tyr Ser Ser Pro Leu Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 106
<211> LENGTH: 467
<212> TYPE: PRT
<213> ORGANISM: Artificial Sequence
<220> FEATURE:
<223> OTHER INFORMATION: humanized 31.1 antibody heavy chain

<400> SEQUENCE: 106

Met Asp Trp Thr Trp Arg Ile Leu Phe Leu Val Ala Ala Ala Thr Gly
1               5                   10                  15

Ala Gln Ala Gln Val Gln Leu Val Gln Ser Gly Pro Glu Leu Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Lys Gly Leu

```
            50                  55                  60
Glu Trp Met Gly Trp Ile Asn Thr Tyr Thr Gly Glu Pro Thr Tyr Ala
 65                  70                  75                  80

Asp Asp Phe Lys Gly Arg Phe Ser Met Ser Leu Asp Thr Ser Thr Ser
                 85                  90                  95

Thr Ala Tyr Leu Gln Ile Ser Ser Leu Lys Ser Glu Asp Thr Ala Val
            100                 105                 110

Tyr Phe Cys Ala Arg Ala Tyr Tyr Gly Lys Tyr Phe Asp Tyr Trp Gly
            115                 120                 125

Gln Gly Thr Leu Val Thr Val Ser Ser Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Leu Gly Thr Gln Thr Tyr Ile Cys Asn Val Asn His
                210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
                290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Asp Glu Leu Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Lys
465
```

<210> SEQ ID NO 107
<211> LENGTH: 738
<212> TYPE: DNA
<213> ORGANISM: Artificial Sequence
<220> FEATURE:
<223> OTHER INFORMATION: humanized NEO 302 light chain

<400> SEQUENCE: 107

| | | | | | |
|---|---|---|---|---|---|
| aagcttgcca | ccatgaagta | cctgctgccc | accgctgctg | ctggcttgct | gctgctggca | 60 |
| gctcagcctg | ccatggccga | gatcgtgatg | acccagtccc | ctctgtccct | gcctgtgtct | 120 |
| cctggcgagc | ctgcctccat | ctcctgcaag | gcctcccagt | ccgtgtccaa | cgacgtggcc | 180 |
| tggtatctgc | agaagcctgg | ccagtccccc | aagctgctga | tctactacgc | ctccaaccgg | 240 |
| tacaccggcg | tgcccgacag | attctccggc | tctggctctg | gcaccgactt | cacccctgaag | 300 |
| atctcccggg | tggaagccga | ggacctgggc | gtgtactact | gtcagcagga | ctactcctcc | 360 |
| cccctgacct | ttggccaggg | caccaagctg | gaaatcaagc | ggaccgtggc | cgctcccctcc | 420 |
| gtgttcatct | tcccaccttc | cgacgagcag | ctgaagtccg | gcaccgcttc | tgtcgtgtgc | 480 |
| ctgctgaaca | acttctaccc | ccgcgaggcc | aaggtgcagt | ggaaggtgga | caacgccctg | 540 |
| cagtccggca | actcccagga | atccgtgacc | gagcaggact | ccaaggacag | cacctactcc | 600 |
| ctgtccagca | ccctgaccct | gtccaaggcc | gactacgaga | gcacaaggt | gtacgcctgc | 660 |
| gaagtgaccc | accagggcct | gtctagcccc | gtgaccaagt | ctttcaaccg | gggcgagtgc | 720 |
| tgatgatgag | gatcctga | | | | | 738 |

<210> SEQ ID NO 108
<211> LENGTH: 240
<212> TYPE: PRT
<213> ORGANISM: Artificial Sequence
<220> FEATURE:
<223> OTHER INFORMATION: humanized NEO 302 light chain

<400> SEQUENCE: 108

Lys Leu Ala Thr Met Lys Tyr Leu Leu Pro Thr Ala Ala Gly Leu
1               5                   10                  15

Leu Leu Leu Ala Ala Gln Pro Ala Met Ala Glu Ile Val Met Thr Gln
            20                  25                  30

Ser Pro Leu Ser Leu Pro Val Ser Pro Gly Glu Pro Ala Ser Ile Ser
        35                  40                  45

Cys Lys Ala Ser Gln Ser Val Ser Asn Asp Val Ala Trp Tyr Leu Gln
    50                  55                  60

Lys Pro Gly Gln Ser Pro Lys Leu Leu Ile Tyr Tyr Ala Ser Asn Arg
65                  70                  75                  80

Tyr Thr Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Tyr Cys Gln Gln Asp Tyr Ser Ser Pro Leu Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 109
<211> LENGTH: 1431
<212> TYPE: DNA
<213> ORGANISM: Artificial Sequence
<220> FEATURE:
<223> OTHER INFORMATION: humanized NEO 302 heavy chain

<400> SEQUENCE: 109

| | | | |
|---|---|---|---|
| aagcttgcca ccatggactg gacctggcgc atcctgtttc tggtggccgc tgctacaggc | | | 60 |
| gcccaggctc aggtgcagct ggtgcagtct ggacccgagc tgaagaaacc tggcgcctcc | | | 120 |
| gtgaaggtgt cctgcaaggc ttccggctac acctttacca actacggcat gaactgggtg | | | 180 |
| cgacaggccc ctggcaaggg cctggaatgg atgggctgga tcaacaccta caccggcgag | | | 240 |
| cccacctacg ccgacgactt caagggccgg ttctccatgt ccctggacac ctccaccagc | | | 300 |
| accgcctacc tgcagatctc cagcctgaag tccgaggata ccgccgtgta cttctgcgcc | | | 360 |
| agagcctact acggcaagta cttcgactac tggggccagg gcaccctcgt gaccgtgtcc | | | 420 |
| tctgcttcta ccaagggccc ctccgtgttc cctctggccc cttccagcaa gtctacctct | | | 480 |
| ggcggcacag ccgctctggg ctgcctcgtg aaggactact cccccgagcc cgtgacagtg | | | 540 |
| tcttggaact ctggcgccct gacctccggc gtgcacacct ttccagctgt gctgcagtcc | | | 600 |
| tccggcctgt actccctgtc ctccgtcgtg actgtgccct ccagctctct gggcacccag | | | 660 |
| acctacatct gcaacgtgaa ccacaagccc tccaacacca aggtggacaa gaaggtggaa | | | 720 |
| cccaagtcct gcgacaagac ccacacctgt ccccccttgtc ctgccccctga actgctgggc | | | 780 |
| ggacccagcg tgttcctgtt cccccccaaag cccaaggaca ccctgatgat ctcccggacc | | | 840 |
| cccgaagtga cctgcgtggt ggtggatgtg tctcacgagg accctgaagt gaagttcaat | | | 900 |
| tggtacgtgg acggcgtgga agtgcacaac gccaagacca gcctagaga ggaacagtac | | | 960 |
| aactccacct accgggtggt gtccgtgctg accgtgctgc accaggattg gctgaacggc | | | 1020 |
| aaagagtaca gtgcaaggt gtccaacaag gccctgcctg cccccatcga aaagaccatc | | | 1080 |
| tccaaggcca agggccagcc ccgggaaccc caggtgtaca cactgccccc tagcagggac | | | 1140 |
| gagctgacca gaaccaggt gtccctgacc tgtctcgtga aaggcttcta cccctccgat | | | 1200 |
| atcgccgtgg aatgggagtc caacggccag cctgagaaca actacaagac caccccccct | | | 1260 |
| gtgctggact ccgacggctc attcttcctg tacagcaagc tgacagtgga caagtcccgg | | | 1320 |
| tggcagcagg gcaacgtgtt ctcctgctcc gtgatgcacg aggccctgca caaccactac | | | 1380 |
| acccagaagt ccctgtccct gagccccggc aagtgatgat gaggatcctg a | | | 1431 |

<210> SEQ ID NO 110
<211> LENGTH: 471
<212> TYPE: PRT
<213> ORGANISM: Artificial Sequence
<220> FEATURE:
<223> OTHER INFORMATION: humanized NEO 302 heavy chain

```
<400> SEQUENCE: 110

Lys Leu Ala Thr Met Asp Trp Thr Trp Arg Ile Leu Phe Leu Val Ala
1               5                   10                  15

Ala Ala Thr Gly Ala Gln Ala Gln Val Gln Leu Val Gln Ser Gly Pro
            20                  25                  30

Glu Leu Lys Lys Pro Gly Ala Ser Val Lys Val Ser Cys Lys Ala Ser
        35                  40                  45

Gly Tyr Thr Phe Thr Asn Tyr Gly Met Asn Trp Val Arg Gln Ala Pro
    50                  55                  60

Gly Lys Gly Leu Glu Trp Met Gly Trp Ile Asn Thr Tyr Thr Gly Glu
65                  70                  75                  80

Pro Thr Tyr Ala Asp Asp Phe Lys Gly Arg Phe Ser Met Ser Leu Asp
                85                  90                  95

Thr Ser Thr Ser Thr Ala Tyr Leu Gln Ile Ser Ser Leu Lys Ser Glu
            100                 105                 110

Asp Thr Ala Val Tyr Phe Cys Ala Arg Ala Tyr Tyr Gly Lys Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

```
Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 111
<211> LENGTH: 554
<212> TYPE: DNA
<213> ORGANISM: Artificial Sequence
<220> FEATURE:
<223> OTHER INFORMATION: 4B6 antibody light chain

<400> SEQUENCE: 111
aacctgtggg gacattgtga tgtcacagtc tccatcctcc ctggctgtgt cagcaggaga      60
aaaggtcact ttgaactgca atccagtca gagtctgctc aacagtagaa cccgaaagaa     120
ctacttggct tggtaccagc aaaaaccagg gcagtctcct aaattactga tctactgggc    180
atccactagg gaatctgggg tccctgatcg cttcacaggc agtggatctg ggacagattt    240
cactctcacc atcaacagtg tgcaggctga agacctggca gtttattact gcaagcaatc    300
ttataatctc ttcacgttcg gctcggggac aaagtmgaag taaaacgggc tgatgctgca    360
ccaactgtat ccatcttccc accatccagt gagcagttaa catctggagg tgcctcagtc    420
gtgtgcttct tgaacaactt ctaccccaaa gacaccaatg tcaagtggaa gattgatggc    480
agtgaacgac aaaatggcgt cctgaacagt tggactgatc aggacagcaa agacagcacc    540
tacagcatga gcag                                                      554

<210> SEQ ID NO 112
<211> LENGTH: 184
<212> TYPE: PRT
<213> ORGANISM: Artificial Sequence
<220> FEATURE:
<223> OTHER INFORMATION: 4B6 antibody light chain
<220> FEATURE:
<221> NAME/KEY: MISC_FEATURE
<222> LOCATION: (30)..(41)
<223> OTHER INFORMATION: 4B6 antibody light chain CDR1
<220> FEATURE:
<221> NAME/KEY: MISC_FEATURE
<222> LOCATION: (59)..(61)
<223> OTHER INFORMATION: 4B6 antibody light chain CDR2
<220> FEATURE:
<221> NAME/KEY: MISC_FEATURE
<222> LOCATION: (98)..(105)
<223> OTHER INFORMATION: 4B6 antibody light chain CDR3

<400> SEQUENCE: 112

Thr Cys Gly Asp Ile Val Met Ser Gln Ser Pro Ser Ser Leu Ala Val
1               5                   10                  15

Ser Ala Gly Glu Lys Val Thr Leu Asn Cys Lys Ser Ser Gln Ser Leu
            20                  25                  30

Leu Asn Ser Arg Thr Arg Lys Asn Tyr Leu Ala Trp Tyr Gln Gln Lys
            35                  40                  45

Pro Gly Gln Ser Pro Lys Leu Leu Ile Tyr Trp Ala Ser Thr Arg Glu
    50                  55                  60

Ser Gly Val Pro Asp Arg Phe Thr Gly Ser Gly Ser Gly Thr Asp Phe
65              70                  75                  80
```

```
Thr Leu Thr Ile Asn Ser Val Gln Ala Glu Asp Leu Ala Val Tyr Tyr
            85                  90                  95

Cys Lys Gln Ser Tyr Asn Leu Phe Thr Phe Gly Ser Gly Thr Lys Leu
        100                 105                 110

Glu Val Lys Arg Ala Asp Ala Ala Pro Thr Val Ser Ile Phe Pro Pro
        115                 120                 125

Ser Ser Glu Gln Leu Thr Ser Gly Gly Ala Ser Val Val Cys Phe Leu
        130                 135                 140

Asn Asn Phe Tyr Pro Lys Asp Thr Asn Val Lys Trp Lys Ile Asp Gly
145                 150                 155                 160

Ser Glu Arg Gln Asn Gly Val Leu Asn Ser Trp Thr Asp Gln Asp Ser
                165                 170                 175

Lys Asp Ser Thr Tyr Ser Met Ser
            180
```

<210> SEQ ID NO 113
<211> LENGTH: 12
<212> TYPE: PRT
<213> ORGANISM: Artificial Sequence
<220> FEATURE:
<223> OTHER INFORMATION: 4B6 antibody light chain CDR1

<400> SEQUENCE: 113

```
Gln Ser Leu Leu Asn Ser Arg Thr Arg Lys Asn Tyr
1               5                   10
```

<210> SEQ ID NO 114
<211> LENGTH: 3
<212> TYPE: PRT
<213> ORGANISM: Artificial Sequence
<220> FEATURE:
<223> OTHER INFORMATION: 4B6 antibody light chain CDR2

<400> SEQUENCE: 114

```
Trp Ala Ser
1
```

<210> SEQ ID NO 115
<211> LENGTH: 8
<212> TYPE: PRT
<213> ORGANISM: Artificial Sequence
<220> FEATURE:
<223> OTHER INFORMATION: 4B6 light chain CDR3

<400> SEQUENCE: 115

```
Lys Gln Ser Tyr Asn Leu Phe Thr
1               5
```

<210> SEQ ID NO 116
<211> LENGTH: 351
<212> TYPE: DNA
<213> ORGANISM: Artificial Sequence
<220> FEATURE:
<223> OTHER INFORMATION: 4B6 heavy chain

<400> SEQUENCE: 116

```
tgaggtgcag ctggaggagt ctggagctga actggcgagg cccggggctt cagtgaagct    60
gtcttgtaag gcttctggct actccttcac tgactattat ataaattggg tgaagcagag   120
gactggacag ggccttgagt ggattggaga aatttatcct ttaggtggta ctagtttcta   180
caatgagagg ttcaaggaca aggccacact gactgcagac aaatcctcca gcacagtcta   240
```

```
catggaactc agcagcctga catctgagga ctcggcagtc tatttctgtg caagagggga    300
taattattac gacgtctact ttgactactg gggccaaggg accacggtca c              351
```

<210> SEQ ID NO 117
<211> LENGTH: 111
<212> TYPE: PRT
<213> ORGANISM: Artificial Sequence
<220> FEATURE:
<223> OTHER INFORMATION: 4B6 antibody heavy chain
<220> FEATURE:
<221> NAME/KEY: MISC_FEATURE
<222> LOCATION: (26)..(33)
<223> OTHER INFORMATION: CDR1
<220> FEATURE:
<221> NAME/KEY: MISC_FEATURE
<222> LOCATION: (51)..(58)
<223> OTHER INFORMATION: CDR2
<220> FEATURE:
<221> NAME/KEY: MISC_FEATURE
<222> LOCATION: (97)..(109)
<223> OTHER INFORMATION: CDR3

<400> SEQUENCE: 117

Glu Val Gln Leu Glu Glu Ser Gly Ala Glu Leu Ala Arg Pro Gly Ala
1               5                   10                  15

Ser Val Lys Leu Ser Cys Lys Ala Ser Gly Tyr Ser Phe Thr Asp Tyr
                20                  25                  30

Tyr Ile Asn Trp Val Lys Gln Arg Thr Gly Gln Gly Leu Glu Trp Ile
            35                  40                  45

Gly Glu Ile Tyr Pro Leu Gly Gly Thr Ser Phe Tyr Asn Glu Arg Phe
        50                  55                  60

Lys Asp Lys Ala Thr Leu Thr Ala Asp Lys Ser Ser Ser Thr Val Tyr
65                  70                  75                  80

Met Glu Leu Ser Ser Leu Thr Ser Glu Asp Ser Ala Val Tyr Phe Cys
                85                  90                  95

Ala Arg Gly Asp Asn Tyr Tyr Asp Val Tyr Phe Asp Tyr Trp Gly
            100                 105                 110

<210> SEQ ID NO 118
<211> LENGTH: 8
<212> TYPE: PRT
<213> ORGANISM: Artificial Sequence
<220> FEATURE:
<223> OTHER INFORMATION: 4B6 heavy chain CDR1

<400> SEQUENCE: 118

Gly Tyr Ser Phe Thr Asp Tyr Tyr
1               5

<210> SEQ ID NO 119
<211> LENGTH: 8
<212> TYPE: PRT
<213> ORGANISM: Artificial Sequence
<220> FEATURE:
<223> OTHER INFORMATION: 4B6 heavy chain CDR2

<400> SEQUENCE: 119

Ile Tyr Pro Leu Gly Gly Thr Ser
1               5

<210> SEQ ID NO 120
<211> LENGTH: 13
<212> TYPE: PRT
<213> ORGANISM: Artificial Sequence
<220> FEATURE:

<223> OTHER INFORMATION: 4B6 heavy chain CDR3

<400> SEQUENCE: 120

Ala Arg Gly Asp Asn Tyr Tyr Asp Val Tyr Phe Asp Tyr
1               5                   10

<210> SEQ ID NO 121
<211> LENGTH: 21
<212> TYPE: DNA
<213> ORGANISM: Artificial Sequence
<220> FEATURE:
<223> OTHER INFORMATION: siRNA ID# s9074 (sense)

<400> SEQUENCE: 121
agaugugccu caacuacgat t                                         21

<210> SEQ ID NO 122
<211> LENGTH: 21
<212> TYPE: DNA
<213> ORGANISM: Artificial Sequence
<220> FEATURE:
<223> OTHER INFORMATION: siRNA ID# s9074 (antisense)

<400> SEQUENCE: 122
ucguaguuga ggcacaucut g                                         21

<210> SEQ ID NO 123
<211> LENGTH: 21
<212> TYPE: DNA
<213> ORGANISM: Artificial Sequence
<220> FEATURE:
<223> OTHER INFORMATION: siRNA ID# s9075 (sense)

<400> SEQUENCE: 123
gcucuggaac gugagcauat t                                         21

<210> SEQ ID NO 124
<211> LENGTH: 21
<212> TYPE: RNA
<213> ORGANISM: Artificial Sequence
<220> FEATURE:
<223> OTHER INFORMATION: siRNA ID# s9075 (antisense)

<400> SEQUENCE: 124
uaugcucacg uuccagagcc g                                         21

<210> SEQ ID NO 125
<211> LENGTH: 21
<212> TYPE: DNA
<213> ORGANISM: Artificial Sequence
<220> FEATURE:
<223> OTHER INFORMATION: siRNA ID# s9076

<400> SEQUENCE: 125
gcgugcucgu cgacaacuat t                                         21

<210> SEQ ID NO 126
<211> LENGTH: 21
<212> TYPE: RNA
<213> ORGANISM: Artificial Sequence
<220> FEATURE:
<223> OTHER INFORMATION: siRNA ID# s9076 (antisense)

<400> SEQUENCE: 126
uaguugucga cgagcacgcg g                                         21

```
<210> SEQ ID NO 127
<211> LENGTH: 21
<212> TYPE: DNA
<213> ORGANISM: Artificial Sequence
<220> FEATURE:
<223> OTHER INFORMATION: siRNA ID# S2885 (sense)

<400> SEQUENCE: 127
agaacucagu gagugcaaat t                                                 21

<210> SEQ ID NO 128
<211> LENGTH: 21
<212> TYPE: RNA
<213> ORGANISM: Artificial Sequence
<220> FEATURE:
<223> OTHER INFORMATION: siRNA ID#S2885 (antisense)

<400> SEQUENCE: 128
uuugcacuca cugaguucug g                                                 21

<210> SEQ ID NO 129
<211> LENGTH: 21
<212> TYPE: DNA
<213> ORGANISM: Artificial Sequence
<220> FEATURE:
<223> OTHER INFORMATION: siRNA ID#S9285

<400> SEQUENCE: 129
ggaacgaugc aggauccuat t                                                 21

<210> SEQ ID NO 130
<211> LENGTH: 21
<212> TYPE: DNA
<213> ORGANISM: Artificial Sequence
<220> FEATURE:
<223> OTHER INFORMATION: siRNA ID#S9285 (antisense)

<400> SEQUENCE: 130
uaggauccug caucguucct t                                                 21
```

ANTI-CANCER ANTIBODIES, COMBINATION THERAPIES, AND USES THEREOF

RELATED APPLICATION DISCLOSURE

This application claims the benefit of U.S. Provisional Patent Application Ser. No. 62/142,770, filed Apr. 3, 2016, which is hereby incorporated by reference in its entirety.

SEQUENCE DISCLOSURE

This application includes as part of its disclosure a biological sequence listing contained in the file "43282o4202.txt" and having a size of 212,792 bytes, created on Apr. 4, 2016, which is hereby incorporated by reference in its entirety.

FIELD

The present application generally relates to the field of cancer diagnostics and therapeutics. Exemplary embodiments provide methods wherein cancer is detected, diagnosed, monitored, and/or treated. Exemplary treatment methods involve combination therapies, which may include an antibody as disclosed herein and another anti-cancer agent. Said other anti-cancer agent may target the extrinsic apoptosis pathway, intrinsic apoptosis pathway, or the common apoptosis pathway.

BACKGROUND

Cancer is caused by a malfunction in the growth control systems of a cell. Cells control their growth via combination of proliferation inhibition by tumor suppressor genes (e.g., Retinoblastoma protein (pRb), p53) and proliferation activation by oncogenes (proto-oncogenes) (e.g., RAS, WNT, MYC, EKR, and TRK). A mutation in either a tumor suppressor gene and/or a protooncogene in a cell results in unusually high rates of cell proliferation (e.g., a tumor cell). See Knudson (1971) Proc. Natl. Acad. Sci. USA 68(4): 820-823. The cell may exhibit early signs of aberrant growth such as aberrant morphology or unusually large size (hyperplasia). The tumor cells also may proliferate at a higher than usual but not lethal rate, forming a growth, known as benign tumor (dysplasia). In later stages of cancer, the tumor cells proliferate at an unusually high rate resulting in uncontrolled growth that threatens the health of the patient known as malignant tumors (or in situ cancer). Many tumors can "metastasize" or spread throughout the body forming tumors. Metastasis is generally a sign of late stage, terminal cancer. Weinberg (September 1996) "How Cancer Arises" Scientific American 62-70.

Many cancer therapies exert their antitumor effect by triggering apoptosis in cancer cells. Stress-inducible molecules, for example, c-Jun N-terminal kinase (JNK), mitogen-activated protein kinase (MAPK)/extracellular signal-regulated protein kinase (ERK), nuclear factor kappa B (NF-κB) or ceramide, have been implied in transmitting apoptotic signals. Proteolytic enzymes including caspases are important effector molecules in apoptosis. The caspases are a family of cysteine proteases that act as death effector molecules in various forms of cell death.

Co-owned prior applications have described multiple cancer-associated antigens and specific antibodies thereto, e.g., in the following U.S. and PCT applications and U.S. patents: WO/2012/040617, WO/2011/163401, WO/2009/062050, WO/2006/113546, U.S. Pat. Nos. 7,829,678, 7,763,720, and 7,314,622, and U.S. pre-grant publication nos. 2012/0034227, 2011/0165599, 2011/0158902, 2011/0129416, 2011/0076761, 2010/0310559, 2009/0162931, and 2008/0227965, each of which is hereby incorporated by reference in its entirety. These include cancer-specific antigens MUC5AC, CEACAM5, CEACAM6, and the A33 antigen, more specifically the NPC-1 antigen on the MUC5AC protein, the 16C3 antigen on CEACAM5 and CEACAM6 proteins, and 31.1 epitope on the A33 protein. Exemplary antibodies are described in Table 1 below with the full antibody sequences being furnished herewith.

MUC5AC

MUC5AC, a mucin, is an example of a cancer-specific antigen. Mucins are high molecular weight glycoproteins with O-linked oligosaccharides attached to serine or threonine residues of the apomucin protein backbone expressed in a cell and tissue-specific pattern in normal tissues. The mucin family includes proteins that contain tandem repeat structures with a high proportion of prolines, threonines, and serines (which constitute the PTS domain). Mucins are further defined by extensive glycosylation of the PTS domain through GalNAc O-linkages at the threonine and serine residues. Each mucin has a central region with a variable number of tandem repeat with about eight amino acid residues, but there is a little similarity. There are two structurally and functionally distinct classes of mucins: secreted gel-forming mucins and transmembrane mucins. Secreted gel-forming mucins include the products of the MUC2, MUC5AC, MUC5B and MUC6 genes. See Kocer, et al. (2006) BMC Gastroenterology 6: 4; See also Hollingsworth & Swanson (2004) Nature Reviews 4: 45-60.

The human mucin (MUC) family consists of members designated MUC1 to MUC21—subclassified into secreted and transmembrane forms. The secreted mucins (e.g., MUC2, MUC5AC, MUC5B and MUC6) form a physical barrier, which acts as a mucous gel that provides protection for epithelial cells that line the respiratory and gastrointestinal tracts and form the ductal surfaces of organs such as the liver, breast, pancreas, and kidney. The transmembrane mucins (e.g., MUC1, MUC4, MUC 13 and MUC 16) have a single membrane-spanning region and contribute to the protective mucous gel through their ectodomains of (9-glycosylated tandem repeats that form rod-like structures. Kufe (2009) Nature Reviews 9: 874-885. MUC5AC expression is found on apical epithelial cells of the mucus glands of gastric antrum and body, tracheobronchial epithelium, superficial epithelium of the gallbladder and endocervix epithelium.

MUC5AC is highly expressed in adenoma. See Kocer, et al. (2006) BMC Gastroenterology 6: 4. Additionally, MUC5AC is expressed in tumors of gastrointestinal, pancreatiobiliary, and endocervical origin (e.g., colon, esophagus, liver, lung, pancreas, stomach, and uterus). See Lau, et al. (2004) Am. J. Clin Pathol. 122: 61-69. MUC5AC is also highly expressed in breast and gastric cancers. Zhang, et al. (1998) Clinical Cancer Research 4: 2669-2676. Further, MUC5AC glycan variants have been associated with pancreatic NEOplasms. Haab, et al. (May 2010) Annals of Surgery 251(5): 937-945. MUC5AC is aberrantly expressed by colorectal polyps and colorectal carcinoma. Kocer, et al. (2006) BMC Gastroenterology 6(4): 1-9.

CEACAM5 AND CEACAM6

CEACAM 5 and CEACAM6 are additional examples of cancer-specific antigens. The carcinoembryonic antigen (CEA) gene family is a member of the IgCAM superfamily including 29 related genes and pseudogenes. CEA proteins function as intercellular hemophilic and heterophilic adhesion molecules and have signaling properties. Carcinoembryonic cell adhesion molecule (CEACAM) 5 and CEACAM6 share ~90% homology in the N domain but differ in the number of IgC2-like domains (A and B domains). Both proteins contain a glycosylphosphatidylinositol (GPI) membrane anchor and are targeted to lipid rafts in apical membranes of polarized epithelial cells. CEACAM5 and CEACAM6 bind a variety of gram-negative bacteria and mediate internalization/phagocytosis, participating in innate immune defense in the intestine. Kolla, et al. (2009) Am J Physiol Lung Cell Mol Physiol 296: L1019-L1030; Lund, et al. (2003) Cancer Gene Therapy 10: 365-376.

CEACAM5 and CEACAM6 are overexpressed in many cancers (e.g., breast, ovarian, colon, pancreatic, lung, and prostate). CEACAM5 and CEACAM6 are believed to be involved in cell adhesion, cellular invasiveness, resistance to anoikis, and metastatic behavior of tumor cells. Zhang, et al. (1998) Clinical Cancer Research 4: 2669-2676; Strickland, et al. (2009) Journal of Pathology 218: 380-390; Blumenthal, et al. (2005) Cancer Research 65(19): 8809-8817; Blumenthal, et al. (2007) BMC Cancer 7(2): 1-15.

A33 Antigen Protein

A33 is another example of a cancer-specific antigen. The A33 antigen is a cell surface glycoprotein expressed in the small intestine and colonic epithelium. The A33 antigen shares homology with tight-junction associated proteins of the immunoglobulin superfamily including CAR and JAM. A33 antigen is expressed in 95% of colon tumors but not normal intestine or other organs. Ackerman, et al. (2008) Cancer Immunol Immunother 57(7): 1017-1027; Garinchesa, et al. (1996) Int. J. Oncol. 9(3): 465-71.

SUMMARY

In one aspect, the present invention relates to therapeutic use of antibodies to cancer-associated antigens ("anti-CAA antibodies"), such as NEO-201 antibodies, NEO-102 antibodies, or NEO-301 antibodies. Said anti-CAA antibodies may be used in combination with another therapeutic agent or regimen, preferably resulting in enhanced therapeutic efficacy.

In another aspect the present invention relates to the selection of patients for treatment in a therapeutic regimen involving the use of antibodies to cancer-associated antigens, such as NEO-201 antibodies. Said patient may be a patient with a cancer (such as such as breast, ovarian, cervical, or uterine cancer). The patient may be selected for treatment based upon the presence of a cancer at a specified stage, such as pre-cancer and Stage I, II, II and IV cancers including metastatic cancers. Said cancer may express the antigen bound by said anti-CAA antibody (such as NEO-201), e.g., cancer or pre-cancer of the colon, pancreas, lung (e.g., mesothelioma), prostate, skin (e.g., melanoma), breast, ovary, cervix, or uterus, or a metastatic cancer cells originating from said tissue or organ.

In another aspect the present invention relates to combination therapies for treatment of cancers that express a cancer-associate antibody. Preferred combination therapies include treatment with a subject anti-CAA antibody, such as a NEO-201 antibody, in combination with another therapeutic agent or regimen. Such treatments result in enhanced therapeutic efficacy relative to the individual therapeutic agents. Without intent to be limited by theory, it is believed that the subject anti-cancer antibodies are able to trigger apoptotic pathways, such that a combination with an agent or regimen that also target apoptosis can result in enhanced cancer cell killing. Such combination therapies may result in therapeutic effects such as promoting tumor regression, enhanced cell killing, or increasing patient survival.

Thus, in one aspect, the present disclosure provides therapeutic methods comprising treatment with an anti-CAA antibody (such as NEO-201) and another agent that targets (i.e., activates) the intrinsic apoptosis pathway.

In another aspect, the present disclosure provides therapeutic methods comprising treatment with an anti-CAA antibody (such as NEO-201) and another agent that targets (i.e., activates) the extrinsic apoptosis pathway.

One group of such agents that target the extrinsic pathway agents bind to death receptors, such as death receptor ligands (as well as fragments or analogs thereof). Additional exemplary agents that bind to death receptors include anti-death receptor antibodies, e.g., agonistic antibodies that bind to and activate said death receptor. Agonistic antibodies may also sensitize said death receptor to activation by another ligand, e.g., an endogenous or exogenous death receptor ligand. Exemplary agents include agents that target PML-RARα, DR4 (TRAIL R1), and/or DR5 (TRAIL R2). Examples of agents targeting the extrinsic pathway include TRAIL (human TRAIL polypeptide or an agonistic fragment thereof), Dr4 agonists, Dr5 agonists, and all trans retinoic acid (ATRA). Dr4 and Dr5 agonists include agonistic anti-Dr4 and anti-Dr5 monoclonal antibodies, respectively, such as Apomab, HGS-ETR1, HGS-ETR2, and HGS-TR2J.

In some embodiments, an agent that activates the extrinsic apoptotic pathway refers to substances that induce apoptosis by binding to death receptors, e.g., ligands. Exemplary ligands of death receptors are tumor necrosis factor a (TNF-alpha), tumor necrosis factor (TNF-beta, lymphotoxin alpha), lymphotoxin beta (LT-beta), TRAIL (Apo2L), CD95 (Fas, APO-I) ligand, TRAMP (DR3, Apo-3) ligand, DR4 ligand, DR6 ligand as well as fragments, variants, and derivatives of said ligands.

As noted, one ligand that activates the extrinsic apoptotic pathway is TRAIL (Apo2L). "TRAIL" (TNF-related apoptosis-inducing ligand) refers to a cytokine that is produced and secreted by most normal tissues cells. The full-length human TRAIL polypeptide is a 281 amino acid long, Type II transmembrane protein. See UniProtKB/Swiss-Prot Accession No. P50591. TRAIL causes apoptosis by binding to the death receptors DR4 and DR5. The terms "Apo2L/TRAIL," "Apo2L," "Apo-2 ligand" and "TRAIL" are used herein to refer to the TRAIL polypeptide sequence as well as biologically active fragments, deletional, insertional, or substitutional variants thereof. In some embodiments, the fragments or variants are biologically active and have at least about 80% amino acid sequence identity, more preferably at least about 90% sequence identity, and even more preferably, at least 95%, 96%, 97%, 98%, or 99% sequence identity with the human TRAIL sequence. This definition encompasses substitutional variants of TRAIL in which at least one of its native amino acids are substituted by an alanine residue. These substitutional variants include those identified, for example, as "D203A," "D218A" and "D269A." This nomenclature is used to identify Apo2L/TRAIL variants wherein the aspartic acid residues at positions 203, 218, and/or 269 are substituted by alanine residues. See U.S. Pat. No. 7,741,282. Optionally, the TRAIL variants may include one or more of the alanine substitutions, which are recited in Table I of WO 01/00832. Substitutional variants include one or more of the residue substitutions identified in Table I of WO 01/00832. The definition also encompasses a native sequence of TRAIL isolated from a TRAIL source or prepared by recombinant or synthetic methods. The TRAIL of the invention includes the polypeptides referred to as Apo2L/TRAIL or TRAIL disclosed in WO 97/01633 and WO 97/25428. In some embodiments, the TRAIL of the invention is Superkiller-TRAIL, as described by Wang, et al. ((2004) Cancer Cell 5:501). The terms "Apo2L/TRAIL" or "Apo2L" are also used to refer generally to forms of TRAIL that include monomer, dimer or trimer forms of the polypeptide. The person skilled in the art knows that the aforementioned proteins may be produced using standard techniques for the production of recombinant proteins. Alternatively, recombinant Apo2L/TRAIL is commercially available, for example from Prospec (East Brunswick, N.J.).

In other embodiments, an agent that activates the extrinsic apoptotic pathway refers to an antibody directed against one or more cellular death receptors. In particular embodiments, the antibody is a monoclonal antibody that binds to cellular death receptors and has been shown to induce cell death in different types of tumor cells. Examples of such antibodies include, but are not limited to, anti-CD95 antibody, anti-TRAIL-R1 (DR4) antibody, anti-TRAIL-R2 (DR5) antibody, anti-DR6 antibody, anti TNF-R1/2 antibody and anti-TRAMP (DR3) antibody as well as fragments or derivatives thereof. In some embodiments, the antibody is an anti-TRAIL-R1 (D4) antibody. An exemplary anti-TRAIL-R1 (D4) antibody includes, but is not limited to, mapatumumab (HGS-ETR1). Mapatumumab is an agonistic monoclonal antibody to TRAIL-R1 with apoptosis promoting and potential antitumor activities. Mapatumumab selectively binds to and activates the TRAIL cell receptor, thereby inducing apoptosis and reducing tumor growth. In another embodiment, the antibody is an anti-TRAIL-R2 (D5) antibody. An exemplary anti-TRAIL-R2 (D5) antibody includes, but is not limited to, lexatumumab (HGS-ETR2). Lexatumumab is a fully human monoclonal agonistic antibody directed against TRAIL-R2 with potential antitumor activity. Mimicking the natural ligand TRAIL, lexatumumab binds to and activates TRAIL-R2, which may trigger apoptosis in and inhibit the growth of TRAIL-R2-expressing tumor cells. Additional monoclonal antibodies that bind cellular death receptors include conatumumab (AMG655), dulanermin (AMG 951, APO2L/TRAIL, PRO1762, RG3639, rhApo2L/TRAIL), tigatuzumab (CS1008), TRAIL R (DR4-Specific Altrimer, Anaphore), HGS TR2J, LBY135, drozitumab (PRO85780, apomab), SL231, SM164 with TRAIL R2, TAS266, and the like.

In still other embodiments, an agent that activates the extrinsic apoptotic pathway refers to a chemotherapeutic agent that has been shown to activate the extrinsic apoptotic pathway. For example, treatment with DNA-damaging agents such as doxorubicin, etoposide, cisplatin or bleomycin have been shown to trigger an increase in CD95L expression, which stimulates the receptor pathway in an autocrine or paracrine manner by binding to its receptor CD95 (Friesen, et al. (1996) Nat. Med. 2:574-577; Fulda, et al. (1997) Cancer Res. 57:3823-3829; Fulda, et al. (1998) Int. J. Cancer 76:105-114; Houghton, et al. (1997) Proc. Natl. Acad. Sci. USA 94:8144-8149; Muller, et al. (1997) J. Clin. Invest. 99:403-413). The CD95 receptor/ligand system has also been implicated in thymine-less death in colon carcinoma cells following treatment with 5-fluorouracil (Houghton, et al. (1997) supra). Furthermore, upregulation of FADD and procaspase-8 has been found upon treatment with doxorubicin, cisplatin or mitomycin C in colon carcinoma cells (Micheau, et al. (1999) Biophys. Res. Commun. 256:603-611). Moreover, oxaliplatin has been shown to increase caspase-8 activity and increase Bid expression in colorectal cancer cells (DiCesare, et al. (2013) Free Radic. Biol. Med. 61C:143-150). Accordingly, in certain embodiments, the agent that activates the extrinsic apoptotic pathway is oxaliplatin.

Yet another extrinsic pathway agent is 2-deoxy-D-glucose, which has been reported to sensitize cancer cells to agents that activate the extrinsic apoptotic pathway (see U.S. Pub. No. 20140377274, which is hereby incorporated by reference in its entirety).

Further extrinsic pathway agents include drugs that target a Fas pathway, a c-FLIP pathway, 4-(4-Chloro-2-methylphenoxy)-N-hydroxybutanamide (CMH), estradiol (E2), or delta-tocotrienol.

Agents that target the intrinsic pathway include agents that target Bcl-1, Bcl-XL, Bax, BCL-Xs and/or PML-RARα. These include agents that act directly on the mitochondrial inner membrane, agents that antagonize the antiapoptotic members of the Bcl-2 protein family, and agents that enhance the activity of the proapoptotic members of the Bcl-2 family of proteins such as Bax. Examples of agents targeting the intrinsic pathway include arsenic trioxide, lonidamine (a derivative of indazole-3-carboxylic acid), antisense agents targeting Bcl-1 (such as Genasense, G3139 or oblimersen sodium), antisense agents targeting Bcl-XL, Bax, and BCL-Xs. Additional antisense agents target both Bcl-2 and Bcl-XL, or target clusterin (also known as testosterone-repressed prostate message 2). Exemplary intrinsic pathway agents also include small molecules. One group of small molecules recognizes the surface pocket of Bcl-2 or Bcl-XL, including Antimycin-A and derivatives thereof, HA14-1, and synthetic BH3 organic peptides. Additional intrinsic pathway agents include farnesyl-thiosalicylic acid (FTS), estradiol (E2), delta-tocotrienol, salinomycin, and curcumin It is to be understood that "antisense agents" refers to short interfering RNAs (siRNAs) and a number of functionally similar compound classes that utilize RNA interference (RNAi) to downregulate expression of a target gene.

Additional therapeutic agents that may be used in combination with one or more anti-CAA antibody as disclosed herein (including NEO-201, NEO-102, and NEO-301 antibodies) antimetabolites, alkylators, corticosteroids, radiation, monoclonal antibodies, platins and PARP inhibitors. Exemplary combinations include one or more of said anti-CAA antibodies (such as NEO-201) together with epirubicin, cisplatin, dacarbazine, fludarabine/cyclophosphamide, dexamethasone, doxorubicin, or other anti-cancer agents known in the art. It is to be understood that said combination may be provided together in a single formulation, or may be suitable for co-administration. Thus, methods of co-administering said agents may be provided wherein the anti-CAA antibody (such as NEO-201) and another therapeutic agent may be administered at the same time or at different times, wherein therapeutically effective dosages of both the anti-CAA antibody and said other agent may be delivered to the patient.

Further exemplary agents that may be utilized in combination with the subject anti-CAA antibodies (such as NEO-201) include FTS, CMH, TMS, and estradiol (E2). FTS invokes caspase-dependent death in cancer cells through the mitochondrial cell death pathway. FTS promotes apoptosis in MCF-7 cells and tumor xenografts. CMH is a small molecule inhibitor of Cellular FLICE (FADD-like IL-1beta-converting enzyme)-inhibitory protein (c-FLIP) and CMH can activate caspase-8 and -10 by inhibiting c-FLIP. Part of the mechanism of CMH's ability to sensitize cells to death ligands is through its ability to inhibit HDAC3, HDAC6 and HDAC8. TMS is an agent that invokes a predominantly caspase-independent death through the mitochondrial death pathway via microtubule inhibition. TMS is effective for reducing the growth of TamR resistant breast cancer tumor xenografts. Estradiol was shown to induce apoptosis of long term estrogen deprived cells through the mitochondrial cell death pathway and also the Fas death receptor pathway. Estradiol promotes apoptosis of long-term estrogen deprived cells in vitro, in xenograft models as well as patients.

Further exemplary anti-cancer agents include cytostatic agents, cytocidal agents, actinomycin D, adriamycin, arsenic trioxide, asparaginase, bleomycin, busulfan, camptosar, carboplatinum, carmustine, chlorambucil, cisplatin, corticosteroids, colicheamicin, cyclophosphamide, daunorubicin, docetaxel, doxorubicin, epirubicin, etoposide, fludarabine, fluorouracil, gemcitabina, gemcitabine, gemzar, hydroxyurea, idarubicin, ifosfamide, irinotecan, lomustine, melphalan, mercaptomurine, methotrexate, mitomycin, mitoxantrone, oxaliplatin, paclitaxel, platinol, platinex, procarbizine, raltitrexeel, rixin, steroids, streptozocin, taxol, taxotere, thioguanine, thiotepa, tomudex, topotecan, treosulfan, trihydrate, vinblastine, vincristine, vindesine, vinorelbina, vinorelbine, duanomycin, dactinomysin, esorubisin, mafosfamide, cytosine arabinoside, bis-chloroethylnitrosurea, mitomycin C, mithramycin, prednisone, hydroxyprogesterone, testosterone, tamoxifen, dacarbazine, hexamethylmelamine, pentamethylmelamine, amsacrine, chlorambudil, methylcyclohexylnitrosurea, nitrogen mustards, cyclophosphamide, 6-mercaptopurine, 6-thioguanine, cytarabine, 5-azacytidine, deoxyco-formycin, 4-hydroxyperoxycyclophosphoramide, 5-fluorouracil (5-FU), 5-fluorodeoxyuridine (5-FUdR), colchicine, trimetrexate, teni-poside, and diethylstilbestrol.

Still further exemplary anti-cancer agents include DNA damaging agents, nucleophosmin, agents which induce cellular damage as part of a synergistic process with another agent, a catalytic antibody, prodrugs, CHK1/2 inhibitor, CBP-501, AZD7762, histone deacetylase inhibitor, vorinostat, tumour necrosis factor related apoptosis inducing ligand, BH3 mimetic, ABT737, small molecule inhibitors, tyrosine kinase inhibitors, imatinib mesylate, gefitinib, erlotinib, monoclonal antibodies, rituximab and trastuzumab.

For example, other therapies or anticancer agents that may be used in combination with the inventive compounds of the present invention include, but are not limited to, surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, antibodies, aptamers, siRNAs, oligonucletoides, enzyme, ion channel and receptor inhibitors or activators to name a-few), hyperthermia and cryotherapy, agents to attenuate any adverse effects (e.g., antiemetics), and other approved chemotherapeutic drugs, including, but not limited to, alkylating drugs (e.g., mechlorethamine, chlorambucil, Cyclophosphamide, Melphalan, Ifosfamide), antimetabolites (e.g., Methotrexate), purine antagonists and pyrimidine antagonists (e.g., 6-Mercaptopurine, 5-Fluorouracil, Cytarabile, Gemcitabine), spindle poisons (e.g., Vinblastine, Vincristine, Vinorelbine, Paclitaxel), podophyllotoxins (e.g., Etoposide, Irinotecan, Topotecan), antibiotics (Doxorubicin, Bleomycin, Mitomycin), nitrosoureas (e.g., Carmustine, Lomustine), inorganic ions (e.g., Cisplatin, Carboplatin), enzymes (e.g., Asparaginase), and hormones (e.g., Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/dmglistframe).

Another composition and therapeutic regimen involve the combination of an anti-CAA antibody (such as NEO-201) with a common pathway agent. Common pathway agents are a group of agents that target both the extrinsic and intrinsic pathways, or target elements downstream of both the extrinsic and intrinsic pathway. Common pathway agents may target caspase, or other shared or common members of the extrinsic and extrinsic pathways. Exemplary common pathway agents include caspase activators, apoptin, and survivin.

Yet another composition and therapeutic regimen involve the combination of an anti-CAA antibody (such as NEO-201) with an apoptosis pathway agent. Apoptosis pathway agents (also referred to as agents that target an apoptotic pathway) are a group of agents are believed to promote apoptosis, which may potentially sensitize cells to other killing agents. These include without limitation common, extrinsic, and extrinsic pathway agents, such as agents that target p53, p53 pathway members, IκB kinase (e.g., inhibitors or antagonists thereof), IKKβ, the proteasome/ubiquitin pathway (including the 20S proteasome), the PI3K/Akt pathway (such as mTOR). Exemplary apoptosis pathway agents also include, without limitation thereto, ONY-015, INGN201, PS1145, Bortezomib, CCI779, RAD-001, and antisense therapy targeting MDM2 (which is a regulator of p53 activity).

A further composition and therapeutic regimen involve the combination of an anti-CAA antibody (such as NEO-201) with a direct cell killing agent. Direct cell killing agents include the protein mixed lineage kinase domain like (MLKL), rapamycin (RAP) or derivatives and/or analogs thereof, such as everolimus or RAD001; CCI-779, ABT578, SAR543, ascomycin (an ethyl analog of FK506), AP23573, AP23841, KU-0063794, INK-128, EX2044, EX3855, EX7518, or compounds that bind to the ATP-binding cleft of mTOR, such as AZD08055 and OSIO27.

Additionally, as further disclosed herein, combination therapies comprising an anti-CAA antibody (such as NEO-201) and exemplary other therapeutic agents are predicted to have enhanced therapeutic efficacy compared to the individual therapeutic agents. Based thereon, it is further predicted that lower dosages of said other therapeutic agent(s) can achieve the therapeutic efficacy in combination with said anti-CAA antibody (such as NEO-201), thereby allowing therapeutic benefit at a lower dosage to decrease side-effects.

The invention further provides a kit comprising said anti-CAA antibody (such as NEO-201) and said other agent. Typically said anti-CAA antibody (such as NEO-201) and/or said other agent are provided at therapeutically effective dosages for the treatment of a disease or condition, e.g., cancer such as breast, ovarian, uterine, or cervical cancer.

The invention further provides pharmaceutical compositions comprising said anti-CAA antibody (e.g., NEO-201, NEO-301, or NEO-102 antibodies) and one or more agents that target an apoptotic pathway (such as the common, extrinsic or intrinsic apoptotic pathway). In certain embodiments, the pharmaceutical compositions of the present invention further comprise one or more additional therapeutically active ingredients (e.g., chemotherapeutic and/or palliative), for example one or more agents that target an apoptotic pathway (such as the common, extrinsic or intrinsic apoptotic pathway). For purposes of the invention, the term "palliative" refers to treatment that is focused on the relief of symptoms of a disease and/or side effects of a therapeutic regimen, but is not curative. For example, palliative treatment encompasses painkillers, antinausea medications, anti-pyretics, and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

The present compounds and compositions can be administered together with hormonal and steroidal anti-inflammatory agents, such as but not limited to, estradiol, conjugated estrogens (e.g., PREMARIN, PREMPRO, AND PREMPHASE), 17 beta estradiol, calcitonin-salmon, levothyroxine, dexamethasone, medroxyprogesterone, prednisone, cortisone, flunisolide, and hydrocortisone; non-steroidal anti-inflammatory agents, such as but not limited to, tramadol, fentanyl, metamizole, ketoprofen, naproxen, nabumetone, ketorolac, tromethamine, loxoprofen, ibuprofen, aspirin, and acetaminophen; anti-TNF-alpha antibodies, such as infliximab (REMICADE) and etanercept (ENBREL).

The pharmaceutical compositions of the present invention comprise a therapeutically effective amount of a compound of the present invention formulated together with one or more pharmaceutically acceptable carriers and one or more agents that target an apoptotic pathway (such as the common, extrinsic or intrinsic apoptotic pathway). As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

TABLE 1

Antibodies which selectively bind NPC-1, 16C3, or 31-1 epitopes.

| Anitbody | Aliases | Antigen | Exemplary SEQ ID NOs | Description |
| --- | --- | --- | --- | --- |
| NPC-1 | | NPC-1 | | Murine hybridoma that expresses NPC-1 IgG1 (ATCC) |
| NEO-101 | NPC-1C, ensituximab | NPC-1 | Light Chain (SEQ ID NOs: 51, 52) LC CDRs (SEQ ID NOs: 53-55) Heavy Chain (SEQ ID NOs: 56, 57) HC CDRs (SEQ ID NOs: 58-60) | Chimeric NPC-1 antibody, engineered in CHO-DG44 production cell clone 4B7; targets a variant of MUC5AC |
| NEO-102 | | NPC-1 | Light Chain (SEQ ID NOs: 61, 62) LC CDRs (SEQ ID NOs: 63-65) Heavy Chain (SEQ ID NOs: 66, 67) HC CDRs (SEQ ID NOs: 68-70) | Chimeric NPC-1 antibody, engineered in CHO-M production cells, contains 2 amino acid changes in HC constant domain* |
| NEO-103 | | NPC-1 | Light Chain (SEQ ID NOs: 71, 72) Heavy Chain (SEQ ID NOs: 73, 74) | Humanized NPC-1 antibody |
| 16C3 | | 16C3 | Light Chain (SEQ ID NOs: 75, 76) LC CDRs (SEQ ID NOs: 77-79) Heavy Chain (SEQ ID NOs: 80, 81) HC CDRs (SEQ ID NOs: 82-94) | Murine hybridoma that expresses 16C3 IgG1 (ATCC) |
| 16C3 | Variant h16C3 antibodies | 16C3 | Light Chain (SEQ ID NOs: 85-89) Heavy Chain (SEQ ID NOs: 90-94) | Humanized 16C3 antibody |
| NEO-201 | h16C3-Abb* | 16C3 | Light Chain (SEQ ID NOs: 95, 96) LC CDRs (SEQ ID NOs: 97-99) Heavy Chain (SEQ ID NOs: 100, 101) HC CDRs (SEQ ID NOs: 102-104) | Humanized 16C3 antibody |
| 31.1 | | 31.1 | | Chimeric 31.1 antibody, produced in CHO-K cells |
| NEO-301 | 31.1C | 31.1 | Light Chain (SEQ ID NOs: 105) Heavy Chain (SEQ ID NOs: 106) | Chimeric 31.1 antibody, contains 2 amino acid changes in HC constant domain*, produced in high titer CHO-S cells |
| NEO-302 | | 31.1 | Light Chain (SEQ ID NOs: 107, 108) Heavy Chain (SEQ ID NOs: 109, 110) | Humanized 31.1 antibody |

*2 amino acid changes in the heavy chain constant domain are Proline at residue 175 to Leucine in CH1 and Methionine at residue 390 to Threonine in CH3.

In addition the present invention methods for using specific antibodies and fragments thereof to detect cancer specific antigens in vitro and in vivo are provided herein. The use of these antibodies to stage cancer prognosis, design specific treatment regimens, and to establish the efficacy of a specific treatments is also provided.

Further provided is the use of these antibodies or fragments thereof, in naked or conjugated form, alone or in association with other cancer treatment compositions (such as and one or more agents that target an apoptotic pathway (such as the common, extrinsic or intrinsic apoptotic pathway), for treating different human cancers corresponding to the specific human cancer cell lines disclosed herein.

These antibodies, NEO-101 (previously referred to by the Assignee as NPC-1), NEO-102, NEO-201 (previously referred to by the Assignee as h16C3-Abb*) and NEO-301 (previously referred to as 31.1) are summarized in Table 1 and the sequences thereof are further described herein.

NEO-101 specifically binds to an epitope comprised in MUC5AC, in particular it recognizes a repeated epitope comprised in the MUC5AC antigen that is specifically expressed on different human tumors which epitope comprises specific carbohydrate residues ("glycotope"). NEO-201 specifically binds to epitopes comprised of specific amino acid residues which are comprised in the CEACAM5 and CEACAM6 antigens, which antigens and the corresponding NEO-201 epitopes are also expressed on different human tumors. Finally, NEO-301 specifically binds to an epitope contained in the A33 antigen which antigen and corresponding epitope is similarly expressed by different human tumors.

NEO-102 is a genetically engineered chimeric monoclonal antibody that has been manufactured from a recombinant Chinese hamster ovary (CHO) cell production clone. In an exemplary embodiment this antibody may be formulated at 10.0 mg/mL in 25 mM sodium citrate, 150 mM sodium chloride, 0.1% polysorbate-80.

NEO-201 is a genetically engineered humanized monoclonal antibody that has been manufactured from a recombinant CHO cell production clone. In an exemplary embodiment this antibody may be formulated at 10.4 mg/mL in 20 mM sodium phosphate, 150 mM sodium chloride pH7.2.

NEO-301 a genetically engineered chimeric monoclonal antibody that has been manufactured from a recombinant CHO cell production clone. In an exemplary embodiment this antibody may be formulated at 11.5 mg/mL in 20 mM sodium phosphate, 150 mM sodium chloride pH7.2.

BRIEF DESCRIPTION OF THE DRAWINGS

FIG. 1. NEO-101, NEO-201 and NEO-301 Antigen Expression by Human Normal and Cancer Cell Lines. NEO-101, NEO-201 and NEO-301 specific antigen expression in various cell lines were detected by Flow Cytometry. Viable cell suspensions were incubated with primary antibody NEO-101, NEO-201 and NEO-301 separately at 10 ug/mL. Human IgG (10 ug/mL) was used as negative control. Goat anti-human IgG (Fc)-phycoerythrin conjugate was used for primary antibody detection; 7-ADD was used for excluding dead cells from analysis. The staining was measured by Flow Cytometry (Guava instrument, Millipore). Median fluorescent intensity (MFI) and % of stained cells was used for determining presence of specific antigen on each cell line.

FIG. 2. Immunohistochemistry results from cancer tissue arrays. Immunohistochemistry method (IHC) was used for determining the presence of NEO-101/102, NEO-201 and NEO-301 antigens on paraffin microarrays and tissues. These primary antibodies (NEO-101/NEO-102, NEO-201 and NEO-301) were biotinylated prior to use. Paraffin tissue Microarrays and slides of tissues were reacted with the primary Ab after inactivating endogenous peroxidase and blocking the slides. Staining was detected with streptavidin-horseradish peroxidase conjugate and visualized with chromogen. Biotinylated human IgG1 was used as negative control and mouse anti-human cytokeratin monoclonal antibody was used as positive control. Antibody staining is measured as % and intensity of tumor epithelial cells and luminal secretion within the whole tissue section.

FIG. 3. Summary of NEO-101, NEO-102 and NEO-301 IHC Results from normal colon and pancreatic paraffin tissues. Normal cell samples as indicated were stained using similar methods as in FIG. 2 above. ADJ: adjacent.

DETAILED DESCRIPTION

The present disclosure provides anti-cancer antibodies which selectively bind NPC-1, 16C3, or 31-1 epitopes, which may comprise NEO-101, NEO-102, NEO-103, NEO-201, NEO-301, NPC-1, 16C3, or 31-1 having polypeptide sequences identified in Table 1, supra, or a variant thereof.

The present disclosure also provides therapeutic compositions comprising said anti-cancer antibody and another therapeutic agent, such as one or more agents that target an apoptotic pathway (such as the common, extrinsic or intrinsic apoptotic pathway). Preferred agents, when co-administered with the anti-cancer antibody, result in enhanced therapeutic efficacy in the patient, e.g., increased cancer cell killing, tumor regression, and/or increased patient survival.

The present disclosure also provides therapeutic methods comprising administering said anti-cancer antibody and another therapeutic regimen to a patient in need thereof. Said therapeutic regimen may include administration of an anti-cancer agent. Said therapeutic regimen may include radiotherapy.

Preferably said anti-cancer agent targets one or more apoptotic pathways in the cell, e.g., the intrinsic pathway, extrinsic pathway, or the common pathway. Said agent may target a molecule that participates in more than one of the extrinsic, intrinsic, and common pathways. Without intent to be limited by theory, it is believed that NEO-201 and other anti-CAA antibodies (such as NEO-201) disclosed herein are able to kill cells by activating one or more apoptotic pathways, such that a combination with an agent or regimen that targets the apoptotic pathway can result in enhanced cancer cell killing. Such combination therapies may result in therapeutic effects such as promoting tumor regression, enhanced cell killing, or increasing patient survival.

Said cancer may express the antigen bound by said anti-CAA antibody (such as NEO-201), e.g., cancer or pre-cancer of the colon, pancreas, lung (e.g., mesothelioma), prostate, skin (e.g., melanoma), breast, ovary, uterus, cervix, or a metastatic cancer cells originating from said tissue or organ.

Exemplary embodiments of the invention provide a therapeutic method comprising administering an effective amount of said modified antibody to a patient, optionally in combination with another therapy such as and one or more agents that target an apoptotic pathway (such as the common, extrinsic or intrinsic apoptotic pathway). Said modified antibody may also contain one or more modifications which increase effector functions. For example, said antibody may contain one or more modifications that increase ADCC, which may result in increased ADCC relative to the same antibody sequence lacking said modification. As a further example, said antibody may contain one or modifications that result in increased binding to one or more Fc receptors, thereby resulting in increased Fc receptor binding relative to the same antibody sequence lacking said modification. As a yet further example, said antibody may contain one or more modifications that result in increased CDC, thereby resulting in increased CDC relative to the same antibody sequence lacking said modification.

In another aspect, the disclosure provides a therapeutic method comprising administering an effective amount of an antibody to a cancer-associated antigen in combination with one or more chemotherapeutic agents such as oxaliplatin, irinotecan, topotecan, leucovorin, carmustine, vincristine, fluorouracil, streptozocin, and gemcitabine, wherein said antibody is preferably an antibody to the NPC-1, 16C3, or 31.1 antigen, such as one of the antibodies identified in Table 1 or a fragment or variant thereof and optionally one or more agents that target an apoptotic pathway (such as the common, extrinsic or intrinsic apoptotic pathway). In yet another aspect, the disclosure provides a therapeutic method comprising administering an effective amount of an antibody to a cancer-associated antigen and optionally one or more agents that target an apoptotic pathway (such as the common, extrinsic or intrinsic apoptotic pathway) in combination with radiation therapy wherein said antibody is preferably an antibody to the NPC-1, 16C3, or 31.1 antigen, such as one of the antibodies identified in Table 1 or a fragment or variant thereof. Said antibody may or may not contain an Fc modification that increases ADCC or another effector function (e.g., as described above). Preferably said antibody in combination exhibits an enhanced or synergistic effect on treatment outcome relative to said antibody alone.

The term "apoptosis" refers to programmed cell death mediated by biochemical pathways that can be induced by various means. A "pro-apoptotic" agent or drug is a bioactive agent or drug that produces a biochemical effect that results in programmed cell death. Apoptosis can be caused or induced by intrinsic or extrinsic pathways or mechanisms, as further described herein. The "extrinsic" apoptosis pathway involves death receptors, and this pathway is activated by ligands that bind to the death receptors. The "intrinsic" apoptosis pathway involves mitochondrial pathways that initiate apoptosis.

Apoptosis is believed to be initiated through the extrinsic and intrinsic pathways (reviewed in Fulda et al., Oncogene (2006) 25, 4798-4811; Ghobrial et al., CA: A Cancer Journal for Clinicians, Volume 55, Issue 3, pages 178-194, May/June 2005, each of which is hereby incorporated by reference in its entirety). The extrinsic pathway (also referred to as the cytoplasmic pathway) can be triggered through the Fas death receptor and includes the membrane-bound Fas ligand (FasL), Fas complexes, and the Fas-associated death domain. Activation of the extrinsic pathway can be initiated with the ligation of cell surface receptors called death receptors (DRs). Death receptors of the tumor necrosis factor (TNF) receptor superfamily include CD95 (APO-1/Fas) or TNF-related apoptosis-inducing ligand (TRAIL), TNF receptor 1 (TNFRI), and TRAIL-R2. When a death stimulus triggers the pathway, the membrane-bound FasL interacts with the inactive Fas complexes and forms a death-inducing signaling complex. The Fas death-inducing signaling complex contains the adaptor protein Fas-associated death domain protein and caspases 8 and 10 and leads to activation of caspase 8, which in turn can activate the rest of the downstream caspases. In some cells, the activation of caspase 8 may be sufficient to execute death, while in other cell types, caspase 8 may interact with the intrinsic apoptotic pathway by cleaving Bid (a proapoptotic member of the Bcl-2 family), leading to the subsequent release of cytochrome-c.

The intrinsic pathway (also called the mitochondrial pathway) involves the release of cytochrome-c from the mitochondria and activation of the death signal, involving Bcl-2 family proteins, Apaf-1, and activation of procaspase-9 to caspase-9. The Bcl-2 family includes proapoptotic members such as Bax, Bak, Bad, Bcl-Xs, Bid, Bik, Bim, and Hrk, and antiapoptotic members such Bcl-2, Bcl-XL, Bcl-W, Bfl-1, and Mcl-1. Antiapoptotic Bcl-2 members are believed to act as repressors of apoptosis by blocking the release of cytochrome-c, whereas proapoptotic members act as promoters. These effects are though to be more dependent on the balance between Bcl-2 and Bax than on Bcl-2 quantity alone. More generally, the intrinsic pathway may be activated by stimulating or agonizing a pro-apoptotic member of the intrinsic pathway, and/or by antagonizing or downregulating anti-apoptotic members of the intrinsic pathway.

Both the extrinsic and intrinsic pathways converge to a final common or overlapping pathway involving the activation of caspases that cleave regulatory and structural molecules and culminate in the death of the cell.

Experimentally, cell killing can be considered to occur through the extrinsic pathway if it is dependent on caspase 8 but less dependent on or independent from caspase 3. Conversely, cell killing is considered to occur through the intrinsic pathway if it is dependent on caspase 3 but less dependent on or independent from caspase 8. Activation of either caspase may be detected using a luciferase-based caspase assay such as Caspase-Glo®, e.g., to measure activity of caspases-3/7 (Caspase-Glo® 3/7 Assay Systems, Promega) or caspase-8 (Caspase-Glo® 8 Assay System, Promega). Detected activation of a given caspase provides evidence of its involvement in cell killing by an anti-CAA antibody (such as NEO-201) or other agent. Additionally, Caspase 3 and caspase 8 expression may experimentally manipulated (such as using RNAi knock-down) to experimentally test whether a cell killing mechanism depends on one or the other of caspase 3 and caspase 8, and thus identify a cell killing mechanism as dependent on the extrinsic or intrinsic pathway. On the other hand, cell killing that does not depend on caspase 3 or caspase 8 is considered to involve direct cell killing.

RNA interference (RNAi) broadly refers to silencing or "knock down" the expression of a targeted gene. The mechanism of gene silencing in RNAi is believed to be based on degrading or otherwise preventing the transcription or translation of mRNA in a sequence specific manner. In terms of the application of this technology to selectively knocking down gene expression, exogenous double stranded RNA (dsRNA) (including structural analogs of RNA) specific to a gene sought to be knocked down can be introduced into the intracellular environment. Mechanisms by which RNAi molecules can interfere with gene expression have been described in the literature. In brief, it has been reported that once the dsRNA enters the cell, it is typically cleaved by an RNaseIII-like enzyme, Dicer, into double stranded small interfering RNAs (siRNAs) 21-23 nucleotides in length that contain 2 nucleotide overhangs on the 3' ends. In an ATP dependent step, the siRNAs become integrated into a multisubunit protein complex known as the RNAi induced silencing complex (RISC), which guides the siRNAs to the target RNA sequence. The siRNA unwinds and the antisense strand remains bound to RISC and directs degradation of the complementary target mRNA sequence by a combination of endo- and exonucleases. However, whereas the RNAi mechanism was originally identified in the context of its role as a microbial defence mechanism in higher eukaryotes, it is also known that RNAi based gene expression knockdown can also function as a mechanism to regulate endogenous gene expression for research or therapeutic purposes. MicroRNA (miRNA) is a form of endogenous single-stranded RNA which is typically 20-25 nucleotides and is endogenously transcribed from DNA, but not translated into protein. The DNA sequence that codes for an miRNA gene generally includes the miRNA sequence and an approximate reverse complement. When this DNA sequence is transcribed into a single-stranded RNA molecule, the miRNA sequence and its reverse-complement base pair to form a double stranded RNA hairpin loop, this forming the primary miRNA structure (pri-miRNA). A nuclear enzyme cleaves the base of the hairpin to form pre-miRNA. The pre-miRNA molecule is then actively transported out of the nucleus into the cytoplasm where the Dicer enzyme cuts 20-25 nucleotides from the base of the hairpin to release the mature miRNA.

The term "short interfering nucleic acid," "siNA," "short interfering RNA," "siRNA," "short interfering nucleic acid molecule," "short interfering oligonucleotide molecule," or "chemically modified short interfering nucleic acid molecule" as used herein refers to any nucleic acid molecule capable of inhibiting or down regulating gene expression or viral replication, for example by mediating RNA interference "RNAi" or gene silencing in a sequence-specific manner; see for example Bass, 2001, Nature 411, 428-429;

Elbashir et al., 2001, Nature 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science 297, 1818-1819; Volpe et al., 2002, Science 297, 1833-1837; Jenuwein, 2002, Science 297, 2215-2218; and Hall et al., 2002, Science 297, 2232-2237; Hutvagner and Zamore, 2002, Science 297, 2056-60; McManus et al., 2002, RNA 8, 842-850; Reinhart et al., 2002, Gene & Dev. 16, 1616-1626; and Reinhart & Bartel, 2002, Science 297, 1831). For example, the siNA may be a double-stranded polynucleotide molecule comprising complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof.

Exemplary short interfering nucleic acids include long double stranded RNA (dsRNA), hairpin double stranded RNA (hairpin dsRNA), short interfering RNA (siRNA), short hairpin RNA (shRNA), micro RNA/small temporal RNA (miRNA/stRNA), miRNAs which mediate spatial development (sdRNAs), the stress response (srRNAs) or cell cycle (ccRNAs), RNA oligonucleotides designed to hybridize and prevent the functioning of endogenously expressed miRNA or stRNA or exogenously introduced siRNA. RNAi molecules for silencing a given gene of interest can be designed by methods known in the art. In addition to exogenous introduction of an RNAi molecule, a cell may also be caused to express a given RNAi molecule from an exogenously introduced expression construct, wherein desired the sequences are operably linked to an inducible or constitutive promoter. Said expression construct may introduced into said cell in a manner resulting in stable (e.g., genomic integration) or transient (e.g., extrachromosomal) presence of the construct. Additionally included are modified RNA analog molecules containing a sugar backbone or a non-sugar backbone. A sugar backbone may comprise any naturally occurring sugar as well as non-naturally occurring sugars. Examples of naturally occurring sugars include, but are not limited to, ribose, deoxyribose, and/or 2-deoxyribose. Sugar units of a backbone may be modified such that the modified sugar backbone is resistant to cleavage. The sugars of a backbone may be modified by methods known in the art, for example, to achieve resistance to nuclease cleavage. Examples of modified sugars include, but are not limited to, 2'-O-alkyl riboses, such as 2'-O-methyl ribose, and 2'-O-allyl ribose. The sugar units may be joined by phosphate linkers. Typical sugar units of the invention may be linked to each other by 3'-5', 3'-3', or 5'-5' linkages. Additionally, 2'-5' linkages are also possible if the 2' OH is not otherwise modified. A non-sugar backbone may comprise any non-sugar molecule to which bases may be attached. Non-sugar backbones are known in the art. Examples include, but are not limited to, morpholino and peptide nucleic acids (PNAs). A morpholino backbone is made up of morpholino rings (tetrahydro-1,4-oxazine) and may be joined by non-ionic phosphorodiamidate groups. Modified morpholinos known in the art may be used in the present invention. PNAs result when bases are attached to an amino acid backbone by molecular linkages. Examples of such linkages include, but are not limited to, methylene carbonyl, ethylene carbonyl, and ethyl linkages. The amino acids may be any amino acid, natural or non-natural, modified or unmodified, and are preferably alpha amino acids. The amino acids may be identical or different from one another. One non-limiting example of a suitable amino acid includes an amino alkyl-amino acid, such as (2-aminoethyl)-amino acid.

Extrinsic Pathway. "Agents that target the extrinsic pathway," "agents that target the extrinsic apoptotic pathway" "agents that activate the extrinsic pathway," "agents that activate the extrinsic apoptotic pathway," "extrinsic pathway agents," "extrinsic apoptotic pathway agents" (as well as variants of these terms) are used interchangeably herein and refer to the group of agents that activate or sensitize the extrinsic apoptotic pathway of a cell, such as a cancer cell.

Intrinsic Pathway. "Agents that target the intrinsic pathway," "agents that target the intrinsic apoptotic pathway" "agents that activate the intrinsic pathway," "agents that activate the intrinsic apoptotic pathway," "intrinsic pathway agents," "intrinsic apoptotic pathway agents" (as well as variants of these terms) are used interchangeably herein and refer to the group of agents that activate or sensitize the intrinsic apoptotic pathway of a cell, such as a cancer cell.

Dosage Forms

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying agents, suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In order to prolong the effect of a drug, it may be desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons. Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight (0.05 to 4.5 mg/m$^2$). An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

In certain embodiments, a composition may comprise active agents, such as an antibody of the disclosure and one or more agents that target an apoptotic pathway (such as the common, extrinsic or intrinsic apoptotic pathway), in amounts that exhibit an enhanced or synergistic effect relative to said antibody alone. Said enhanced or synergistic effect may be determined based on observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration to a subject suffering from or susceptible to a disease or disorder.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the invention and a co-agent, are both administered to a patient simultaneously in the form of a single entity or dosage. The term "non-fixed combination" means that the active ingredients, e.g., a compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The agents or salts thereof may be formulated into pharmaceutical compositions for administration to animals or humans. These pharmaceutical compositions, which comprise an amount of the protein inhibitor effective to treat or prevent a cancer and a pharmaceutically acceptable carrier, are another embodiment of the present invention.

Radiation therapy (also referred to as radiotherapy) is the medical use of radiation to treat malignant cells, such as cancer cells. This radiation can have an electromagnetic form, such as a high-energy photon, or a particulate form, such as an electron, proton, neutron, or alpha particle. A common form of radiation used in practice today is high-energy photons. Photon absorption in human tissue is determined by the energy of the radiation, as well as the atomic structure of the tissue in question. The basic unit of energy used in radiation oncology is the electron volt (eV); $10^3$ eV=1 keV, $10^6$ eV=1 MeV. Three interactions can be involved in photon absorption in tissue: the photoelectric effect, Compton effect, and pair production.

In the photoelectric effect, an incoming photon transfers energy to a tightly bound electron. The photon transfers practically all of its energy to the electron and ceases to exist. The electron departs with most of the energy from the photon and begins to ionize surrounding molecules. This interaction depends on the energy of the incoming photon, as well as the atomic number of the tissue; the lower the energy and the higher the atomic number, the more likely that a photoelectric effect will take place. The energy range in which the photoelectric effect predominates in tissue is about 10-25 keV.

The Compton effect is the most important photon-tissue interaction for the treatment of cancer. In this case, a photon collides with a "free electron," i.e, one that is not tightly bound to the atom. Unlike the photoelectric effect, in the Compton interaction both the photon and electron are scattered. The photon can then continue to undergo additional interactions, albeit with a lower energy. The electron begins to ionize with the energy given to it by the photon. The probability of a Compton interaction is inversely proportional to the energy of the incoming photon and is independent of the atomic number of the material. The Compton effect dominates in the range of about 25 keV-25 MeV and is therefore the most common interaction occurring clinically, as most radiation treatments are performed at energies of about 6-20 MeV.

In pair production, a photon interacts with the nucleus of an atom. The photon gives up energy to the nucleus and, in the process, creates a positron-electron pair of particles. The positive electron (positron) ionizes until it combines with a free electron in positron-electron annihilation. This positron-electron annihilation generates two photons that travel in opposite directions. The probability of pair production is proportional to the logarithm of the energy of the incoming photon and is dependent on the atomic number of the material. The energy range in which pair production dominates is greater than or equal to 25 MeV. This interaction occurs to some extent in routine radiation treatment with high-energy photon beams.

With the advent of high-energy linear accelerators, electrons have become a viable option in treating superficial tumors up to a depth of about 5 cm. Electron depth dose characteristics are unique in that they produce a high skin dose but exhibit a falloff after only a few centimeters.

Electron absorption in human tissue is greatly influenced by the presence of air cavities and bone. The most common clinical uses of electron beams include the treatment of skin lesions, such as basal cell carcinomas, and boosting of areas that have previously received photon irradiation, such as postoperative lumpectomy or mastectomy scar in breast cancer patients, as well as select nodal areas in the head and neck.

Dose computation algorithms are used for radiation therapy planning to help ensure that the desired dose is delivered to a specific patient. Dose computation includes two parts: a source model and a transport model. The source model provides the incident fluence. The transport model computes the dose that results from the incident fluence. The three main transport algorithms in the order of increasing accuracy/decreasing performance are pencil beam, superposition/convolution, and Monte Carlo. Superposition/convolution is the current clinical standard method of calculating radiation dose for external beam radiation therapy.

In recent years, treatment quality has been increased by the use of intensity modulation. This technique uses a multi-leaf collimator to define multiple apertures from a single beam direction providing the ability to vary the intensity of radiation across the beam. This technique allows conforming radiation treatment to the shape of the target and avoid critical structures while drastically increasing the number of beam parameters. The treatment planning system can optimize, through multiple iterations of dose calculations, an objective function having the drastically increased number of beam parameters. In practice, the treatment planner repeats the optimizations multiple times in order to achieve the best results possible for the patient.

This clinical workflow extends to more complex techniques such as volumetric modulated arc therapy (Otto, K., Med. Phys. 35, 310-317, 2008), intensity modulated arc therapy (Yu, C. X., Phys. Med. Biol. 40, 1435-1449, 1995), and adaptive radiation therapy (Yan, D., Vicini, F., Wong, J., Martinez, A, Phys. Med. Biol. 42, 123-132, 1997). Real-time radiation therapy (the ability to scan, re-plan and treat every patient daily) may also be performed. A thorough review of dose calculation in radiation therapy is available from Ahnesjo et al. (Ahnesjo, A., Aspradakis, M, Phys. Med. Biol. 44, R99-R1551999).

Additionally provided are diagnostic methods comprising administering said modified antibody to a patient and detecting said antibody in said patient.

Exemplary embodiments of the invention provide compositions comprising said modified antibody (such as therapeutic compositions or diagnostic compositions), which compositions may comprise a pharmaceutically acceptable carrier, and additionally may comprise one or more additional therapeutic agents, such as an anti-cancer agent.

Further exemplary embodiments of the invention provide nucleic acids encoding said modified antibodies are provided. Additionally provided are cells (such as mammalian, prokaryotic, yeast, or other eukaryotic cells) or vectors comprising a nucleic acid encoding said modified antibody.

Additional exemplary embodiments of the invention provide methods of making said modified antibodies, comprising expressing a nucleic acid encoding said modified antibody.

In another aspect, this disclosure provides methods of detecting a cancer cell that expresses a cancer-associated antigen. Detecting the expression of cancer-associated antigen (e.g., using an antibody to MUC5AC, CEACAM5, CEACAM6, or the A33 antigen) may be used for diagnosis and staging of cancers (e.g., in radioimaging). For example, the level or extent of expression of one or more of these cancer-associated antigens may indicate the stage of cancer, may be correlated with patient outcome, or may be predictive of the outcome of different treatment options.

Currently, depending on the stage of the cancer, cancer treatment involves one or a combination of the following therapies: surgery to remove the cancerous tissue, radiation therapy, and chemotherapy. Detection of cancer cells using an antibody to a cancer-associated antigen (such as an antibody to MUC5AC, CEACAM5, CEACAM6, or the A33 antigen) can be used in conjunction with one or more therapies. Therapy may be targeted to the cancer cells thereby promoting effective treatment and/or reducing the effect on normal non-cancerous tissue. For example, cells expressing a cancer-associated antigen may be targeted using radiotherapy, surgery, and/or cryotherapy. The therapeutic course (e.g., regimen and dosages of radiotherapy, surgical plan, or course of cryotherapy) that are therapeutically effective will depend on the particular cancer being treated, the extent of the disease and other factors familiar to the physician of skill in the art and can be determined by the physician.

Expression of a cancer-associated antigen (such as MUC5AC, CEACAM5, CEACAM6, or the A33 antigen) may be evaluated using an in vivo diagnostic assay, e.g., by administering a molecule (such as an antibody) which binds the molecule to be detected and is tagged with a detectable label (e.g., a radioactive isotope or a fluorescent label) and externally scanning the patient for localization of the label. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody. Aside from the above assays, various in vivo and in vitro assays for detecting the presence of a cancer-associated antigen are available to the skilled practitioner. The cancer-associated antigen (such as MUC5AC, CEACAM5, CEACAM6, or the A33 antigen) may be present on the cell surface. Alternatively or in addition the cancer-associated antigen (or a precursor thereof) may be produced and secreted at detectable levels. For example, the cancer-associated antigen may be detected in a biological fluid such as serum, e.g, using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., J. Immunol. Methods 132: 73-80 (1990)).

The antibodies may also be used for purification or immunoprecipitation of the cancer-associated antigen from cells or other samples, for detection and quantitation of cancer-associated antigen in vitro, e.g., in an ELISA or a Western blot, to kill and eliminate cancer-associated antigen-expressing cells from a population of mixed cells, e.g., as a step in the purification of other cells.

In another aspect, the invention provides a diagnostic kit comprising a NPC-1, 16C3, or 31.1 antibody such as a NEO-102, NEO-201, or NEO-301 antibody or variant thereof. In one embodiment, the polypeptide may be directly or indirectly fixed to a solid phase support, such as a bead, plate, matrix, polymer, test tube, sheet, culture dish, or test strip. In another embodiment, the solid support may be an array.

In another embodiment, the invention provides an antibody which binds, preferably specifically, to any of the above or below described polypeptides. Optionally, the antibody is a monoclonal antibody, antibody fragment, chimeric antibody, humanized antibody, single-chain antibody or antibody that competitively inhibits the binding of an antibody disclosed herein to its respective antigenic epitope. Antibodies of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like.

The antibodies may optionally be produced in mammalian cells (such as CHO cells), bacterial cells, yeast cells, or other cells or using cell-free methods as known in the art.

For diagnostic purposes, the antibodies of the present invention may be detectably labeled, attached to a solid support, or the like. For example, the antibody may be labeled by conjugation to a radiolabel such as $^{111}$In or $^{86}$Y. In exemplary embodiments the $^{111}$In or $^{86}$Y (or another radiolabel) may be conjugated to an antibody using the acyclic chelate CHX-A"-DTPA. These radiolabels and conjugation methods are only intended to be illustrative, as alternative radiolabels and/or alternative conjugation methods may be utilized.

In yet another embodiment, the invention concerns an article of manufacture comprising a container and a composition of matter contained within the container, wherein the composition of matter may comprise an antibody as described herein (such as an antibody to MUC5AC, CEACAM5, CEACAM6, or the A33 antigen). The article may further optionally comprise a label affixed to the container, or a package insert included with the container, that refers to the use of the composition of matter for the therapeutic treatment or diagnostic detection of a tumor.

Another embodiment of the present invention is directed to a method for inhibiting the growth of a cell that expresses a cancer-associated antigen as described herein (such as MUC5AC, CEACAM5, CEACAM6, or the A33 antigen), wherein the method comprises contacting the cell with an antibody that binds to the cancer-associated antigen and with one or more agents that target an apoptotic pathway (such as the common, extrinsic or intrinsic apoptotic pathway), and wherein the binding of the antibody to the cancer-associated antigen causes inhibition of the growth of the cell expressing the cancer-associated antigen. In preferred embodiments, the cell is a cancer cell and binding of the antibody to the cancer-associated antigen causes death of the cell expressing the cancer-associated antigen. Optionally, the antibody is a monoclonal antibody, antibody fragment, chimeric antibody, humanized antibody, or single-chain antibody. Antibodies employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies employed in the methods of the present invention may optionally be produced in CHO cells or bacterial cells.

Yet another embodiment of the present invention is directed to a method of therapeutically treating a mammal having a cancerous tumor comprising cells that express a cancer-associated antigen as described herein (such as MUC5AC, CEACAM5, CEACAM6, or the A33 antigen), wherein the method comprises administering to the mammal a therapeutically effective amount of an antibody that binds to the cancer-associated antigen and one or more agents that target an apoptotic pathway (such as the common, extrinsic or intrinsic apoptotic pathway), thereby resulting in the effective therapeutic treatment of the tumor. Optionally, the antibody is a monoclonal antibody, antibody fragment, chimeric antibody, humanized antibody, or single-chain antibody. Antibodies employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies employed in the methods of the present invention may optionally be produced in CHO cells or bacterial cells.

Yet another embodiment of the present invention is directed to a method of determining the presence of a cancer-associated antigen as described herein (such as MUC5AC, CEACAM5, CEACAM6, or the A33 antigen) in a sample suspected of containing the cancer-associated antigen, wherein the method comprises exposing the sample to an antibody that binds to the cancer-associated antigen and determining binding of the antibody to the cancer-associated antigen in the sample, wherein the presence of such binding is indicative of the presence of the cancer-associated antigen in the sample. Optionally, the sample may contain cells (which may be cancer cells) suspected of expressing the cancer-associated antigen. The antibody employed in the method may optionally be detectably labeled, attached to a solid support, or the like.

A further embodiment of the present invention is directed to a method of diagnosing the presence of a tumor in a mammal, wherein the method comprises detecting the level of expression of a cancer-associated antigen (a) in a test sample of tissue cells obtained from said mammal, and (b) in a control sample of known normal non-cancerous cells of the same tissue origin or type, wherein a higher level of expression of the cancer-associated antigen in the test sample, as compared to the control sample, is indicative of the presence of tumor in the mammal from which the test sample was obtained.

Another embodiment of the present invention is directed to a method of diagnosing the presence of a tumor in a mammal, wherein the method comprises (a) contacting a test sample comprising tissue cells obtained from the mammal with an antibody that binds to a cancer-associated antigen as described herein (such as an antibody to MUC5AC, CEACAM5, CEACAM6, or the A33 antigen) and (b) detecting the formation of a complex between the antibody and the cancer-associated antigen in the test sample, wherein the formation of a complex is indicative of the presence of a tumor in the mammal. Optionally, the antibody employed is detectably labeled, attached to a solid support, or the like, and/or the test sample of tissue cells is obtained from an individual suspected of having a cancerous tumor.

Yet another embodiment of the present invention is directed to a method of binding an antibody to a cell that expresses a cancer-associated antigen as described herein (such as MUC5AC, CEACAM5, CEACAM6, or the A33 antigen), wherein the method comprises contacting a cell that expresses a cancer-associated antigen with said antibody under conditions which are suitable for binding of the antibody to said cancer-associated antigen and allowing binding therebetween. In preferred embodiments, the antibody is labeled with a molecule or compound that is useful for qualitatively and/or quantitatively determining the location and/or amount of binding of the antibody to the cell.

Except where otherwise provided the techniques and procedures are generally performed according to conventional methods well known in the art and as described in various general and more specific references that are cited and discussed throughout the present specification. See, e.g., Sambrook, et al (2001) Molecular Cloning: A Laboratory Manual [3rd Ed] Cold Spring Harbor Laboratory Press. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

It is a further object of the invention to provide a method of treating a cancer type corresponding to any of the human cell lines comprised in Table 2 and FIG. 1, or any cancer comprised in Table 2 and FIG. 1 other than colon, pancreatic or lung cancer, by the administration of a therapeutically effective amount of an antibody having the epitopic specificity of NEO-102, NEO-201 or NEO-301 or a fragment thereof and one or more agents that target an apoptotic pathway (such as the common, extrinsic or intrinsic apoptotic pathway).

It is another object of the invention to provide a method of treating a cancer corresponding to any of the human cell lines comprised in Table 2 and FIG. 1, or any cancer comprised in Table 2 and FIG. 1 other than colon, pancreatic or lung cancer, by the administration of a therapeutically effective amount of an antibody that competes with NEO-102, NEO-201 or NEO-301 or a fragment thereof and one or more agents that target an apoptotic pathway (such as the common, extrinsic or intrinsic apoptotic pathway).

It is also an object of the invention to provide a method of detecting a cancer, such as breast, ovarian, cervical, or uterine cancer, by the administration of a diagnostically effective amount of an antibody having the epitopic specificity of NEO-102, NEO-201 or NEO-301 or a fragment thereof.

It is also an object of the invention to provide a method of detecting a cancer corresponding to any of the human cell lines comprised in Table 2 and FIG. 1, or any cancer comprised in Table 2 and FIG. 1 other than colon, pancreatic or lung cancer, by the administration of a diagnostically effective amount of an antibody that competes with NEO-102, NEO-201 or NEO-301 or a fragment thereof.

It is another object of the invention to provide a method for diagnosing cancer in a subject by detecting NEO-102, NEO-201 or NEO-301 antigen-bearing cancer cells which comprises: (a) obtaining a sample from a subject suspected of having cancer; (b) contacting the sample with NEO-102, NEO-201 or NEO-301 or a fragment of such antibody, which is detectably labeled, under appropriate conditions so as to produce an antibody-antigen complex or a fragment-antigen complex comprising the detectably labeled antibody or fragment bound to any tumor cells expressing NEO-102, NEO-201 or NEO-301 antigen in the sample; (c) removing any labeled antibody or fragment not in the antibody antigen complex or fragment-antigen complex formed in step (b); and (d) determining the presence of any antibody antigen complex or any fragment-antigen complex by detecting the detectably labeled antibody or Fab fragment, the presence of antibody antigen complex or Fab fragment-antigen complex being diagnostic of cancer so as to thereby diagnose cancer in the subject, preferably wherein the detectably labeled antibody or Fab fragment is labeled with a radioactive isotope, an enzyme, a dye, a biotin, a fluorescent label or a chemiluminescent label.

It is also an object of the invention to provide a method for monitoring progression of a cancer, wherein the cancer is one that comprises cells that express at least one tumor-associated antigenic epitope specifically bound by at least one of the NEO-102, NEO-201 or NEO-301 antibodies or fragments thereof in a subject, comprising: a) administering to a subject diagnosed with cancer that comprises cells that express at least one tumor-associated antigenic epitope specifically bound by at least one of the NEO-102, NEO-201 or NEO-301 antibodies, an antibody or fragment directed to an epitope specifically bound by at least one of NEO-102, NEO-201 or NEO-301 or a fragment of such antibody, and wherein the antibody or fragment is detectably labeled, under appropriate conditions so as to bind the antibody or the fragment to NEO-101, NEO-201 or NEO-301 antigen bearing cells in the subject; b) determining the presence of detectably labeled antibody or fragment bound to the surface of cells in the subject; c) comparing the presence of the detectably labeled antibody or fragment bound to cells in step (b) with the presence of detectably labeled antibody bound to cells at (i) diagnosis time or (ii) after treatment, wherein a greater presence of detectably labeled antibody or fragment bound to cells in step (b) than at (i) diagnosis time or (ii) after treatment, indicates progression of the cancer in the subject and a lesser presence of detectably labeled antibody or fragment bound to cells in step (b) than at (i) diagnosis time or (ii) after treatment indicates regression of the cancer in the subject.

It is another object of the invention to provide a method of monitoring the efficacy of a cancer therapy, wherein the cancer comprises cells that express or overexpress a tumor-associated antigenic epitope specifically bound by at least one of the NEO-102, NEO-201 or NEO-301 antibodies or a fragment thereof, comprising contacting a subject receiving said therapy with an antibody or antibody fragment that specifically binds a tumor-associated antigenic epitope specifically bound by at least one of the NEO-101, NEO-201 or NEO-301 antibodies and determining the amount of antigen expression in said subject wherein a decrease in antigen expression indicates that said therapy is effective at treating cancer in said subject.

In this application is described the use of NEO-102, NEO-201 and NEO-301 in flow cytometry experiments in order to identify additional human cancer cell lines that express the target antigen bound by these respective antibodies. These results confirm the utility of these antibodies in naked or conjugated form for treating and detecting different human cancers which correspond to these specific cell lines. It is anticipated that these studies will confirm that these antibodies may be used to treat or detect all stages of cancer wherein the cancer cell or precancerous cells express these antigens, e.g. pre-cancer and Stage I, II, II and IV cancers including metastatic cancers that express these target antigens.

Representative cancer cell lines and different human cancers that potentially may be evaluated for treatment or detection using the subject antibodies are set forth in comprised in Table 2 and FIG. 1. These cancers include by way of example colon, pancreatic, lung, prostate, melanoma, breast, melanoma, ovarian, uterine, and cervical cancers, and mesothelioma.

In addition, the present invention includes the production of radiolabeled forms of each of these antibodies and the use of the resultant radioimmunoconjugates in biodistribution studies effected animal models (e.g., in mice with human tumor xenografts) as well as human patients, in order to detect cancer cells that express a target antigen bound by NEO-102, NEO-201 and/or NEO-301. In the exemplary described embodiment the radio label used is indium-III, however, other radiolabels may alternatively be used including those described in PCT/US2011/041502, by Bristol et al, incorporated by reference herein.

These studies corroborate that NEO-102, NEO-201 and NEO-301, in labeled and unlabeled form, have broad application in the detection and treatment of different types of human cancer and should be substantially non-toxic to non-target normal tissues and organs. Said cancers include without limitation thereto breast, ovarian, cervical, or uterine cancer.

Diagnostic Methods

The NPC-1, 16C3, and A33 antigens, antibody which selectively bind the NPC-1, 16C3, or A33 antigen, and antigen-binding fragments thereof may be used in diagnostic methods for detecting the presence or absence of an NPC-1, 16C3, or A33 antigen. The NPC-1, 16C3, and A33 antigens, antibody which selectively bind the NPC-1, 16C3, or A33 antigen, and antigen-binding fragments thereof, A33 antigen may be used in methods comprising (a) contacting a test sample with an antibody, or fragment thereof, that binds a NPC-1 epitope, 16C3 epitope, and/or A33 antigen, and (b) assaying for antibody-epitope complexes, wherein the presence of said epitope is indicative of a carcinoma. Further, the NPC-1, 16C3, and A33 antigens, antibody which selectively bind a NPC-1, 16C3, or A33 antigen, and antigen-binding fragments, may be used in a method for detecting the presence of a NPC-1 epitope, 16C3 epitope, and/or A33 antigen in a patient comprising (a) administering to said patient a labeled monoclonal antibody, or fragment thereof, that binds a NPC-1 epitope, 16C3 epitope, and/or A33 antigen and (b) detecting the presence of a NPC-1 epitope, 16C3 epitope, and/or A33 antigen; wherein the presence of said epitope is indicative of a carcinoma. The antibody-epitope complex may be detected by Western blot, radio-immunoassay, ELISA (enzyme linked immunosorbent assay), "sandwich" immunoassay, immunoprecipitation assay, precipitation reaction, gel diffusion precipitation reaction, immunodiffusion assay, agglutination assay, complement-fixation assay, immunohistochemical assay, fluorescent immunoassay, and protein A immunoassay. The sample may be sample is a tissue biopsy, lymph, urine, cerebrospinal fluid, amniotic fluid, inflammatory exudate, blood, serum, stool, or liquid collected from the colorectal tract.

The NPC-1, 16C3, and A33 antigens, antibody which selectively bind a NPC-1, 16C3, or A33 antigen, and antigen-binding fragments thereof may be used in diagnostic methods for detecting the presence or absence of an NPC-1, 16C3, or A33 antigen, wherein the presence of the antigen is indicative of cancer including but not limited to lung, breast, ovarian, cervical, uterine cancer, pancreas, esophageal, colorectal, or liver cancer. The diagnostic methods may be used with patients at risk of cancer or patients without symptoms.

The antibodies which selectively bind a NPC-1, 16C3, or A33 antigen may be recombinant. The fragments of antibodies which selectively bind a NPC-1, 16C3, or A33 antigen may be a Fab, Fab', F(ab')2, Fv, CDR, paratope, or portion of an antibody that is capable of binding the antigen. The antibodies which selectively bind a NPC-1, 16C3, or A33 antigen may be chimeric, humanized, anti-idiotypic, single-chain, bifunctional, or co-specific. The antibodies which selectively bind a NPC-1, 16C3, or A33 antigen may be or fragment is conjugated to a label, including but not limited to a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label.

Additionally, NPC-1, 16C3, and A33 antigens, antibody which selectively bind a NPC-1, 16C3, or A33 antigen, and antigen-binding fragments thereof, may be attached to a solid support (e.g., bead, test tube, sheet, culture dish, or test strip) such as an array.

The method may detect colorectal polyps. The method may further comprise additional testing for the presence of tumors including but not limited to benign tumors, malignant tumors, metastatic tumors, and non-metastatic tumors. For example, the diagnostic method may detect pre-cancerous cells that express a cell marker comprising a NPC-1 epitope, 16C3 epitope, and/or A33 antigen.

The method may comprise imaging a NPC-1 epitope, 16C3 epitope, and/or A33 antigen by positron emission tomography (PET), CCD low-light monitoring system, x-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

The invention also provides a method for genetic diagnosis of a risk for cancer comprising taking a nucleic acid sample from a patient, analyzing said nucleic acid comprising comparing to cancer specific MUC5AC, CEACAM5, CEACAM6, or A33 sequence, wherein if the patient's nucleic acid sample matches the cancer specific MUC5AC, CEACAM5, CEACAM6, or A33 sequence, the patient is at risk for developing cancer.

The NPC-1, 16C3, and A33 antigens may be used as a cancer biomarker. Detection of the NPC-1, 16C3, or A33 antigens in a biological sample, such as a subject's serum, biopsied neoplastic cells or fecal sample, may be performed by means of the anti-NPC-1, anti-16C3, or anti-A33 antigen antibody. For example, a biological sample (e.g., a tumor, serum or fecal sample) is obtained from a subject, then NPC-1, 16C3, or A33 antigen is measured (e.g., by ELISA or PCR), and compared with corresponding samples from normal subjects. Measuring methods include any method of nucleic acid detection, for example in situ hybridization using antisense NPC-1, 16C3, or A33 antigen DNA or cRNA oligonucleotide probes, ultra-high throughput sequencing, nanostring technology, microarrays, rolling circle amplification, proximity-mediated ligation, PCR, qRT-PCR ChIP, ChIP-qPCR, or NPC-1, 16C3, or A33 antigen-binding antibodies. Comparatively high levels of NPC-1, 16C3, and A33 antigens indicate the presence and/or severity of pancreas or colon cancer, and may indicate metastasis or poor cancer prognosis.

The NPC-1, 16C3, and A33 antigens, antibody which selectively bind a NPC-1, 16C3, or A33 antigen, and antigen-binding fragments thereof, may be used in SQUID (Superconducting Quantum Interference Device) techniques for diagnostic methods. The SQUID technique comprises attaching nanoparticles of iron oxide to antibodies, which are then injected into the patient. If a tumor is present, the antibodies with conjugated nanoparticles recognize and bind to the NPC-1, 16C3, or A33 antigen on tumor cells. See, e.g., Hao, et al. (2010) Journal of Physics 43: 474004. In a SQUID method, the patient is then surrounded with sensitive magnetic coils in a superconducting quantum interference device (SQUID). A magnetic field is generated and all of the metal nanoparticles align in one direction. When the magnetic field is broken, the nanoparticles emit an electromagnetic signal as they relax back into their original state. By measuring the strength of the signal, on emay tell how many metal particles, and therefore how many tumor cells, may be present, and where in the patient the tumor cells are located. See, e.g., Shao, et al. (2010) Beilstein Journal of Nanotechnology 1: 142-154.

Samples and Procurement of Samples

The samples used in the methods described herein may be taken from a subject (patient) include but are not limited to a body fluid or secretion including but not limited to blood, serum, urine, plasma, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, secretions of the breast ductal system (and/or lavage thereof), broncho alveolar lavage, lavage of the reproductive system and lavage of any other part of the body or system in the body; samples of any organ including isolated cell(s) or tissue(s), wherein the cell or tissue can be obtained from an organ selected from, but not limited to lung, colon, ovarian, uterine, cervical, and/or breast tissue; stool or a tissue sample, or any combination thereof. In some embodiments, the term encompasses samples of in vivo cell culture constituents. Prior to be subjected to the diagnostic assay, the sample can optionally be diluted with a suitable diluent.

Numerous well known tissue or fluid collection methods can be utilized to collect the biological sample from the subject in order to determine the level of DNA, RNA and/or polypeptide of the marker of interest in the subject. Examples of tissue or fluid collection methods include, but are not limited to, fine needle biopsy, needle biopsy, core needle biopsy and surgical biopsy (e.g., brain biopsy), and lavage. Regardless of the procedure employed, once a biopsy/sample is obtained the level of the marker may be determined and a diagnosis can thus be made.

Detection of NPC-1, 16C3, A33 Antigens

The invention also provides a method for detecting the NPC-1, 16C3, and A33 antigens of this invention in a biological sample, comprising: contacting a biological sample with an antibody specifically recognizing a NPC-1, 16C3, or A33 antigen according to the present invention and detecting said interaction; wherein the presence of an interaction correlates with the presence of a NPC-1, 16C3, or A33 antigen in the biological sample.

The NPC-1, 16C3, and A33 antigens described herein are non-limiting examples of markers for diagnosing a disease and/or an indicative condition. Each marker of the present invention may be used alone or in combination, for various uses, including but not limited to, prognosis, prediction, screening, early diagnosis, determination of progression, therapy selection and treatment monitoring of a cancer (e.g., breast, ovarian, cervical, or uterine cancer).

The cancers that may be detected using the methods described herein include but are not limited to non-solid and solid tumors, cancer of the breast, prostate, lung, ovary, colon, uterus, stomach, cervix, liver, pancreas, and wherein the cancer may be invasive or metastatic.

Each NPC-1, 16C3, and A33 antigens of the present invention may be used alone or in combination, for various uses, including but not limited to, prognosis, prediction, screening, early diagnosis, determination of progression, therapy selection and treatment monitoring of cancers such as non-solid and solid tumors, cancer of the breast, prostate, lung, ovary, colon, uterus, stomach, cervix, liver, pancreas, and wherein the cancer may be invasive or metastatic. Such a combination may optionally comprise any subcombination of markers, and/or a combination featuring at least one other marker, for example a known marker. Furthermore, such a combination may optionally and preferably be used as described above with regard to determining a ratio between a quantitative or semi-quantitative measurement of any marker described herein to any other marker described herein, and/or any other known marker, and/or any other marker.

Markers of the present invention may optionally be used alone or in combination with known markers for lung cancer, including but not limited to CEA, CA15-3, beta-2-microglobulin, CA19-9, TPA, and/or in combination with the known proteins for the variant marker as described herein.

Markers of the present invention might optionally be used alone or in combination with known markers for ovarian cancer, including but not limited to CEA, CA125 (Mucin 16), CA72-4TAG, CA-50, CA 54-61, CA-195 and CA 19-9 in combination with CA-125, and/or in combination with the known proteins for the variant marker as described herein.

Markers of the present invention might optionally be used alone or in combination with known markers for colon cancer, including but not limited to CEA, CA19-9, CA50, and/or in combination with the known proteins for the variant marker as described herein.

Typically the level of the marker in a biological sample obtained from the subject is different (i.e., increased or decreased) from the level of the same marker in a similar sample obtained from a healthy individual (examples of biological samples are described herein).

Determining the level of the same marker in normal tissues of the same origin may be effected along-side to detect an elevated expression and/or amplification and/or a decreased expression, of the marker as opposed to the normal tissues.

The present invention also provides methods, uses, devices and assays for the diagnosis of cancers such as non-solid and solid tumors, cancer of the breast, prostate, lung, ovary, colon, uterus, stomach, cervix, liver, pancreas, and wherein the cancer may be invasive or metastatic. Optionally a plurality of markers may be used with the present invention. The plurality of markers may optionally include a markers described herein, and/or one or more known markers. The plurality of markers is preferably then correlated with the disease or condition. For example, such correlation may optionally comprise determining the concentration of each of the plurality of markers, and individually comparing each marker concentration to a threshold level. Optionally, if the marker concentration is above or below the threshold level (depending upon the marker and/or the diagnostic test being performed), the marker concentration correlates with the disease or condition. Optionally and preferably, a plurality of marker concentrations correlates with the disease or condition.

Alternatively, such correlating may optionally comprise determining the concentration of each of the plurality of markers, calculating a single index value based on the concentration of each of the plurality of markers, and comparing the index value to a threshold level. Also, such correlating may optionally comprise determining a temporal change in at least one of the markers, and wherein the temporal change is used in the correlating step.

Such correlating may optionally comprise determining whether at least "X" number of the plurality of markers has a concentration outside of a predetermined range and/or above or below a threshold (as described above). The value of "X" may optionally be one marker, a plurality of markers or all of the markers; alternatively or additionally, rather than including any marker in the count for "X", one or more specific markers of the plurality of markers may optionally be required to correlate with the disease or condition (according to a range and/or threshold).

Correlating may optionally comprise determining whether a ratio of marker concentrations for two markers is outside a range and/or above or below a threshold. Optionally, if the ratio is above or below the threshold level and/or outside a range, the ratio correlates with the disease or condition. Optionally, a combination of two or more these correlations may be used with a single panel and/or for correlating between a plurality of panels. Optionally, the method distinguishes a disease or condition with a sensitivity of at least 70% at a specificity of at least 85% when compared to normal subjects. As used herein, sensitivity relates to the number of positive (diseased) samples detected out of the total number of positive samples present; specificity relates to the number of true negative (non-diseased) samples detected out of the total number of negative samples present. Preferably, the method distinguishes a disease or condition with a sensitivity of at least 80% at a specificity of at least 90% when compared to normal subjects. More preferably, the method distinguishes a disease or condition with a sensitivity of at least 90% at a specificity of at least 90% when compared to normal subjects. Also more preferably, the method distinguishes a disease or condition with a sensitivity of at least 70% at a specificity of at least 85% when compared to subjects exhibiting symptoms that mimic disease or condition symptoms.

A marker panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers is outside of a normal range, this subset may be indicative of a particular diagnosis/prognosis. The skilled artisan will also understand that diagnostic markers, differential diagnostic markers, prognostic markers, time of onset markers, disease or condition differentiating markers, may be combined in a single assay or device. Markers may also be commonly used for multiple purposes by, for example, applying a different threshold or a different weighting factor to the marker for the different purpose(s).

The panels may comprise markers for the following purposes: diagnosis of a disease; diagnosis of disease and indication if the disease is in an acute phase and/or if an acute attack of the disease has occurred; diagnosis of disease and indication if the disease is in a non-acute phase and/or if a non-acute attack of the disease has occurred; indication whether a combination of acute and non-acute phases or attacks has occurred; diagnosis of a disease and prognosis of a subsequent adverse outcome; diagnosis of a disease and prognosis of a subsequent acute or non-acute phase or attack; disease progression (for example for cancer, such progression may include for example occurrence or recurrence of metastasis).

The above diagnoses may also optionally include differential diagnosis of the disease to distinguish it from other diseases, including those cancers such as non-solid and solid tumors, cancer of the breast, prostate, lung, ovary, colon, uterus, stomach, cervix, liver, pancreas, and wherein the cancer may be invasive or metastatic that may feature one or more similar or identical symptoms.

One or more diagnostic or prognostic indicators are correlated to a condition or disease by merely the presence or absence of the indicator(s). In other embodiments, threshold level(s) of a diagnostic or prognostic indicator(s) can be established, and the level of the indicator(s) in a patient sample can simply be compared to the threshold level(s). The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations, and/or by comparison of results from a subject before, during and/or after treatment.

NPC-1, 16C3, or A33 antigens may be featured as a biomarker for detecting cancers such as non-solid and solid tumors, cancer of the breast, prostate, lung, ovary, colon, uterus, stomach, cervix, liver, pancreas, and wherein the cancer may be invasive or metastatic.

The present invention optionally and preferably encompasses any amino acid sequence or fragment thereof encoded by a nucleic acid sequence corresponding to NPC-1, 16C3, or A33 antigens as described herein. Any oligopeptide or peptide relating to such an amino acid sequence or fragment thereof may optionally also (additionally or alternatively) be used as a biomarker.

The present invention provides a method for detecting a polynucleotide of this invention in a biological sample, using NAT based assays, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of the polynucleotide in the biological sample. Non-limiting examples of methods or assays are described herein. The present invention also relates to kits based upon such diagnostic methods or assays.

Additionally, the NPC-1, 16C3, and A33 antigens may be used as specific biomarkers for pancreas and colon cancer, and can be measured in biopsied tissue as well as in subject serum and fecal samples, as described herein. Additionally, diagnostic procedures used to detect colorectal cancer including but not limited to fecal occult blood test (FOBT), colonoscopy, computed tomographic colonography (virtual colonoscopy) [detects colorectal lesions larger than 6 mm in diameter with the same sensitivity as colonoscopy], flexible sigmoidoscopy, double-contrast barium enema, and digital rectal examination. Winawer, et al. (1997) Am J. Gastoenterology 112: 594-642; Blum (1995) Eur. J. Canc. 31: 1369-72; Ransohoff & Sandler (2002) N. Engl. J. Med. 346: 34611; Bruzzi (2002) N. Engl. J. Med. 346: 1672-74; and Laghi, et al. (2002) Am. J. Surg. 183: 124-31.

Immunoassays

The NPC-1, 16C3, or A33 antigens, antibodies and antigen-binding fragments that bind the NPC-1, 16C3, or A33 antigen, may be used in immunoassays to qualitatively or quantitatively detect and analyze markers in a sample. This method comprises providing an antibody specifically binds to a NPC-1, 16C3, and/or A33 antigen; contacting a sample with the antibody; and detecting the presence of a complex of the antibody bound to the marker in the sample.

An NPC-1, 16C3, and/or A33 antigen may be detected and/or quantified using any of a number of well recognized immunological binding assays. Useful assays include, for example, an enzyme immune assay (EIA) such as enzyme-linked immunosorbent assay (ELISA), a radioimmunoassay (RIA), a Western blot assay, or a slot blot assay. See, e.g., U.S. Pat. Nos. 4,366,241; 4,376,110; 4,517,288; and 4,837,168. Generally, a sample obtained from a subject can be contacted with the antibody specifically binds the NPC-1, 16C3, and/or A33 antigen.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies may be attached to a solid support.

After incubating the sample with antibodies, the mixture is washed and the antibody-marker complex formed may be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations. Usually the assays will be carried out at ambient temperature, although they can be conducted over a range of temperatures (e.g., 10 degrees C.-40 degrees C.).

The immunoassay can be used to determine a test amount of a marker in a sample from a subject. First, a test amount of a marker in a sample may be detected using the immunoassay methods described above. If a marker is present in the sample, it will form an antibody-marker complex with an antibody specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal. Several immunoassays are known in the art and the NPC-1, 16C3, and/or A33 antigens, and antibodies specific for said antigens described herein may used in such immunoassays including but not limited to radio-immunoassay (RIA), enzyme linked immunosorbent assay (ELISA), magnetic immunoassay, immunoblot, Western blot, immunoprecipitation assays, immunohistochemical analysis, and fluorescence activated cell sorting (FACS). See Wild, (2008) [Ed.] The Immunoassay Handbook [3rd Ed.] Elsevier.

Radio-Imaging Methods

The NPC-1, 16C3, or A33 antigens, antibodies and antigen-binding fragments that bind the NPC-1, 16C3, or A33 antigen, may be used in radio-imaging methods to diagnosis cancer including pancreatic and colorectal cancer, or monitor the progression of tumors. These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. SPECT may optionally be used with two labels simultaneously. See U.S. Pat. No. 6,696,686.

DEFINITIONS

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting.

As used in the description herein and throughout the claims that follow, the meaning of "a," "an," and "the" includes plural reference unless the context clearly dictates otherwise.

"Adjuvant," as used herein, refers broadly to any substance which is incorporated into or administered simultaneously with NPC-1 epitope peptidomimetic of the invention which potentiates the immune response in the subject. Adjuvants include but are not limited to aluminum compounds, e.g., gels, aluminum hydroxide and aluminum phosphate, and Freund's complete or incomplete adjuvant (e.g., in which the PS/A antigen is incorporated in the aqueous phase of a stabilized water in paraffin oil emulsion). The paraffin oil may be replaced with different types of oils, e.g., squalene or peanut oil. Other materials with adjuvant properties, include BCG (attenuated *Mycobacterium tuberculosis*), calcium phosphate, levamisole, isoprinosine, polyanions (e.g., poly A:U), lentinan, pertussis toxin, lipid A, saponins, QS-21 and peptides, e.g. muramyl dipeptide. Rare earth salts, e.g., lanthanum and cerium, may also be used as adjuvants. The amount of adjuvants depends on the subject and the particular antigen used and can be readily determined by one skilled in the art without undue experimentation.

"Amino acid," as used herein, refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Antibody," as used herein, refers broadly to any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, from all sources, e.g., human, rodent, rabbit, cow, sheep, pig, dog, chicken, are considered to be "antibodies." Antibodies include but are not limited to chimeric antibodies, human antibodies and other non-human mammalian antibodies, humanized antibodies, single chain antibodies (scFvs), camelbodies, nanobodies, IgNAR (single-chain antibodies derived from sharks), small-modular immunopharmaceuticals (SMIPs), and antibody fragments (e.g., Fabs, Fab', F(ab')$_2$.) Numerous antibody coding sequences have been described; and others may be raised by methods well-known in the art. See Streltsov, et al. (2005) Protein Sci. 14(11): 2901-9; Greenberg, et al. (1995) Nature 374(6518): 168-173; Nuttall, et al. (2001) Mol Immunol. 38(4): 313-26; Hamers-Casterman, et al. (193) Nature 363(6428): 446-8; Gill, et al. (2006) Curr Opin Biotechnol. 17(6): 653-8.

The term "antibody" is used in the broadest sense and specifically covers, for example, single monoclonal antibodies (including agonist, antagonist, and neutralizing antibodies), antibody compositions with polyepitopic specificity, polyclonal antibodies, single chain antibodies, and fragments of antibodies as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the alpha and gamma chains and four CH domains for mu and epsilon isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha, delta, epsilon, gamma, and mu, respectively. The gamma and alpha classes are further divided into subclasses on the basis of relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1E10^{-7}$ M, preferably no more than about $1E10^{-8}$ and most preferably no more than about $1E10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

Additionally, when referring to a modified Fc domain or "Fc variant", the terms "Kabat numbering system," "Kabat position," "Kabat residue," "Kabat number" or the like, or in any instance in which an Fc modification is identified by number without reference to a specific numbering system (e.g., "position" followed by a number), refer to positions numbered according to the EU index or EU numbering scheme (Kabat et al., 1991, Sequences of Proteins of Immunological Interest, 5th Ed., United States Public Health Service, National Institutes of Health, Bethesda, incorporated by reference). The terms "EU index" or "EU index as in Kabat" and the like refer to the numbering of the EU antibody (Edelman et al., 1969, Proc Natl Acad Sci USA 63:78-85, incorporated by reference). Additionally, except where stated otherwise, when referring to an Fc variant relative terms (such as "increased" or "decreased") refer to the change in that attribute relative to the same Fc variant (or polypeptide containing said Fc variant) without said modification.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation. Exemplary antibodies of the present disclosure may include one or more modifications that decrease one or more effector functions, such as alterations in the amino acid sequence, or alterations in the location, extent, or type of glycosylation.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed.

Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express Fc gamma RIII only, whereas monocytes express Fc gamma RI, Fc gamma RII and Fc gamma RIII. FcR expression on hematopoietic cells is summarized in Table 3 on page 464 of Ravetch and Kinet, Annu Rev. Immunol. 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. Antigens may be tumor specific (e.g., expressed by neoplastic cells of pancreatic and colon carcinoma.)

"Antigenic composition," as used herein, refers broadly to a composition that elicits an immune response.

"Cancer," as used herein, refers broadly to any neoplastic disease (whether invasive or metastatic) characterized by abnormal and uncontrolled cell division causing malignant growth or tumor.

"Chimeric antibody," as used herein, refers broadly to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug; or the variable region, or a portion thereof, is altered, replaced or exchanged with a variable region having a different or altered antigen specificity.

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) "Sequences of Proteins of Immunological Interest" National Institutes of Health, Bethesda, Md. These expressions include the hypervariable regions as defined by Kabat, et al (1991) "Sequences of Proteins of Immunological Interest" U.S. Dept. of Health and Human Services, or the hypervariable loops in 3-dimensional structures of antibodies. Chothia and Lesk (1987) J Mol. Biol. 196: 901-17. The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction. Kashmiri (2005) Methods 36: 25-34.

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/ml) or a relative amount (e.g., relative intensity of signals).

"Differentially present," as used herein, refers broadly to differences in the quantity or quality of a marker present in a sample taken from patients having a disease or condition as compared to a comparable sample taken from patients who do not have one of the diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker may be considered to be differentially present. Optionally, a relatively low amount of up-regulation may serve as the marker.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," as used herein, refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

An "effective amount" of a composition such as a polypeptide, drug, siRNA or analog thereof, antibody, pharmaceutical, small molecule, or other compound, or an agonist or antagonist thereof, is an amount sufficient to carry out a specifically stated purpose. An "effective amount" may be determined empirically and in a routine manner, in relation to the stated purpose.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Framework region" or "FR," as used herein, refers broadly to one or more of the framework regions within the variable regions of the light and heavy chains of an antibody. See Kabat, et al (1987) "Sequences of Proteins of Immunological Interest," National Institutes of Health, Bethesda, Md. These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"High affinity," as used herein, refers broadly to an antibody having a dissociation constant of about or less than $10^{-8}$ M, more preferably about or less than $10^{-9}$ M and even more preferably about or less than $10^{-10}$ M for a target antigen. However, "high affinity" binding can vary for other antibody isotypes. For example, "high affinity" binding for an IgM isotype refers to an antibody having a dissociation constant of about or less than $10^{-7}$ M and even more preferably about or less than $10^{-8}$ M for a target antigen.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

"Host cell," as used herein, refers broadly to a cell that contains an expression vector and supports the replication or expression of the expression vector. Host cells may be prokaryotic cells such as E. coli, or eukaryotic cells such as yeast, insect (e.g., SF9), amphibian, or mammalian cells such as CHO, HeLa, HEK-293, e.g., cultured cells, explants, and cells in vitro.

"Hybridization," as used herein, refers broadly to the physical interaction of complementary (including partially complementary) polynucleotide strands by the formation of hydrogen bonds between complementary nucleotides when the strands are arranged antiparallel to each other.

Administration "in combination with" one or more further therapeutic agents includes simultaNEOus (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

"K-assoc" or "Ka", as used herein, refers broadly to the association rate of a particular antibody-antigen interaction, whereas the term "Kdiss" or "Kd," as used herein, refers to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Isolated," as used herein, refers broadly to material removed from its original environment in which it naturally occurs, and thus is altered by the hand of man from its natural environment. Isolated material may be, for example, exogenous nucleic acid included in a vector system, exogenous nucleic acid contained within a host cell, or any material which has been removed from its original environment and thus altered by the hand of man (e.g., "isolated antibody").

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al. (2002) Short Protocols in Molecular Biology (5$^{th}$ Ed.) John Wiley & Sons, NY. Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, gerbils, goats, gorillas, hamsters, horses, humans, lemurs, llamas, mice, non-human primates, pigs, rats, sheep, shrews, squirrels, and tapirs. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C.

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. Antigens (Chapter 3) Immunology (5$^{th}$Ed.) New York: W.H. Freeman and Company, pages 57-75.

"Patient," as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient".

"Peptidomimetic," as used herein refers broadly to a compound that can imitate or block the biological effect of a peptide on a molecular level. Peptidomimetics may be polymers designed to mimic a peptide, such as peptoids and β-peptides, or may be a peptide that mimics a different peptide.

"Polypeptide," "peptide" and "protein," are used interchangeably and refer broadly to a polymer of amino acid residues. The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide" "peptide" and "protein" include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeNEOus population of proteins and other biologies. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. See, e.g., Turner, et al. (187) CSH Syrnp. Quant. Biol. LII: 123-33; Frier, et al (1986) PNAS 83: 9373-77; Turner, et al. (1987) J. Am. Chem. Soc. 109: 3783-85. A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence. "Substantial complementarity" refers to polynucleotide strands exhibiting about at least 90% complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," "substrate," or "solid phase" as used herein, refer to a non-aqueous matrix to which an antibody or other molecule of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149. The definition broadly includes any material that provides a solid or semi-solid structure with which another material can be attached including but not limited to smooth supports (e.g., metal, glass, plastic, silicon, and ceramic surfaces) as well as textured and porous materials.

"Subjects" as used herein, refers broadly to anyone suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g., rats and mice), lagomorphs, primates, and humans. Any mammalian subject in need of being treated according to the present invention is suitable. Human subjects of both genders and at any stage of development (i.e., NEOnate, infant, juvenile, adolescent, adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "patients."

"Symptoms" of disease as used herein, refers broadly to any morbid phenomenon or departure from the normal in structure, function, or sensation, experienced by the patient and indicative of disease.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a cancer if, after receiving a therapeutic amount of an antibody (or other drug), the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the antibody may prevent growth and/or kill existing cancer cells, it may be cytostatic and/or cytotoxic. Reduction of these signs or symptoms may also be felt by the patient.

The term "therapeutically effective amount" refers to an amount of an antibody, polypeptide, or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The term "synergistic effect" refers to the result achieved using a combination being greater than the sum of the results that would be achieved using the individual components of the combination. For example, in the context of a treatment method (e.g., treatment of cancer), a synergistic effect indicates that the effect of two or more treatments in combination (e.g., two or more of administration of an antibody, a chemotherapeutic agent, another anti-cancer agent, surgery, or radiation) have an effect that is more than just the additive effect of the individual agents. In an exemplary embodiment, the synergistic effect can be measured with respect to tumor burden, mean survival, or another endpoint as known in the art. For example, without intent to be limited by theory, one treatment (such as radiation or chemotherapy, e.g., gemcitabine) may induced increased expression of a cancer-associated antigen, such as the NPC-1, 16C3, or 31.1 antigen, thereby making the cancer cell more susceptible to antibody binding and/or effector function.

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a plasmid, cosmid, phagemid, phage DNA, or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be inserted in order to bring about its replication and cloning. The vector may further contain a marker suitable for use in the identification of cells transformed with the vector.

In order that the invention herein described may be fully understood, the above detailed description is set forth. Various embodiments of the invention are described in detail and may be further illustrated by the provided examples. The examples provided are intended to be illustrative, rather than limiting, on the scope of the invention, which is limited only by the scope of the claims provided below.

EXAMPLES

Example 1

This example reports the level of NEO-101 or NEO-102, NEO-201 and NEO-301 Antigen Expression by Human Normal and Cancer Cell Lines. The results indicate that multiple independent samples of different cancers expressed the antigens recognized by NEO-101 or NEO-102, NEO-201 and/or NEO-301.

Antigen expression in cell lines of various origins were detected by Flow Cytometry. Viable cell suspensions were incubated with primary antibody NEO-101, NEO-201 and NEO-301 separately at 10 ug/mL. Human IgG (10 ug/mL) was used as negative control. Goat anti-human IgG (Fc)-phycoerythrin conjugate was used for primary antibody detection; 7-ADD was used for excluding dead cells from analysis. The staining was measured by Flow Cytometry (Guava instrument, Millipore). Median fluorescent intensity (MFI) and % of stained cells was used for determining presence of specific antigen on each cell line.

The results are summarized in FIG. 1. The cell lines tested included breast cancer cells, cervical squamous carcinoma cells, colorectal adenocarcinoma cells, lung adenocarcinoma cells, lung carcinoma cells, lung squamous carcinoma cells, myelogenous leukemia cells, ovarian cancer cells, pancreatic adenocarcinoma cells, pancreatic carcinoma cells, prostate adenocarcinoma cells, and prostate cancer cells. Additionally, normal lung cells were tested.

NEO-101 expression was detected in multiple colorectal adenocarcinoma and multiple pancreatic adenocarcinoma samples. NEO-201 expression was detected in multiple colorectal adenocarcinoma, multiple pancreatic adenocarcinoma, multiple lung adenocarcinoma, and multiple lung squamous cell carcinoma cell lines. NEO-301 expression was detected in colorectal adenocarcinoma and pancreatic adenocarcinoma cell lines.

Example 2

This example reports prevalence of NEO-101, NEO-201, and NEO-301 antigen expression in cancer cell samples obtained from cancer tissue microarrays and from paraffin tissue sections.

Immunohistochemistry (IHC) was used for determining the presence of NEO-101/102, NEO-201 and NEO-301 antigens on paraffin microarrays and tissues. These primary antibodies (NEO-101/NEO-102, NEO-201 and NEO-301) were biotinylated prior to use. Paraffin tissue microarrays and slides of tissues were reacted with the primary antibody after inactivating endogenous peroxidase and blocking the slides. Staining was detected with streptavidin-horseradish peroxidase conjugate and visualized with chromogen. Biotinylated human IgG1 was used as negative control and mouse anti-human cytokeratin monoclonal antibody was used as positive control. Antibody staining was measured as % and intensity of tumor epithelial cells and luminal secretion within the whole tissue section.

The cancer cells and normal cells tested were of the following tissue origins: Colon, Pancreas, Lung, Larynx, Prostate, Esophagus, Uterus, Stomach, Skin, Breast, and Ovary.

The results are summarized in tabular form in FIG. 2. For cancer tissue microarray samples, a high percentage of colon cancer samples were positive for all three antigens, with 61%, 85%, and 87% respectively, of the cancer samples being positive for NEO-101, NEO-201, and NEO-301. For pancreatic cancer a high percentage of cancer samples were positive for NEO-201 and NEO-301 at 86% and 57%, respectively, positive for the antigen; a lower but still appreciable fraction (31%) of pancreatic cancer cells were positive for NEO-101. For lung cancer a high percentage of cancer samples were positive for NEO-201 and NEO-301 at 61% and 56%, respectively. For esophagus cancer 43% of the cancer samples were positive for NEO-301, and for uterus cancer 41% of the cancer samples were positive for NEO-101 and 51% of cells were positive for NEO-201. For stomach cancer, 30% of samples were positive for NEO-101. For skin cancer, 16% of samples were positive for NEO-201. Finally, for breast cancer, 78% of samples were positive for NEO-301. Additionally, normal (non-cancerous) samples of each cell type were tested, with the percentages of positive samples as indicated which were generally low relative to the percentage of positive cancer cell samples in each instance.

For paraffin tissue sections, a high percentage of colon cancer samples were positive for all three antigens, with 87%, 94%, and 52% respectively, of the cancer samples being positive for NEO-101, NEO-201, and NEO-301. For pancreatic cancer a high percentage of cancer samples were positive for all three antigens, with 82%, 83%, and 47% respectively, of the cancer samples being positive for NEO-101, NEO-201, and NEO-301. For lung cancer a high percentage of samples were positive for NEO-101 and NEO-201 at 67% and 90%, respectively; relative to the other sample types relatively fewer lung cancer samples were tested which may account for some of the variation relative to the cancer tissue microarray results. Additionally, normal (non-cancerous) samples were tested as indicated, with the percentages of positive samples as indicated which were generally low relative to the percentage of positive cancer cell samples in each instance.

Finally, expression results for normal cell samples from paraffin tissue sections are summarized in FIG. 3 for both normal cell samples and normal samples adjacent to colon or pancreatic cancer.

Example 3

This example reports the use of NEO-101, NEO-201, and NEO-301 to localize cancer cells in vivo.

Antibodies NEO-101, NEO-201, and NEO-301 are radiolabeled by conjugation to either $^{111}$In or $^{86}$Y using the acyclic chelate CHX-A"-DTPA. The conjugation molar ratios are empirically determined. Human tumor xenografts are introduced into SCID or nude mice, including the cell lines identified in FIG. 1 as being reactive with NEO-101, NEO-201, or NEO-301 in cell culture and optionally further cancer cell lines detected to bind those antibodies. Control xenografts non-reactive with these antibodies are also utilized. Following intravenous administration of radiolabeled antibodies in tumor-bearing mice, cell samples are harvested and analyzed. Labeled antibody biodistribution is determined with respect to the tumor and other tissues including liver and kidneys.

Additionally, xenograft bearing mice are subjected to imaging studies including planar gamma-imaging performed at multiple time points to assess the stability of labeled antibody binding to the tumor cells and measure the level of accumulation of radiolabeled antibody in other tissues. The study results establish that expression of the NEO-101, NEO-201, and NEO-301 antigens by cancer cells occurs in vivo, and that these antibodies are able to bind their respective antigens and thereby permit cancer detection in an in vivo context.

Example 4

Different tumor models are assessed using radiolabeled antibodies according to the invention. These tumor models will comprise mice who contain human tumor cells originating from a human tumor cell line that expresses a target antigen bound by NEO-101, NEO-201 and/or NEO-301. Ideally these tumor models will correspond to different types of human cancers that express these antigens, e.g., colon, pancreatic, lung, prostate, melanoma, breast, melanoma, ovarian and mesothelioma. As the target antigens are known to be expressed by different cancers it is anticipated that human cancer cell lines tumor corresponding to these cancer types that express the subject target antigens may be identified by flow cytometry as described in Example 1.

In these experiments 4-6 week old male and female athymic mice (nu/nu) are subcutaneously injected in the flank or subscapular region with human cancer cell lines (about 2-6×106 cells) and tumors permitted to develop after injection. After the tumors have reached about 0.3-0.5 cm in diameter, these mice are injected with NEO-101, NEO-201 or NEO-301 antibody conjugates which are labeled with 111 In (prepared using standard labeling and purification methods). Approximately 5-7.5 micro Ci of the radiolabeled antibody is injected via the tail vein.

Mice (n=25) injected with the radiolabeled antibody are euthanized by CO2 inhalation at designated times, typically 24, 48, 72, 96 or 120 hours after injection. The blood, tumor and normal organs are harvested from the euthanized animals, wet weighed and the radioactivity measured in a gamma-scintillation counter. Radioactivity measurements (cpm's) are corrected for decay based on the day of injection and expressed as % ID/g of tissue. Tumor tissue ratios are calculated to determine the localization index for the RCs and blood tissue ratios are determined to assess the in vivo stability of the RCs.

In some instances a longer interval after injection, e.g., 14 days, is employed in order to better assess the residence time of the radiolabeled antibody in vivo. In such case additional mice are used in the studies.

The results of these experiments will confirm that different human tumors in vivo express the target antigens expressed by NEO-101, NEO-201 and NEO-301 in sufficient amounts to facilitate the use of these antibodies in labeled or unlabeled form to detect and treat different human cancers, e.g., colon, pancreatic, lung, prostate, melanoma, breast, melanoma, ovarian and mesothelioma. In addition, these experiments will confirm that the antibody is delivered to and localizes at the desired target sites (tumors) and not normal tissues.

In particular these experiments will corroborate that these antibodies specifically bind and accumulate in a time-dependent manner at tumor sites with little or no cross-reactivity with non-cancerous major organs and tissues such as the heart, spleen, kidney and liver. These results while obtained in a pre-clinical mouse model are anticipated to correlate to the binding properties of these antibodies in humans patients having a cancer which is characterized by expression of one or more of the target antigens bound by NEO-101, NEO-201 and NEO-301.

Based on these results the subject antibodies will be used to image tumors in vivo. These imaging methods provide for the early detection of cancers that express the antigens specifically bound by NEO-101, NEO-201 and NEO-301. In addition, these imaging methods are useful in cancer therapeutic regimens as these images may be used to stage the status of a cancer in a particular individual, and thereby design an appropriate therapeutic regimen using the subject antibodies alone or in association with other treatment regimens and therapeutic agents such as chemotherapy, radiation, immunoradiopharmaceuticals, other biologics and immune modulators and combinations thereof. The use of the subject antibodies as imaging agents may be used to establish disease prognosis based on the number and location of tumor cells that express the antigen bound by NEO-101, 201 or NEO-301 and further may be used to establish the efficacy of a particular treatment method based on its effect on the number and location of detected tumor cells and the level of tumor associated antigen expressed on these cells. Methods for using antibodies and antibody fragments to detect and image tumors in vivo are well established.

Example 5

This example describes the determination of the involvement of extrinsic and intrinsic apoptosis pathways in cancer cell death after cell treatment with anti-CAA antibodies including NEO-201, and experiments conducted in cultured cells and in animal and human subjects to measure efficacy of anti-CAA antibodies (such as NEO-201) alone or in combination with another anti-cancer agent or therapy.

In brief, cancer cells (including tissue samples and cultures established from primary cell samples as well as cell lines) are first tested for binding of the cancer-associated anti-CAA antibodies (NEO-201, NEO-102, or NEO-301). Binding of the antibody to the cells is determined by immunohistochemistry or FACS. Cancer cells tested include breast, ovarian, uterine, and cervical cancer cells and tissues. From these results it is confirmed that a subset of patient samples express the cancer-associated antigen and thus the patients from which they are derived would be expected to respond to treatment with the respective anti-CAA antibodies (such as NEO-201) that specifically bound to that sample.

Cancer cells to which the antibody bound are then tested for antibody-mediated cell death. Cells are contacted with the anti-CAA antibody (NEO-201, NEO-102, or NEO-301) in vitro. Antibody sequences are as indicated in Table 1, above, including antibody NEO-201 containing the variable heavy and light chain sequences shown in SEQ ID NOs. 95 and 100. Cells are treated with the antibody over a range of concentrations. Cell death, ATP levels, and expression of Caspases 3 and 8 are detected using the methods described below. Multiple measurements are performed for each condition to allow statistical comparison of results. From these results the activation of caspase 3 and/or caspase 8 during cell killing is detected by, indicating the involvement of the intrinsic and extrinsic pathways, respectively, in the cell killing mechanism.

Apoptosis pathway involvement is confirmed by RNAi knockdown of the caspase 3 and caspase 8 genes (individually in combination). Cells are treated with the anti-CAA antibody (NEO-201, NEO-102, or NEO-301) after RNAi knockdown of caspase-3 and/or 8. Mirroring the Caspase Glo® results, decreased apoptosis following knockdown of caspase is predicted to confirms involvement of the apoptotic pathway (i.e., extrinsic or intrinsic) in anti-CAA antibody-mediated cell death. Specifically, decreased cell death in the caspase-3 knockdown is indicative of extrinsic pathway involvement, while decreased cell death in caspase knockdown is indicative of intrinsic pathway involvement.

Cultured cancer cells are additionally treated with the anti-CAA antibody (NEO-201, NEO-102, or NEO-301) in combination with chemotherapeutic and radiation therapies in order to detect combinations that enhance cell killing. Chemotherapeutic agents that activate extrinsic or intrinsic apoptosis pathways are predicted to increase cell killing based on the involvement of the extrinsic or intrinsic pathway in cell killing, respectively, as determined by Caspase Glo® and RNAi knockdown experiments described above.

Experiments are performed to test the cell killing effects of extrinsic pathway activating chemotherapeutic agents tested in combination with the anti-CAA antibodies (NEO-201, NEO-102, or NEO-301). These extrinsic pathway-targeting agents include agents that target PML-RARα, DR4 (TRAIL R1), and/or DR5 (TRAIL R2). Specific agents targeting the extrinsic pathway to be tested include TRAIL (human TRAIL polypeptide or an agonistic fragment thereof), Dr4 agonists, Dr5 agonists, and all trans retinoic acid (ATRA).

Experiments are also performed to test the cell killing effects of intrinsic pathway activating chemotherapeutic agents tested in combination with the anti-CAA antibodies (NEO-201, NEO-102, or NEO-301). These intrinsic pathway-targeting agents include agents that target Bcl-1, Bcl-XL, Bax, BCL-Xs and/or PML-RARα. These include agents that act directly on the mitochondrial inner membrane, agents that antagonize the antiapoptotic members of the Bcl-2 protein family, and agents that enhance the activity of the proapoptotic members of the Bcl-2 family of proteins such as Bax. Specific agents targeting the intrinsic pathway include arsenic trioxide, lonidamine (a derivative of indazole-3-carboxylic acid), antisense agents targeting Bcl-1 (such as Genasense, G3139 or oblimersen sodium), antisense agents targeting Bcl-XL, Bax, and BCL-Xs. Additional antisense agents target both Bcl-2 and Bcl-XL, or target clusterin (also known as testosterone-repressed prostate message 2). The intrinsic pathway-targeting agents also include small molecules. One group of small molecules recognizes the surface pocket of Bcl-2 or Bcl-XL, including Antimycin-A and derivatives thereof, HA14-1, and synthetic BH3 organic peptides.

Additionally, from involvement of the extrinsic or intrinsic apoptotic pathway in cell killing, it is predicted that chemotherapeutic agents that activate the common pathway or otherwise promote or sensitize cells to apoptosis would also enhance cancer cell killing. This prediction is confirmed by detecting cell killing by anti-CAA antibodies (NEO-201, NEO-102, or NEO-301) in combination with a pro-apoptotic agent.

Direct cell killing is also detected by detecting cell death caused by treatment with anti-CAA antibodies (NEO-201, NEO-102, or NEO-301) in the absence of caspases 3 and 8 (i.e., cell death in the caspase 3 and caspase 8 combined RNAi knockdown). From cell killing activity in the absence of both caspases it is predicted that the anti-CAA antibody potentiates direct cell killing. From these results, it is predicted that chemotherapeutic agents that enhance direct cell killing can result in increased cell death in combination with the anti-CAA antibody. Direct cell killing agents tested in combination with the anti-CAA antibodies (NEO-201, NEO-102, or NEO-301) including mixed lineage kinase domain like (MLKL) protein, rapamycin (RAP) or derivatives and/or analogs thereof, such as everolimus or RAD001; CCI-779, ABT578, SAR543, ascomycin (an ethyl analog of FK506), AP23573, AP23841, KU-0063794, INK-128, EX2044, EX3855, EX7518, or compounds that bind to the ATP-binding cleft of mTOR, such as AZD08055 and OSIO27.

Cell killing by ADCC in the presence of the anti-CAA antibodies (NEO-201, NEO-102, or NEO-301) is also tested. In brief, cells are contacted with the antibody in the presence of effector cells (such as PBMCs) and cancer cell survival is measured.

Based thereon, cancer cell killing is tested in animal models. Cancer cells (including breast, ovarian, cervical, or uterine) are grown in a tumor xenograft model. The animals are treated with the same anti-CAA antibodies confirmed to kill the cells in vitro, and cells are selected that were killed by each anti-CAA antibody (including NEO-201). The efficacy of the anti-CAA antibody in the tumor xenograft model is determined alone. Combinations with anti-cancer agents that exhibited enhanced cell killing in vitro are tested in vivo to demonstrate enhanced therapeutic efficacy in this model.

Finally, human subjects are treated with the anti-CAA antibody (such as NEO-201). Patients are selected for treatment based upon detection of binding to and/or killing of patient cancer cell samples. Alternatively, patients are selected for treatment because similar patient cell samples have previously been shown to bind to and/or be killed by the anti-CAA antibody. For example, a patient may be selected for treatment where cells of the same cancer type (e.g., breast, ovarian, cervical, and/or uterine) and optionally the same stage of cancer progression have been previously shown to bind to and/or be killed by the anti-CAA antibody. Patients may be treated with the anti-CAA antibody alone, or in combination with another anti-cancer agent or therapy. The other anti-cancer agent or therapy may be selected based upon observed increases in therapeutic efficacy observed in the aforementioned animal studies, and/or based upon enhanced cell killing efficacy observed for the combination in vitro.

Methods for the foregoing experiments are provided in further detail below. Protocols and steps not otherwise described may be carried out by methods known in the art based upon the foregoing description.

Cell Death Assays

Cytotoxicity is measured by adding 20 µl of 3-(4,5-dimethylthiazol-2-yl)-2,5-diphenyltetrazolium bromide (MTT) (12 mm) to cells for 60 min. DMSO is added to solubilize the MTT formazan (reduced product) and measurements are taken at a wavelength of 570/620 nm. Apoptosis and necrosis are measured using a propidium iodide (PI) and allophycocyanin-conjugated Annexin V Apoptosis Detection kit (eBiosciences). Cells are collected using TrypLE™ (Invitrogen) and analyzed by flow cytometry on a BD FACSCalibur according to the manufacturer's protocol.

ATP Assay

Intracellular ATP levels are measured by a CellTiter-Glo luminescent cell viability assay (Promega G7571) according to the manufacturer's instructions and read on a Victor3 1420 multilabel automated plate reader (PerkinElmer Life Sciences).

Caspase Activity by Caspase-Glo® (Luciferase Assays)

A luciferase-based caspase assay is used to measure caspases-3/7 (Caspase-Glo® 3/7 Assay Systems, Promega) and caspase-8 (Caspase-Glo 8 Assay System, Promega) activity according to the manufacturer's protocol. Samples are read on a Victor3 1420 multilabel automated plate reader (PerkinElmer Life Sciences).

Real Time qPCR and RT-PCR

Total RNA is extracted using a GeneJET™ RNA Purification kit (Fermentas, Canada) and treated with DNase (Fermentas) to remove traces of genomic DNA. 1 µg of purified RNA is reverse transcribed using Moloney murine leukemia virus reverse transcriptase (Sigma) with random hexamer and oligo(dT) primers (Fermentas). cDNA is diluted accordingly, and 10-µl reactions are set up using Green-2-Go qPCR Mastermix to run qPCR. A CFX384 Touch™ Real-Time PCR Detection System (Bio-Rad) is used to obtain the raw threshold cycle (Ct) values. Results are analyzed using the 2-ΔCt formula normalizing target gene expression to housekeeping controls. For RT-PCR, 50-µl reactions are prepared using 25 ng of cDNA, and PCR is performed using Taq DNA polymerase (Fermentas). PCR products are resolved on a 2% agarose gel and stained for qualitative or quantitative analysis.

Immunohistochemistry

Cells are fixed and stained with primary antibody specific for cleaved caspase 3 or cleaved caspase 8. Samples are then incubated with biotinylated secondary antibody, followed by avidin-linked horseradish peroxidase (HRP) and staining.

ADCC Assay

PBMC effector cells are isolated from blood samples obtained by Ficoll-Hypaque density centrifugation. The target cells are incubated at $5 \times 10^6$ cells/mL in complete growth media with 15 µL of 0.1% calcein-AM solution (Sigma-Aldrich) for 30 minutes at 37° C., in the presence of 5% CO2. The cells are washed twice with 15 mL of PBS-0.02% EDTA and resuspended in 1 mL complete growth medium. Fifty microliters (10,000 cells) of labeled target cells are plated into a 96-well plate in the presence or absence of antibodies at the selected concentration, and incubated with 50 µL of freshly isolated peripheral blood mononuclear cells (effector cells, at 100:1 E/T ratio) accordingly. After 2 hours of incubation, the plate is centrifuged at 300×g for 10 minutes, and 75 µL of supernatant is transferred into a new flat-bottomed 96-well plate. The fluorescence in the supernatant is measured at 485-nm excitation and 535-nm emission. Spontaneous release is determined from target cells in RPMI-1640 medium with 30% FBS without effector cells and maximum release is determined from target cells in RPMI-1640 medium with 30% FBS and 6% Triton X-100 without effector cells.

Percent cytotoxicity is calculated as[(counts in sample−spontaneous release)/(maximum counts−spontaneous release)]×100.

Each document cited herein including all patents, patent applications, non-patent literature, and any other publications, is hereby incorporated by reference in its entirety.

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

Example 6

This example describes assays to determine cytotoxic effects of antibodies to cancer-associated antigens (including antibodies to NPC-1, 16C3, and 31-1 antigens such as NEO-102, NEO-102, NEO-103, NEO-201, NEO-301, and NEO-302) in a xenograft human cancer murine model, as a single agent and in combination with chemotherapy or radiation therapy.

Methods: The methods used are essentially as described in Buchsbaum et al., Clin Cancer Res. 2003 Sep. 1; 9(10 Pt 1):3731-41, which is hereby incorporated by reference in its entirety. In brief, the binding of the cancer-associated antigen antibody to a panel of human cancer cell lines is evaluated by indirect immunofluorescence and flow cytometry (also see Example 1). Cytotoxicity of the antibody alone and in the presence of an anti-cancer agent (gemcitabine or another agent) is measured in vitro. Antitumor efficacy is determined by treatment of nude mice bearing human cancer xenografts with the antibody alone or in combination with an anti-cancer agent, or in combination with radiation therapy. Tumor size and regression rates are determined. Optionally, expression of a cancer-associated antigen (such as the NPC-1, 16C3, or 31.1 antigen) may be measured to determine whether cancer-associated antigen expression is increased by an anti-cancer agent (gemcitabine or another agent) or radiation therapy, which without intent to be limited by theory would be predicted to increase antibody binding to cancer cells and/or increase susceptibility of cancer cells to depletion by the antibody. The results indicate that the antibodies alone or in combination with chemotherapy and/or radiation have antitumor efficacy in the cancer xenograft models, and synergistic benefits of the combination therapies are observed relative to treatment with the individual agents.

Each document cited herein, including all patent and non-patent literature, published or unpublished patent applications, abstracts, and any other document cited, is hereby incorporated by reference in its entirety.

Having fully described the invention, the following claims are now provided below.

What is claimed is:

1. A method of treatment, comprising administering to a subject in need thereof an effective amount of an antibody specific for a cancer-associated antigen ("anti-CAA antibody"), wherein said cancer-associated antigen is 16C3 and second therapeutic agent, wherein said anti-CAA antibody comprises a NEO-201 antibody comprising a light chain variable region containing the complementarity determining region (CDR) 1 of SEQ ID NO: 77 or 97, CDR2 of SEQ ID NO: 78 or 98, and CDR3 of SEQ ID NO: 79 or 99, and comprising a heavy chain variable region containing the CDR1 of SEQ ID NO: 82 or 102, CDR2 of SEQ ID NO: 83 or 103, and CDR3 of SEQ ID NO: 84 or 104, wherein said anti-CAA antibody and said second therapeutic agent are administered at a lower dosage than the effective dosage of said anti-CAA antibody or said second therapeutic agent when administered individually, wherein said method is for the treatment of a cancer that expresses an antigen specifically bound by said anti-CAA antibody.

2. The method of claim 1, wherein said second therapeutic agent comprises an anti-cancer agent.

3. The method of claim 1, wherein said second therapeutic agent targets the extrinsic apoptotic pathway.

4. The method of claim 1, wherein said second therapeutic agent targets the intrinsic apoptotic pathway.

5. The method of claim 1, wherein said second therapeutic agent targets the common apoptotic pathway.

6. The method of claim 1, wherein said second therapeutic agent enhances ADCC of cancer cells.

7. The method of claim 1, wherein the second therapeutic agent comprises gemcitabine, cisplatin, a death receptor (DR) agonist, DR ligand or fragment or variant thereof, TRAIL, a Fas ligand, TNF receptor 1 (TNFRI), TRAIL-R2, DR4, DR5, or CD95 (APO-1/Fas), an agent that agent activates a death receptor or sensitizes said death receptor to activation by another agent.

8. The method of claim 1, wherein said second agent comprises an extrinsic pathway agent that agonizes the extrinsic apoptotic pathway in cancer cells, an extrinsic pathway agent that targets PML-RARα, DR4 (TRAIL R1), DR5 (TRAIL R2), an extrinsic pathway agent that comprises TRAIL polypeptide or an agonistic fragment thereof, a Dr4 agonist, a Dr5 agonist, all trans retinoic acid (ATRA), a Dr4 or Dr5 agonist comprising an agonistic anti-Dr4 or anti-Dr5 monoclonal antibody, optionally selected from Apomab, HGS-ETR1, HGS-ETR2, and GS-TR2J, an extrinsic pathway agent comprising necrosis factor alpha (TNF-alpha), tumor necrosis factor beta (TNF-beta, lymphotoxin alpha), lymphotoxin beta (LT-beta), TRAIL (Apo2L), CD95 (Fas, APO-I) ligand, TRAMP (DR3, Apo-3) ligand, DR4 ligand, DR6 ligand or a fragment, variant, or derivative thereof, an extrinsic pathway agent comprising an anti-CD95 antibody, anti-TRAIL-R1 (DR4) antibody, anti-TRAIL-R2 (DR5) antibody, anti-DR6 antibody, anti TNF-R1/2 antibody and anti-TRAMP (DR3) antibody or a fragment or derivative thereof, an extrinsic pathway agent comprising a chemotherapeutic agent, mapatumumab (HGS-ETR1), lexatumumab (HGS-ETR2), conatumumab (AMG655), dulanermin (AMG 951, APO2L/TRAIL, PRO1762, RG3639, rhApo2L/TRAIL), tigatuzumab (CS1008), TRAIL R (DR4-Specific Altrimer, Anaphore), HGS TR2J, LBY135, drozitumab (PR085780, apomab), SL231, SM164 with TRAIL R2, or TAS266, an extrinsic pathway agent comprising doxorubicin, etoposide, cisplatin, bleomycin, 5-fluorouracil, mitomycin C, oxaliplatin, 2-deoxy-D-glucose, a platin, a drug that targets a Fas pathway or a c-FLIP pathway, 4-(4-Chloro-2-methylphenoxy)-N-hydroxybutanamide (CMH), estradiol (E2), or delta-tocotrienol.

9. The method of claim 1, wherein said second therapeutic agent comprises an intrinsic pathway agent that agonizes the intrinsic apoptotic pathway in cancer cells, an agonist of a proapoptotic Bcl-2 family member, an agonist of Bax, Bak, Bad, Bcl-Xs, Bid, Bik, Bim, or Hrk, an antagonist of an antiapoptotic Bcl-2 family member, an antagonist of Bcl-2, Bcl-XL, Bcl-W, Bfl-1, or Mcl-1, an agent that targets Bcl-1, Bcl-XL, Bax, BCL-Xs and/or PML-RARα, an agent that acts directly on the mitochondrial inner membrane, and agent that antagonizes the antiapoptotic members of the Bcl-2 protein family, or an agent that enhances the activity of the proapoptotic members of the Bcl-2 family of proteins such as Bax, arsenic trioxide, lonidamine an antisense agent targeting Bcl-1, Bcl-XL, Bax, BCL-Xs, both Bcl-2 and Bcl-XL, clusterin, or comprises oblimersen sodium, a small molecule, a small molecule that recognizes the surface pocket of Bcl-2 or Bcl-XL, Antimycin-A, HA14-1, synthetic BH3 organic peptides, or a derivative thereof, farnesylthiosalicylic acid (FTS), estradiol (E2), delta-tocotrienol, salinomycin, or curcumin, an antimetabolite, alkylator, corticosteroid, radiation, monoclonal antibody, platin or PARP inhibitor, epirubicin, cisplatin, dacarbazine, fludarabine/cyclophosphamide, dexamethasone, or doxorubicin, FTS, CMH, TMS, or estradiol (E2).

10. The method of claim 1, wherein said second therapeutic agent comprises a cytostatic agent, cytocidal agent, actinomycin D, adriamycin, arsenic trioxide, asparaginase, bleomycin, busulfan, camptosar, carboplatinum, carmustine, chlorambucil, cisplatin, corticosteroids, colicheamicin, cyclophosphamide, daunorubicin, docetaxel, doxorubicin, epirubicin, etoposide, fludarabine, fluorouracil, gemcitabina, gemcitabine, gemzar, hydroxyurea, idarubicin, ifosfamide, irinotecan, lomustine, melphalan, mercaptomurine, methotrexate, mitomycin, mitoxantrone, oxaliplatin, paclitaxel, platinol, platinex, procarbizine, raltitrexeel, rixin, steroids, streptozocin, taxol, taxotere, thioguanine, thiotepa, tomudex, topotecan, treosulfan, trihydrate, vinblastine, vincristine, vindesine, vinorelbina, vinorelbine, duanomycin, dactinomysin, esorubisin, mafosfamide, cytosine arabinoside, bis-chloroethylnitrosurea, mitomycin C, mithramycin, prednisone, hydroxyprogesterone, testosterone, tamoxifen, dacarbazine, hexamethylmelamine, pentamethylmelamine, amsacrine, chlorambudil, methylcyclohexylnitrosurea, nitrogen mustards, cyclophosphamide, 6-mercaptopurine, 6-thioguanine, cytarabine, 5-azacytidine, deoxyco-formycin, 4-hydroxyperoxycyclophosphoramide, 5-fluorouracil (5-FU), 5-fluorodeoxyuridine (5-FUdR), colchicine, trimetrexate, teni-poside, diethylstilbestrol, a DNA damaging agent, nucleophosmin, an agent which induces cellular damage as part of an enhanced or synergistic process with another agent, a catalytic antibody, prodrugs, CHK1/2 inhibitor, CBP-501, AZD7762, histone deacetylase inhibitor, vorinostat, tumour necrosis factor related apoptosis inducing ligand, BH3 mimetic, ABT737, small molecule inhibitors, tyrosine kinase inhibitors, imatinib mesylate, gefitinib, erlotinib, monoclonal antibodies, rituximab, trastuzumab, a caspase activator, apoptin, survivin, an endocrine therapeutic, a biologic response modifier, interferon, interleukin, antibody, aptamer, siRNA, oligonucletoide, enzyme, ion channel and receptor inhibitor or activator, hyperthermia, cryotherapy, agent to attenuate any adverse effects, or antiemetic, an alkylating drug, mechlorethamine, chlorambucil, Cyclophosphamide, Melphalan, Ifosfamide, antimetabolite, Methotrexate, purine antagonist, pyrimidine antagonist, 6-Mercaptopurine, 5-Fluorouracil, Cytarabile, Gemcitabine, spindle poison, Vinblastine, Vincristine, Vinorelbine, Paclitaxel, podophyllotoxin, Etoposide, Irinotecan, Topotecan, antibiotic, doxorubicin, Bleomycin, Mitomycin, nitrosoureas, Carmustine, Lomustine, inorganic ion, Cisplatin, Carboplatin, enzyme, Asparaginase, hormone, Tamoxifen, Leuprolide, Flutamide, Megestrol, an agent that targets p53, p53 pathway members, IκB kinase, IKKβ, the proteasome/ubiquitin pathway, the 20S proteasome, the PI3K/Akt pathway, or mTOR, ONY-015, INGN201, PS1145, Bortezomib, CCI779, RAD-001, an siRNA targeting MDM2, mixed lineage kinase domain like (MLKL) protein, rapamycin (RAP) or derivatives and/or analogs thereof, everolimus or RAD001; CCI-779, ABT578, SAR543, ascomycin (an ethyl analog of FK506), AP23573, AP23841, KU-0063794, INK-128, EX2044, EX3855, EX7518, compounds that bind to the ATP-binding cleft of mTOR, AZD08055, OSI027.

11. The method of claim 1, wherein said anti-CAA antibody and said second therapeutic agent exhibit enhanced therapeutic efficacy relative to said anti-CAA antibody and said second therapeutic agent administered individually.

12. The method of claim 1, wherein said anti-CAA antibody comprises a NEO-201 antibody comprising:
   (a) a light chain variable region polypeptide comprising the polypeptide of SEQ ID NO: 76 or a polypeptide comprising the CDRs thereof and having at least 90% identity thereto and/or a heavy chain variable region polypeptide comprising the polypeptide of SEQ ID NO: 81 or a polypeptide comprising the CDRs thereof and having at least 90% identity thereto;
   (b) a light chain variable region polypeptide comprising the polypeptide of any one of SEQ ID NOs: 85-89 or a polypeptide comprising the CDRs thereof and having at least 90% identity thereto and optionally containing the light constant domain contained in SEQ ID NO: 52, 62, or 72 and/or a heavy chain variable region polypeptide comprising the polypeptide of any one of SEQ ID NOs: 90-94 or a polypeptide comprising the CDRs thereof and having at least 90% identity thereto and optionally containing the heavy constant domain contained in SEQ ID NO: 57, 67, or 74;
   (c) a light chain comprising the polypeptide of SEQ ID NO: 96 and/or a heavy chain comprising the polypeptide of SEQ ID NO: 101,
   wherein said anti-CAA antibody and said second therapeutic agent are administered at a lower dosage than the effective dosage of said anti-CAA antibody or said second therapeutic agent when administered individually, wherein said method is for the treatment of a cancer that expresses an antigen specifically bound by said anti-CAA antibody.

13. The method of claim 1, wherein said anti-CAA antibody is chimeric or humanized.

14. The method of claim 1, wherein said anti-CAA antibody and said second therapeutic agent are administered to said subject together or separately.

15. The method of claim 1, which results in apoptosis of cancer cells in said subject.

16. The method of claim 1, wherein said cancer is selected from the group consisting of: a carcinoma, colon cancer, pancreatic cancer, lung cancer, prostate cancer, melanoma, breast cancer, ovarian cancer, uterine cancer, cervical cancer, and mesothelioma, or is selected from the group consisting of: breast cancer, ovarian cancer, uterine cancer, cervical cancer.

17. The method of claim 1, wherein said cancer comprises breast, ovarian, uterine, or cervical cancer.

18. The method of claim 1, wherein said antibody and said second therapeutic agent exhibit a synergistic effect on treatment outcome.

19. The method of claim 18, wherein said synergistic effect is determined based on: reduction in the number of cancer cells or absence of the cancer cells; reduction in the tumor size; inhibition of cancer cell infiltration into peripheral organs including the spread of cancer into soft tissue and bone; inhibition of tumor metastasis; inhibition, to some extent, of tumor growth; relief of one or more of the symptoms associated with the specific cancer; reduced morbidity; reduced mortality; or improvement in quality of life.

20. The method of claim 1, wherein said second agent is a platin or doxorubicin.

* * * * *